US006077668A

United States Patent [19]
Kool

[11] Patent Number: 6,077,668
[45] Date of Patent: Jun. 20, 2000

[54] HIGHLY SENSITIVE MULTIMERIC NUCLEIC ACID PROBES

[75] Inventor: Eric T. Kool, Rochester, N.Y.

[73] Assignee: University of Rochester, Rochester, N.Y.

[21] Appl. No.: 08/910,632

[22] Filed: Aug. 13, 1997

Related U.S. Application Data

[63] Continuation-in-part of application No. 08/805,631, Feb. 26, 1997, and application No. 08/393,439, Feb. 23, 1995, Pat. No. 5,714,320, which is a continuation-in-part of application No. 08/047,860, Apr. 15, 1993, abandoned.

[51] Int. Cl.$^7$ .............................. C12P 19/34; C12Q 1/68; C07H 21/02; C07H 21/04
[52] U.S. Cl. ........................... 435/6; 435/91.1; 435/91.3; 435/320.1; 536/23.1; 536/24.3; 536/24.31; 536/24.32; 536/24.33; 536/25.3; 536/25.32
[58] Field of Search ........................... 436/6, 172.3, 91.1, 436/91.3, 320.1; 536/23.1, 24.3, 24.31, 24.32, 24.33, 25.3, 25.32

[56] References Cited

U.S. PATENT DOCUMENTS

| | | | |
|---|---|---|---|
| 4,795,700 | 1/1989 | Dervan et al. | 435/5 |
| 4,837,312 | 6/1989 | Dervan et al. | 536/25.32 |
| 4,987,071 | 1/1991 | Cech et al. | 435/91.31 |
| 5,093,246 | 3/1992 | Cech et al. | 435/6 |
| 5,246,921 | 9/1993 | Reddy et al. | 514/44 |
| 5,258,506 | 11/1993 | Urdea et al. | 536/23.1 |
| 5,354,668 | 10/1994 | Auerbach | 435/91.1 |
| 5,354,855 | 10/1994 | Cech et al. | 536/24.1 |
| 5,426,180 | 6/1995 | Kool | 536/25.3 |
| 5,470,724 | 11/1995 | Ahern | 435/91.2 |
| 5,498,531 | 3/1996 | Jarrell | 435/91.31 |
| 5,500,357 | 3/1996 | Taira et al. | 435/91.31 |
| 5,714,320 | 2/1998 | Kool | 435/6 |

FOREIGN PATENT DOCUMENTS

| | | |
|---|---|---|
| 4-304900 | 10/1992 | Japan . |
| 5-146299 | 6/1993 | Japan . |
| WO92/17484 | 10/1992 | WIPO . |
| WO 92/01813 | 2/1993 | WIPO . |
| WO 94/03630 | 2/1994 | WIPO . |
| WO 96/33207 | 10/1996 | WIPO . |
| WO 97/19193 | 5/1997 | WIPO . |
| WO 97/20948 | 6/1997 | WIPO . |

OTHER PUBLICATIONS

Uhlmann et al. Antisense Oligonucleotides: A New Therapuetic Principle. Chemical Reviews vol. 90(4):544–584, Jun. 1990.

Uhlen. Magnetic seperation of DNA. Nature vol. 340:733, Aug. 31, 1989.

Kawai et al. A Simple Method of Detecting Amplified DNA with Immobilized Probes on Microtiter Wells. Analytical Biochemistry vol. 209:63–69, Feb. 15, 1993.

Ledwith et al. Preparation of Synthetic Tandem–Repetitive probes for DNA Fingerprinting. Biotechniques vol. 9(2):149–152, 1990.

May et al. DNA Fingerprinting by Specific Priming of Concatenated Oligonucleotides. Nucleic Acids Research vol. 19(16):4557, 1991.

Ali S. Enzymatic Synthesis of DNA Probes Complementary to a Human Variable Number Tandem Repeat Locus. Analytical Biochemistry vol. 179:280–283, 1989.

"Affinity Chromatography: Practical and Theoretical Aspects", Ed. P. Mohr; Dekker Publishing; New York (1985); Title page, Copyright page, and Contents pages (pp. v–viii).

Aguilar, L. et al., "Hairpin, Dumbbell, and Single–Stranded Phosphodiester Oligonucleotides Exhibit Identical Uptake in T. Lymphocyte Cell Lines", *Antisense & Nucleic Acid Drug Development*, 6, 157–163 (1996).

Aiyar, S. E. et al., "A Mismatch Bubble in Double–stranded DNA Suffices to Direct Precise Transcription Initiation by *Escherichia coli* RNA Polymerase", *J. Biol. Chem.*, 269(18), 13179–13184 (1994).

Albrecht, T. et al., "Cationic lipide mediated transfer of c–abl and bcr antisense oligonucleotides to immature normal myeloid cells: Uptake, biological effects and modulation of gene expression", *Ann. Hematol.*, 72, 73–79 (1996).

Ashley, G.W., et al., "Chemical Synthesis of Oligodeoxynucleotide Dumbbells", *Biochemistry*, 30, 2927–2933 (1991).

Beaucage, S.L., et al., "Deoxynucleoside Phosphoramidites—A New Class of Key Intermediates for Deoxypolynucleotide Synthesis", *Tetrahedron Lett.*, 22(20), 1859–1862 (1981).

Beaucage, S.L., et al. "The Functionalization of Oligonucleotides Via Phosphoramidite Derivatives," *Tetrahedron*, 49(10), 1925–1963 (1993).

Blanco, L. et al., "Highly Efficient DNA Synthesis by the Phage $\phi$29 DNA Polymerase", *J. Biol. Chem.*, 264(15), 8935–8940 (1989).

Bledsoe, A. H. et al., "Molecular Homology and DNA Hybridization," *J. Mol. Evol.*, 30, 425–433 (1990).

Bock, L.C., et al., "Selection of single–stranded DNA molecules that bind and inhibit human thrombin", *Nature*, 355, 564–566 (1992).

(List continued on next page.)

*Primary Examiner*—John S. Brusca
*Assistant Examiner*—Sean McGarry
*Attorney, Agent, or Firm*—Mueting, Raasch & Gebhardt, P.A.

[57] ABSTRACT

The present invention provides detectably labeled RNA and DNA oligonucleotide multimers useful as diagnostic probes in medical, biological and chemical applications. A method for synthesizing DNA and RNA oligonucleotides, oligonucleotide multimers, and analogs, preferably those that are detectably labeled, is also provided. Oligonucleotide synthesis is performed by combining a circular single-stranded oligonucleotide template with an effective polymerase and at least two types of nucleotide triphosphate, without the addition of auxiliary proteins, to yield an oligonucleotide multimer comprising multiple copies of a repeated oligonucleotide sequence.

66 Claims, 8 Drawing Sheets

OTHER PUBLICATIONS

Capaccioli, S. et al., "Cationic Lipids Improve Antisense Oligonucleotide Uptake and Prevent Degradation in Cultured Cells and in Human Serum", *Biochemical and Biophysical Research Communications*, 197(2), 818–825 (1993).

Chin, J., et al., "Catalytic Hydrolysis of Amides at Neutral pH", *J. Chem. Soc., Chem. Commun.*, 1326–1328 (1990).

Compton, J., "Nucleic acid sequence based amplification", *Nature*, 350, 91–92 (1991).

Cwirla, S. E. et al., "Peptides on phage: A vast library of peptides for identifying ligands", *PNAS USA*, 87, 6378–6382 (1990).

Daube, S. S. et al., "Functional Transcription Elongation Complexes from Synthetic RNA–DNA Bubble Duplexes", *Science*, 258, 1320–1324 (1992).

Daubendiek, S. L., et al., "Rolling–Circle RNA Synthesis: Circular Oligonucleotides as Efficient Substrates for T7 RNA Polymerase", *J. Am. Chem. Soc.*, 117, 7818–7819 (1995).

D'Souza, D. J. et al., "Strong Binding of Single–stranded DNA by Stem–Loop Oligonucleotides", *J. Biomolecular Structure and Dynamics*, 10(1), 141–152 (1992).

Dzianott, A. M., et al., "Derivation of an infectious viral RNA by autolytic cleavage of in vitro transcribed viral cDNAs", *PNAS USA*, 86, 4823–4827 (1989).

Egholm, M. et al., "PNA hybridizes to complementary oligonucleotides obeying the Watson–Crick hydrogen–bonding rules," *Nature*, 365, 566–568 (1993).

Eisenberg, S. et al., "The Single–Stranded DNA Phages", Eds., Denhardt, D.T., Cold Spring Harbor Press, Cold Spring Harbor, Title page, Copyright Page, Contents Pages, pp. 298–299 (1978).

Eisenberg, S., et al., "Enzymatic replication of viral and complementary strands of duplex DNA of phage φX174 proceeds by separate mechanisms", *PNAS USA*, 73(9), 3151–3155 (1976).

Ellington, A. D., et al., "In vitro selection of RNA molecules that bind specific ligands", *Nature*, 346, 818–822 (1990).

Ellington, A. D., et al., "Selection in vitro of single–stranded DNA molecules that fold into specific ligand–binding structures", *Nature*, 355, 850–852 (1992).

Famulok, M., et al., "Stereospecific Recognition of Tryptophan Agarose by in vitro Selected RNA", *J. Am. Chem. Soc.*, 114, 3990–3991 (1992).

Fire, A., et al., "Rolling replication of short DNA circles", *PNAS USA*, 92, 4641–4645 (1995).

Forster, A.C. et al., "Structural and Ionic Requirements for Self–cleavage of Virusoid RNAs and trans Self–cleavage of Viroid RNA", *Cold Spring Harbor Symposia on Quantitative Biology*, LII, 249–259 (1987).

Grosshans, C. A., et al., "A hammerhead ribozyme allows synthesis of a new form of the Tetrahymena ribozyme homogenous in length with a 3' end blocked for transesterification", *Nucleic Acids Research*, 19(14), 3875–3880 (1991).

Gura, T., "Antisense Has Growing Pains", *Science*, 270, 575–577 (1995).

Guy–Caffey, J. K., et al., "Novel Polyaminolipids Enhance the Cellular Uptake of Oligonucleotides", *J. Biol. Chem.*, 270(52), 31391–31396 (1995).

Harshey, et al., "A mechanism of DNA transposition", *PNAS USA*, 78, 1090–1094 (1981).

Haseloff, J., et al., "Simple RNA Enzymes with New and Highly Specific Endoribonuclease Activities", *Nature*, 334, 585–591 (1988).

Horn, T. et al., "The Synthesis of Branched Oligonucleotides as Signal Amplification Multimers for Use in Nucleic Acid Assays," *Nucleosides & Nucleotides*, 8(5&6), 875–877 (1989).

Hutchins, C. J., et al., "Self–cleavage of plus and minus RNA transcripts of avocado sunblotch viroid", *Nucleic Acids Research*, 14(9), 3627–3641 (1986).

James, W., "Towards gene–inhibition therapy: a review of progress and prospects in the field of antiviral antisense nucleic acids and ribozymes", *Antiviral Chemistry & Chemotherapy*, 2(4), 191–214 (1991).

Kanaya, E., et al., "Template–Directed Polymerization of Oligoadenylates Using Cyanogen Bromide", *Biochemistry*, 25, 7423–7430 (1986).

Kazakov, S., et al., "A Trinucleotide Can Promote Metal Ion–Dependent Specific Cleavage of RNA", *Pro. Natl. Acad. Sci. USA*, 89, 7939–7943 (1992).

Kim, J. H., et al., "Dimethyl Phosphate Hydrolysis at Neutral pH", *J. Am. Chem. Soc.*, 114, 9792–9795 (1992).

Kitajima, I., et al., "Ablation of Transplanted HTLV–I Tax–Transformed Tumors in Mice by Antisense Inhibition of NF–κB", *Science*, 258, 1792–1795 (1992).

Koo, Hyeon–Sook, et al., "Determination of the Extent of DNA Bending by an Adenine–Thymine Tract", *Biochemistry*, 29, 4227–4234 (1990).

Kool, E., "Molecular Recognition by Circular Oligonucleotides: Increasing the Selectivity of DNA Binding", *J. Am. Chem. Soc.*, 113, 6265–6266 (1991).

Kool, E. T., et al., "Abstract of National Institute of Health Grant No. R01–GM46625" (prior to Feb. 1997).

Kool, E.T., " Binding of HIV 1 Sequences By Cyclic Oligonucleotides," Abstract of the National Institute of General Medical Sciences Grant No. 5R01GM46625–06 (1997).

Kool, E.T., "New Multilabel Fluorescent Groups for Increased Sensitivity of DNA Detection," Report No. ARO 31507.10–LS–YIP, U.S. Army Research Office, pp. 1–7 (Oct. 1996).

Kool, E.T., "Topologically Modified Bipolymers: Properties of Synthetic Circular DNAs and RNAs," Report No. ARO 31507.5–LS–YIP, U.S. Army Research Office, pp. 336–402 (May 1996).

Kool, E.T. "Circular Oligonucleotides as Potential Modulators of Gene Expression," Report No. ARO 315.8–LS–YIP, U.S. Army Research Office, pp. 124–149 (May 1996).

Kornberg, A. "DNA Replication", W.H. Freeman & Co., San Francisco, 569 (1980).

Krupp, G. "Unusual promoter–independent transcription reactions with bacteriophase RNA polymerases", *Nucleic Acids Research*, 17(8), 3023–3036 (1989).

Long, D. M., et al., "Self–cleaving catalytic RNA", *FASEB*, 7(1), 25–30 (1993).

Milligan J. F., et al., "Oligoribonucleotide synthesis of T7 RNA polymerase and synthetic DNA templates", *Nucleic Acids Res.*, 15(21), 8783–8798 (1987).

Miyamoto, Y., et al., "Total Synthesis of (+)–Validoxylamine G", *J. Chem. Soc., Chem. Commun.*, 999–1000 (1990).

Møllegaard, N. E., et al., "Peptide nucleic acid–DNA strand displacement loops as artificial transcription promoters", *PNAS USA*, 91, 3892–3895 (1994).

Nilsson M. et al., "Padlock Probes: Circularizing Oligonucleotides for Localized DNA Detection," *Science*, 265, 2085–2088 (1994).

"New England BioLabs Catalog", oX174, (1994).

"Oligodeoxynucleotides: Antisense Inhibitors of Gene Expression", J. S. Cohen, Ed.; CRC Press: Boca Raton, FL, 1989; Title page, Copyright page, and Contents pages (pp. v–viii).

Ohkawa, J. et al., et al., "Importance of independence in ribozyme reactions: Kinetic behavior of trimmed and of simply connected multiple ribozymes with potential activity against human immunodeficiency virus", *PNAS USA*, 90, 11302–11306 (1993).

Olivera, B. M., et al., "Enzymic Joining of Polynucleotides: IV. Formation of a Circular Deoxyandeylate–Deoxythymidylate Copolymer", *J. Mol. Biol.*, 36, 275–285 (1968).

Pei, D., et al., "A Combinatorial Approach Toward DNA Recognition", *Science*, 253, 1408–1411 (1991).

Piccirilli, J., et al., "Enzymatic Incorporation of a New Base Pair into DNA and RNA Extends the Genetic Alphabet", *Nature*, 343, 33–37 (1990).

Podhadjska, A., et al., "Conversion of the FokI Endonuclease to a Universal Restriction Enzyme: Cleavage of Phage M13mp7 DNA at Predetermined Sites", *Gene*, 40, 175–182 (1985).

Prakash, G., et al., "Molecular Recognition by Circular Oligonucleotides. Strong Binding of Single–stranded DNA and RNA", *J. Chem. Soc., Chem. Commun.*, 17, 1161–1163 (1991).

Prakash, G., et al., "Structural Effects in the Recognition of DNA by Circular Oligonucleotides", *J. Am. Chem. Soc.*, 114, 3523–3527 (1992).

Ratajczak, M.Z., et al., "In vivo treatment of human leukemia in a scid mouse model with c–myb antisense oligodeoxynucleotides", *PNAS*, 89, 11823–11827 (1992).

Roberts, R. W . et al., "Specificity and stringency in DNA triplex formation," *Proc. Natl. Acad. Sci. USA*, 88, 9397–9401 (1991).

Robertson, D. L. et al., "Selection in vitro of an RNA enzyme that specifically cleaves single–stranded DNA", *Nature*, 344, 467–468 (1990).

Robertson, H. D. et al., "The Viroid Replication Process", J. S. Semancik, Ed.; CRC Press, Inc., Boca Raton, FL (1987); *Viroids and Viroid–Like Pathogens*, Chapt. 2, pp. 50–68.

Rubin, E. et al., "Convergent DNA synthesis: a non–enzymatic dimerization approach to circular oligodeoxynucleotides", *Nucleic Acids Research*, 23(17), 3547–3553 (1995).

Ruffner, D. E., et al., "Studies on the hammerhead RNA self–cleaving domain", *Gene*, 82, 31–41 (1989).

Rumney, S., et al., "DNA Recognition by Hybrid Oligoether–Oligodeoxynucleotide Macrocylces", *Angew. Chem. Intl. Ed. English*, 31(12), 1617–1619 (1992).

Saiki, R. K., et al., "Primer–Directed Enzymatic Amplification of DNA with a Thermostable DNA Polymerase", *Science*, 239, 487–491 (1988).

Sambrook, et al., "Molecular Cloning: A Laboratory Guide", 2nd ed.; Cold Spring Harbor, NY(1989), Title page, copyright page, contents pages (pp. v–xxxii), and Chapter 13 (pp. 13.2–13.104).

Sarver, N. et al., "Ribozymes as Potential Anti–HIV–1 Therapeutic Agents", *Science*, 247, 1222–1225 (1990).

Scaringe, S.A., et al., "Chemical Synthesis of Biologically Active Oligoribonucleotides Using β–cyanoethyl Protected Ribonucleoside Phosphoramidites", *Nucleic Acids Res.*, 18(18), 5433–5441 (1990).

Schubbert, R., et. al., "Ingested foreign (phage M13) DNA survives transiently in the gastrointestinal tract and enters the bloodstream of mice", *Mol. Gen. Genet.*, 242(5), 495–504 (1994).

Simon, E. S., et al., "Convenient Syntheses of Cytidine 5'–Triphosphate, Guanosine 5'–Triphosphate, and Uridine 5'–Triphosphate and Their use in the Preparation of UDP–glucose, UDP–glucuronic Acid, and GCP–mannose", *J. Org. Chem.*, 55(6), 1834–1841 (1990).

*Short Protocols in Molecular Biology*, Chapt. 14, $3^{rd}$ Edition, Wiley & Sons (1995).

Symons, R. H., "Avocado sunblotch viroid: primary sequence and proposed secondary structure", *Nucleic Acids Research*, 9(23) 6527–6537 (1981).

Symons, R., "Small Catalytic RNAs", *Annu. Rev. Biochem.*, 61, 641–671 (1992).

Szybalski, W., et al., "Universal Restriction Endonucleases: Designing Novel Cleavage Specificities by Combining Adaptor Oligodeoxynucleotide and Enzyme Moieties", *Gene*, 40, 169–173 (1985).

Taira, K. et al., "Construction of a novel RNA–transcript–trimming plasmid which can be used both in vitro in place of run–off and (G)–free transcriptions and in vivo as multi–sequences transcription vectors", *Nucleic Acids Research*, 19(19), 5125–5130 (1991).

Tessier, D.C., et al., "Ligation of Single–stranded oligodeoxyribonucleotides by T4 RNA Ligase", *Anal. Biochem.*, 158, 171–178 (1986).

Tomizawa, J., et al., "Factor–Independent Termination of Transcription in a Stretch of Deoxyadenosine Residues in the Template DNA", *Cell*, 51, 623–630 (1987).

Tuerk, C., et al., "RNA Pseudoknots that Inhibit Human Immunodefiency Virus Type 1 Reverse Transcriptase", *PNAS*, 89, 6988–6992 (1992).

Tuerk, C., et al., "Systematic Evolution of ligands by exponential enrichment: RNA ligands to Bacteriophage T4 DNA Polymerase", *Science*, 249, 505–510 (1990).

Uhlenbeck, O. C., "A small catalytic oligoribonucleotide", *Nature*, 328, 596–600 (1987).

Uhlmann, E., et al., "Antisense oligonucleotides: a new therapeutic principle", *Chem. Rev*, 90(4), 543–584 (1990).

Ulanovsky, L., "Curved DNA: Design, synthesis, and circularization", *PNAS USA*, 83(4), 862–866 (1986).

Vaishnav, Y., et al., "The Biochemistry of AIDS", *Ann. Rev. Biochem.*, 60, 577–630 (1991).

Walker, G. T., et al., "Isothermal in vitro amplification of DNA by a restriction enzyme/DNA polymerase system", *PNAS USA*, 89, 392–396 (1992).

Wang, S. et al., "Circular RNA Oligonucleotides. Synthesis, nucleic acid binding properties, and a comparison with circular DNAs", *Nucleic Acids Research*, 22(12), 2326–2333 (1994).

Watson, "Molecular Biology of the Gene", W. A. Benjamin, Inc., 238–241 (1976).

D. Liu et al., "Rolling Circle DNA Synthesis: Small Circular Oligonucleotides as Efficient Templates for DNA Polymers," *J. Am. Chem. Soc.*, 118, 1587–1594 (1996).

S. L. Daubendiek et al., "Generation of Catalytic RNAs by Rolling Transcription of Synthetic DNA Nanocircles," *Nature Biotech.*, 15, 273–277 (Mar. 1997).

SEQUENCE LISTING

<160> NUMBER OF SEQ ID NOS: 83

<210> SEQ ID NO 1
<211> LENGTH: 34
<212> TYPE: DNA
<213> ORGANISM: Artificial Sequence
<220> FEATURE:
<223> OTHER INFORMATION: linear 34-nucleotide precircle DNA
      oligonucleotide

<400> SEQUENCE: 1
aaagaagagg gaagaaagaa aagggtgga aaag                                34

<210> SEQ ID NO 2
<211> LENGTH: 34
<212> TYPE: DNA
<213> ORGANISM: Artificial Sequence
<220> FEATURE:
<223> OTHER INFORMATION: oligonucleotide product

<400> SEQUENCE: 2
ttttccaccc cttttctttc ttccctcttc tttc                                34

<210> SEQ ID NO 3
<211> LENGTH: 34
<212> TYPE: DNA
<213> ORGANISM: Artificial Sequence
<220> FEATURE:
<223> OTHER INFORMATION: cyclized precircle template

<400> SEQUENCE: 3
gaaagaagag ggaagaaaga aagggtgg aaaa                                  34

<210> SEQ ID NO 4
<211> LENGTH: 204
<212> TYPE: DNA
<213> ORGANISM: Artificial Sequence
<220> FEATURE:
<223> OTHER INFORMATION: nucleotide multimer

<400> SEQUENCE: 4
ttttccaccc cttttctttc ttccctcttc tttcttttcc acccctttc tttcttccct    60 cttctttctt ttccacccct tttctttctt ccctcttctt tcttttccac ccctttcttt   120
tcttccctct tctttctttt ccacccttt tcttcttcc ctcttcttc ttttccaccc     180 cttttctttc ttccctcttc tttc                                          204

<210> SEQ ID NO 5
<211> LENGTH: 26
<212> TYPE: DNA
<213> ORGANISM: Artificial Sequence
<220> FEATURE:
<223> OTHER INFORMATION: synthetic AS83 DNA nanocircle

<400> SEQUENCE: 5
caaaaaaaaa aaacaaaaaa aaaaaa                                        26

<210> SEQ ID NO 6
<211> LENGTH: 29
<212> TYPE: DNA
<213> ORGANISM: Artificial Sequence
<220> FEATURE:
<223> OTHER INFORMATION: multimer

<400> SEQUENCE: 6
tttgtttttt tttttgttt ttttttttt          29

<210> SEQ ID NO 7
<211> LENGTH: 12
<212> TYPE: DNA
<213> ORGANISM: Artificial Sequence
<220> FEATURE:
<223> OTHER INFORMATION: oligomer

<400> SEQUENCE: 7
tttttttttt tt          12

<210> SEQ ID NO 8
<211> LENGTH: 12
<212> TYPE: DNA
<213> ORGANISM: Artificial Sequence
<220> FEATURE:
<223> OTHER INFORMATION: linear sequence

<400> SEQUENCE: 8
aagaaagaaa ag          12

<210> SEQ ID NO 9
<211> LENGTH: 39
<212> TYPE: DNA
<213> ORGANISM: Artificial Sequence
<220> FEATURE:
<223> OTHER INFORMATION: circular template

<400> SEQUENCE: 9
cttagagacg aagatcaaac gtctctaaga cttttcttt          39

<210> SEQ ID NO 10
<211> LENGTH: 117
<212> TYPE: DNA
<213> ORGANISM: Artificial Sequence
<220> FEATURE:
<223> OTHER INFORMATION: product of rolling circle synthesis

<400> SEQUENCE: 10
tcttagagac gtttgatctt cgtctctaag aaagaaaagt cttagagacg tttgatcttc          60
gtctctaaga aagaaaagtc ttagagacgt tgatcttcg tctctaagaa agaaaag          117

<210> SEQ ID NO 11
<211> LENGTH: 12
<212> TYPE: DNA
<213> ORGANISM: Artificial Sequence
<220> FEATURE:
<223> OTHER INFORMATION: desired oligomer

<400> SEQUENCE: 11
aagaaagaaa ag          12

<210> SEQ ID NO 12
<211> LENGTH: 27
<212> TYPE: DNA
<213> ORGANISM: Artificial Sequence
<220> FEATURE:
<223> OTHER INFORMATION: hairpins

<400> SEQUENCE: 12
tcttagagac gtttgatctt cgtctct          27

```
<210> SEQ ID NO 13
<211> LENGTH: 34
<212> TYPE: DNA
<213> ORGANISM: Artificial Sequence
<220> FEATURE:
<223> OTHER INFORMATION: precircle

<400> SEQUENCE: 13
gatcagaaaa gaaagaagga ggaagaaaga aaag                              34

<210> SEQ ID NO 14
<211> LENGTH: 34
<212> TYPE: DNA
<213> ORGANISM: Artificial Sequence
<220> FEATURE:
<223> OTHER INFORMATION: circular template

<400> SEQUENCE: 14
gaaaagaaag aaggaggaag aaagaaaagg atca                              34

<210> SEQ ID NO 15
<211> LENGTH: 44
<212> TYPE: DNA
<213> ORGANISM: Artificial Sequence
<220> FEATURE:
<223> OTHER INFORMATION: product of rolling circle synthesis

<400> SEQUENCE: 15
gatccttttc tttcttcctc cttctttctt ttctgatcct tttc                   44

<210> SEQ ID NO 16
<211> LENGTH: 34
<212> TYPE: DNA
<213> ORGANISM: Artificial Sequence
<220> FEATURE:
<223> OTHER INFORMATION: desired circular oligomer

<400> SEQUENCE: 16
ttctttcttt tctgatcctt ttctttcttc ctcc                              34

<210> SEQ ID NO 17
<211> LENGTH: 39
<212> TYPE: DNA
<213> ORGANISM: Artificial Sequence
<220> FEATURE:
<223> OTHER INFORMATION: product of rolling circle synthesis

<400> SEQUENCE: 17
gatcagaaaa gaaagaagga ggaagaaaga aaaggatca                         39

<210> SEQ ID NO 18
<211> LENGTH: 34
<212> TYPE: DNA
<213> ORGANISM: Artificial Sequence
<220> FEATURE:
<223> OTHER INFORMATION: oligomer

<400> SEQUENCE: 18
aaaagaaaga aggaggaaga aagaaaagga tcag                              34

<210> SEQ ID NO 19
<211> LENGTH: 34
<212> TYPE: DNA
<213> ORGANISM: Artificial Sequence
<220> FEATURE:
<223> OTHER INFORMATION: product of cutting linear multimer
```

```
<400> SEQUENCE: 19 gatcctttc tttcttcctc cttctttctt ttct                          34

<210> SEQ ID NO 20
<211> LENGTH: 33
<212> TYPE: DNA
<213> ORGANISM: Artificial Sequence
<220> FEATURE:
<223> OTHER INFORMATION: desired oligomer

<400> SEQUENCE: 20
cgagaaaaga agaaggagg aagaaagaaa aga                           33

<210> SEQ ID NO 21
<211> LENGTH: 34
<212> TYPE: DNA
<213> ORGANISM: Artificial Sequence
<220> FEATURE:
<223> OTHER INFORMATION: circular template

<400> SEQUENCE: 21
gatcttttct tcttcctcc ttctttcttt tctc                          34

<210> SEQ ID NO 22
<211> LENGTH: 39
<212> TYPE: DNA
<213> ORGANISM: Artificial Sequence
<220> FEATURE:
<223> OTHER INFORMATION: precircle

<400> SEQUENCE: 22
agacgaagat caaacgtctc taagactttt ctttcttag                    39

<210> SEQ ID NO 23
<211> LENGTH: 31
<212> TYPE: DNA
<213> ORGANISM: Artificial Sequence
<220> FEATURE:
<221> NAME/KEY: unsure
<222> LOCATION: 4-23
<223> OTHER INFORMATION: precircle

<400> SEQUENCE: 23
aggnnnnnnn nnnnnnnnnn nnnaaaaaac c                            31

<210> SEQ ID NO 24
<211> LENGTH: 31
<212> TYPE: DNA
<213> ORGANISM: Artificial Sequence
<220> FEATURE:
<221> NAME/KEY: unsure
<222> LOCATION: 12-31
<223> OTHER INFORMATION: circularized precircle

<400> SEQUENCE: 24
aaaaaaccag gnnnnnnnnn nnnnnnnnnn n                            31

<210> SEQ ID NO 25
<211> LENGTH: 31
<212> TYPE: DNA
<213> ORGANISM: Artificial Sequence
<220> FEATURE:
<221> NAME/KEY: unsure
<222> LOCATION: 10-29
<223> OTHER INFORMATION: product of rolling circle synthesis

<400> SEQUENCE: 25
```

```
tggtttttn nnnnnnnnnn nnnnnnnnnc c                              31

<210> SEQ ID NO 26
<211> LENGTH: 31
<212> TYPE: DNA
<213> ORGANISM: Artificial Sequence
<220> FEATURE:
<221> NAME/KEY: unsure
<222> LOCATION: 7-26
<223> OTHER INFORMATION: circularized product

<400> SEQUENCE: 26 tttttnnnn nnnnnnnnn nnnnnncctg g                               31

<210> SEQ ID NO 27
<211> LENGTH: 11
<212> TYPE: DNA
<213> ORGANISM: Artificial Sequence
<220> FEATURE:
<223> OTHER INFORMATION: ligation adaptor

<400> SEQUENCE: 27
ttttctttct t                                                   11

<210> SEQ ID NO 28
<211> LENGTH: 42
<212> TYPE: DNA
<213> ORGANISM: Artificial Sequence
<220> FEATURE:
<223> OTHER INFORMATION: 42 nt circle

<400> SEQUENCE: 28
ctttcttctt tccttcgatt cctttcttct ttccttcgat tc                 42

<210> SEQ ID NO 29
<211> LENGTH: 58
<212> TYPE: DNA
<213> ORGANISM: Artificial Sequence
<220> FEATURE:
<223> OTHER INFORMATION: 58 nt circle

<400> SEQUENCE: 29
ctttcttctt tcctttctc gatcttttcc tttcttcttt ccttttctcg atcttttc 58

<210> SEQ ID NO 30
<211> LENGTH: 74
<212> TYPE: DNA
<213> ORGANISM: Artificial Sequence
<220> FEATURE:
<223> OTHER INFORMATION: 74 nt circle

<400> SEQUENCE: 30
ctttcttctt tcctttctt tttcgatttt tcttttcctt tcttctttcc ttttcttttt  60 cgattttct tttc                                                    74

<210> SEQ ID NO 31
<211> LENGTH: 16
<212> TYPE: DNA
<213> ORGANISM: Artificial Sequence
<220> FEATURE:
<223> OTHER INFORMATION: primer sequence

<400> SEQUENCE: 31
aggaaagaag aaagga                                              16
```

-continued

<210> SEQ ID NO 32
<211> LENGTH: 18
<212> TYPE: DNA
<213> ORGANISM: Artificial Sequence
<220> FEATURE:
<223> OTHER INFORMATION: primer

<400> SEQUENCE: 32
tgttaacttc tgcgtcat                                                     18

<210> SEQ ID NO 33
<211> LENGTH: 41
<212> TYPE: DNA
<213> ORGANISM: Artificial Sequence
<220> FEATURE:
<221> NAME/KEY: unsure
<222> LOCATION: 18-37
<223> OTHER INFORMATION: DNA circle

<400> SEQUENCE: 33
tctcttcgac tctctctnnn nnnnnnnnnn nnnnnnntct c                            41

<210> SEQ ID NO 34
<211> LENGTH: 41
<212> TYPE: DNA
<213> ORGANISM: Artificial Sequence
<220> FEATURE:
<221> NAME/KEY: unsure
<222> LOCATION: 18-37
<223> OTHER INFORMATION: 41 mer circle library

<400> SEQUENCE: 34
tctcttcgac tctctctnnn nnnnnnnnnn nnnnnnntct c                            41

<210> SEQ ID NO 35
<211> LENGTH: 34
<212> TYPE: DNA
<213> ORGANISM: Artificial Sequence
<220> FEATURE:
<223> OTHER INFORMATION: 34 nt circle

<400> SEQUENCE: 35
tcttttcccc accttttctt tcttcctcct tctt                                   34

<210> SEQ ID NO 36
<211> LENGTH: 12
<212> TYPE: DNA
<213> ORGANISM: Artificial Sequence
<220> FEATURE:
<223> OTHER INFORMATION: primer

<400> SEQUENCE: 36
aagaaagaaa ag                                                           12

<210> SEQ ID NO 37
<211> LENGTH: 34
<212> TYPE: DNA
<213> ORGANISM: Artificial Sequence
<220> FEATURE:
<223> OTHER INFORMATION: primer

<400> SEQUENCE: 37
tttcttcctc cttctttctt ttcccacct tttc                                    34

<210> SEQ ID NO 38
<211> LENGTH: 34

```
<212> TYPE: DNA
<213> ORGANISM: Artificial Sequence
<220> FEATURE:
<221> NAME/KEY: modified base
<222> LOCATION: 4, 9, 15, 20, 24, 34
<223> OTHER INFORMATION: m5c

<400> SEQUENCE: 38
tttcttttct cgatcttttc tttctttttt tttc                          34

<210> SEQ ID NO 39
<211> LENGTH: 20
<212> TYPE: DNA
<213> ORGANISM: Artificial Sequence
<220> FEATURE:
<223> OTHER INFORMATION: optimized T7 RNA polymerase promoter

<400> SEQUENCE: 39
ccctatagtg agtcgtatta                                          20

<210> SEQ ID NO 40
<211> LENGTH: 53
<212> TYPE: DNA
<213> ORGANISM: Artificial Sequence
<220> FEATURE:
<223> OTHER INFORMATION: DNA 53mer circle

<400> SEQUENCE: 40
tttcttcccc cgaagaaaag agaaggagag agatccctag agagaggaag act     53

<210> SEQ ID NO 41
<211> LENGTH: 53
<212> TYPE: RNA
<213> ORGANISM: Artificial Sequence
<220> FEATURE:
<223> OTHER INFORMATION: stem-loop RNA multimer which binds HIV-1 gag
      RNA

<400> SEQUENCE: 41
gggaagaaaa gucuuccucu cucuagggau cucucuccuu ucuuuucuu cgg      53

<210> SEQ ID NO 42
<211> LENGTH: 53
<212> TYPE: DNA
<213> ORGANISM: Artificial Sequence
<220> FEATURE:
<223> OTHER INFORMATION: DNA 53mer circle

<400> SEQUENCE: 42
tttcttcccc cgaagaaaag aataaggaag aagcctccga agaaggaaca act     53

<210> SEQ ID NO 43
<211> LENGTH: 53
<212> TYPE: RNA
<213> ORGANISM: Artificial Sequence
<220> FEATURE:
<223> OTHER INFORMATION: stem-loop RNA multimer which binds bcr-abl
      mRNA

<400> SEQUENCE: 43
gggaagaaaa guuguuccuu cuucggaggc uucuuccuua uucuuuucuu cgg     53

<210> SEQ ID NO 44
<211> LENGTH: 45
<212> TYPE: DNA
<213> ORGANISM: Artificial Sequence
<220> FEATURE:
```

```
<223> OTHER INFORMATION: 45mer circle

<400> SEQUENCE: 44
ttatttagac ttaaataagt tcctcaacat ccttcgatgg agccc              45

<210> SEQ ID NO 45
<211> LENGTH: 45
<212> TYPE: RNA
<213> ORGANISM: Artificial Sequence
<220> FEATURE:
<223> OTHER INFORMATION: hairpin RNA multimer which binds HIV-1 rev
      protein

<400> SEQUENCE: 45
ucuaaauaag ggcuccaucg aaggauguug aggaacuuau uuaag              45

<210> SEQ ID NO 46
<211> LENGTH: 49
<212> TYPE: DNA
<213> ORGANISM: Artificial Sequence
<220> FEATURE:
<223> OTHER INFORMATION: coding DNA circle

<400> SEQUENCE: 46
ttttgaacta gagttttcgg ctttcgcctc ttcagaaaag ccctctctc          49

<210> SEQ ID NO 47
<211> LENGTH: 49
<212> TYPE: RNA
<213> ORGANISM: Artificial Sequence
<220> FEATURE:
<223> OTHER INFORMATION: multimeric RNA transcript

<400> SEQUENCE: 47
gagggcuuuu cugaagaggc gaaagccgaa aacucuaguu caaaagaga         49

<210> SEQ ID NO 48
<211> LENGTH: 49
<212> TYPE: RNA
<213> ORGANISM: Artificial Sequence
<220> FEATURE:
<223> OTHER INFORMATION: momomeric ribozyme

<400> SEQUENCE: 48
aaaagagaga gggcuuuucu gaagaggcga agccgaaaa cucuaguuc          49

<210> SEQ ID NO 49
<211> LENGTH: 15
<212> TYPE: RNA
<213> ORGANISM: Homo sapiens

<400> SEQUENCE: 49
agaguucaaa agccc                                              15

<210> SEQ ID NO 50
<211> LENGTH: 49
<212> TYPE: RNA
<213> ORGANISM: Artificial Sequence
<220> FEATURE:
<223> OTHER INFORMATION: monomeric ribozyme

<400> SEQUENCE: 50
aaaagagaga gggcuuuucu gaagaggcga agccgaaaa cucuaguuc          49

<210> SEQ ID NO 51
```

<211> LENGTH: 83
<212> TYPE: DNA
<213> ORGANISM: Artificial Sequence
<220> FEATURE:
<223> OTHER INFORMATION: AS83 DNA nanocircle

<400> SEQUENCE: 51
gttccgactt ccgactctg agtttcgact tgtgagagaa ggatctcttg atcacttcgt      60
ctcttcaggg aaagatggga gat                                             83

<210> SEQ ID NO 52
<211> LENGTH: 83
<212> TYPE: DNA
<213> ORGANISM: Artificial Sequence
<220> FEATURE:
<223> OTHER INFORMATION: H83 nanocircle

<400> SEQUENCE: 52
gttccgagtt ttggaccgtt ggtttcgact tgtgagagaa ggatctcttg atcacttcgt      60
ctcttcagca aaatatggga gat                                             83

<210> SEQ ID NO 53
<211> LENGTH: 10
<212> TYPE: RNA
<213> ORGANISM: Artificial Sequence
<220> FEATURE:
<223> OTHER INFORMATION: Sequence of the catalytic H83 transcription
      product

<400> SEQUENCE: 53
cgguccaaaa                                                            10

<210> SEQ ID NO 54
<211> LENGTH: 25
<212> TYPE: RNA
<213> ORGANISM: Artificial Sequence
<220> FEATURE:
<223> OTHER INFORMATION: Sequence of the catalytic H83 transcription
      product

<400> SEQUENCE: 54
uuuugcugaa gagacgucga aacaa                                           25

<210> SEQ ID NO 55
<211> LENGTH: 83
<212> TYPE: DNA
<213> ORGANISM: Artificial Sequence
<220> FEATURE:
<223> OTHER INFORMATION: Sequence of the synthetic non-autolytic AH83
      chimera

<400> SEQUENCE: 55
gttccgactt tccgactgtt ggtttcgact tgtgagagaa ggatctcttg atcacttcgt      60
ctcttcagca aaatatggga gat                                             83

<210> SEQ ID NO 56
<211> LENGTH: 10
<212> TYPE: RNA
<213> ORGANISM: Artificial Sequence
<220> FEATURE:
<223> OTHER INFORMATION: Sequence of catalytic AH83 transcription
      product

<400> SEQUENCE: 56
cagucggaaa                                                            10

<210> SEQ ID NO 57
<211> LENGTH: 25
<212> TYPE: RNA
<213> ORGANISM: Artificial Sequence
<220> FEATURE:
<223> OTHER INFORMATION: Sequence of catalytic AH83 transcription
      product

<400> SEQUENCE: 57
uuuugcugaa gagacgucga aacca                                            25

<210> SEQ ID NO 58
<211> LENGTH: 83
<212> TYPE: RNA
<213> ORGANISM: Artificial Sequence
<220> FEATURE:
<223> OTHER INFORMATION: hammerhead-motif RNAs

<400> SEQUENCE: 58
cuucucucac aagucgaaac ucagagucgg aaagucggaa caucucccau cuuucccuga      60
agagacgaag ugaucaagag auc                                             83

<210> SEQ ID NO 59
<211> LENGTH: 83
<212> TYPE: RNA
<213> ORGANISM: Artificial Sequence
<220> FEATURE:
<223> OTHER INFORMATION: oligoribonucleotide monomer

<400> SEQUENCE: 59
ggaaagucgg aacaucuccc aucuuucccu gaagagacga agugaucaag agauccuucu      60
cucacaaguc gaaacucaga guc                                             83

<210> SEQ ID NO 60
<211> LENGTH: 73
<212> TYPE: DNA
<213> ORGANISM: Artificial Sequence
<220> FEATURE:
<223> OTHER INFORMATION: nanocircle vector

<400> SEQUENCE: 60
gaaaactgga ctacagggag gtaccaggta atgtaccaca acgtgtgttt ctctggtctg      60
cttctcagga atc                                                        73

<210> SEQ ID NO 61
<211> LENGTH: 73
<212> TYPE: RNA
<213> ORGANISM: Artificial Sequence
<220> FEATURE:
<223> OTHER INFORMATION: circular monomer

<400> SEQUENCE: 61
gauuccugag aagcagacca gagaaacaca cguuguggua cauuaccugg uaccucccug      60
uaguccaguu uuc                                                        73

<210> SEQ ID NO 62
<211> LENGTH: 41
<212> TYPE: DNA
<213> ORGANISM: Artificial Sequence
<220> FEATURE:
<223> OTHER INFORMATION: 41mer

<400> SEQUENCE: 62

```
gagatgttcc gactttccga ctctgagttt cgacttgtga g                    41

<210> SEQ ID NO 63
<211> LENGTH: 42
<212> TYPE: DNA
<213> ORGANISM: Artificial Sequence
<220> FEATURE:
<223> OTHER INFORMATION: 42mer

<400> SEQUENCE: 63
agaaggatct cttgatcact tcgtctcttc agggaaagat gg                   42

<210> SEQ ID NO 64
<211> LENGTH: 30
<212> TYPE: DNA
<213> ORGANISM: Artificial Sequence
<220> FEATURE:
<223> OTHER INFORMATION: splint oligonucleotide

<400> SEQUENCE: 64
aagtcggaac atctcccatc tttccctgaa                                 30

<210> SEQ ID NO 65
<211> LENGTH: 30
<212> TYPE: DNA
<213> ORGANISM: Artificial Sequence
<220> FEATURE:
<223> OTHER INFORMATION: splint

<400> SEQUENCE: 65
tcaagagatc cttctctcac aagtcgaaac                                 30

<210> SEQ ID NO 66
<211> LENGTH: 83
<212> TYPE: RNA
<213> ORGANISM: Artificial Sequence
<220> FEATURE:
<223> OTHER INFORMATION: monomeric sequence

<400> SEQUENCE: 66
ggaaagucgg aacaucuccc aucuuucccu gaagagacga agugaucaag agauccuucu   60
cucacaaguc gaaacucaga guc                                        83

<210> SEQ ID NO 67
<211> LENGTH: 83
<212> TYPE: RNA
<213> ORGANISM: Artificial Sequence
<220> FEATURE:
<223> OTHER INFORMATION: monomeric sequence

<400> SEQUENCE: 67
caaaacucgg aacaucuccc auauuuugcu gaagagacga agugaucaag agauccuucu   60
cucacaaguc gaaaccaacg guc                                        83

<210> SEQ ID NO 68
<211> LENGTH: 16
<212> TYPE: RNA
<213> ORGANISM: Artificial Sequence
<220> FEATURE:
<223> OTHER INFORMATION: nucleotides 1752-1767 from HIV-1 gag

<400> SEQUENCE: 68
uuguuggucc aaaaug                                                16
```

<210> SEQ ID NO 69
<211> LENGTH: 15
<212> TYPE: RNA
<213> ORGANISM: Artificial Sequence
<220> FEATURE:
<223> OTHER INFORMATION: short RNA sequence from (+) ASBV

<400> SEQUENCE: 69
ucugagucgg aaagg                                                      15

<210> SEQ ID NO 70
<211> LENGTH: 38
<212> TYPE: DNA
<213> ORGANISM: Artificial Sequence
<220> FEATURE:
<223> OTHER INFORMATION: oligonucleotide

<400> SEQUENCE: 70
cgaaaactgg actacaggga ggtaccaggt aatgtacc                             38

<210> SEQ ID NO 71
<211> LENGTH: 35
<212> TYPE: DNA
<213> ORGANISM: Artificial Sequence
<220> FEATURE:
<223> OTHER INFORMATION: oligonucleotide

<400> SEQUENCE: 71
acaacgtgtg tttctctggt ctgcttctca ggaat                                35

<210> SEQ ID NO 72
<211> LENGTH: 14
<212> TYPE: RNA
<213> ORGANISM: Artificial Sequence
<220> FEATURE:
<223> OTHER INFORMATION: sequence in HIV-1 pol gene

<400> SEQUENCE: 72
cuguagucca ggaa                                                       14

<210> SEQ ID NO 73
<211> LENGTH: 40
<212> TYPE: DNA
<213> ORGANISM: Artificial Sequence
<220> FEATURE:
<223> OTHER INFORMATION: oligonucleotide

<400> SEQUENCE: 73
ttgcccacac cgacggcgcc caccaggaaa gaagaaagga                           40

<210> SEQ ID NO 74
<211> LENGTH: 24
<212> TYPE: DNA
<213> ORGANISM: Artificial Sequence
<220> FEATURE:
<223> OTHER INFORMATION: oligonucleotide

<400> SEQUENCE: 74
ttgcccacac cgacggcgcc cacc                                            24

<210> SEQ ID NO 75
<211> LENGTH: 16
<212> TYPE: DNA
<213> ORGANISM: Artificial Sequence
<220> FEATURE:
<223> OTHER INFORMATION: oligonucleotide

```
<400> SEQUENCE: 75
aggaaagaag aaagga                                               16

<210> SEQ ID NO 76
<211> LENGTH: 16
<212> TYPE: DNA
<213> ORGANISM: Artificial Sequence
<220> FEATURE:
<223> OTHER INFORMATION: region of H21 DNA circle

<400> SEQUENCE: 76
tcctttcttc tttcct                                               16

<210> SEQ ID NO 77
<211> LENGTH: 42
<212> TYPE: DNA
<213> ORGANISM: Artificial Sequence
<220> FEATURE:
<223> OTHER INFORMATION: H21 DNA circle

<400> SEQUENCE: 77
ttctttcctt cgattccttt cttctttcct tcgattcctt tc                  42

<210> SEQ ID NO 78
<211> LENGTH: 39
<212> TYPE: RNA
<213> ORGANISM: Artificial Sequence
<220> FEATURE:
<221> NAME/KEY: modified base
<222> LOCATION: 1
<223> OTHER INFORMATION: biotinylatid uracil <223> oligonucleotide

<400> SEQUENCE: 78
ugcccacacc gacggcgccc accaggaaag aagaaagga                      39

<210> SEQ ID NO 79
<211> LENGTH: 31
<212> TYPE: RNA
<213> ORGANISM: Artificial Sequence
<220> FEATURE:
<223> OTHER INFORMATION: RNA sequence containing the Rev Responge
      Element

<400> SEQUENCE: 79 ggugggcgg guguucgcac cacgguacac c                               31

<210> SEQ ID NO 80
<211> LENGTH: 47
<212> TYPE: DNA
<213> ORGANISM: Artificial Sequence
<220> FEATURE:
<223> OTHER INFORMATION: probe-primer
<223> OTHER INFORMATION: bases 1-31 are RNA, bases 32-47 are DNA

<400> SEQUENCE: 80 ggugggcgg guguucgcac cacgguacac caggaaagaa gaaagga              47

<210> SEQ ID NO 81
<211> LENGTH: 15
<212> TYPE: DNA
<213> ORGANISM: Artificial Sequence
<220> FEATURE:
<223> OTHER INFORMATION: DNA sequence that binds thrombin

<400> SEQUENCE: 81
```

-continued

```
<210> SEQ ID NO 82
<211> LENGTH: 16
<212> TYPE: DNA
<213> ORGANISM: Artificial Sequence
<220> FEATURE:
<223> OTHER INFORMATION: primer

<400> SEQUENCE: 82
aggaaagaag aaagga                                              16

<210> SEQ ID NO 83
<211> LENGTH: 31
<212> TYPE: DNA
<213> ORGANISM: Artificial Sequence
<220> FEATURE:
<223> OTHER INFORMATION: probe-primer

<400> SEQUENCE: 83
ggttggtgtg gttggaggaa agaagaaagg a                             31
```

HIGHLY SENSITIVE MULTIMERIC NUCLEIC ACID PROBES

This is a continuation-in-part application of U.S. patent application Ser. No. 08/805,631, filed Feb. 26, 1997, and U.S. patent application Ser. No. 08/393,439, filed Feb. 23, 1995 (now U.S. Pat. No. 5,714,320, issued Feb. 3, 1998), which is a continuation-in-part application of Ser. No. 08/047,860, filed Apr. 15, 1993, now abandoned, all of which are incorporated herein by reference.

FIELD OF THE INVENTION

The present invention provides detectably labeled multimeric nucleic acids for use in molecular biology, chemistry, and biotechnology. The detectably labeled nucleic acids are especially useful as probes in molecular hybridization reactions.

BACKGROUND OF THE INVENTION

In recent years the availability of automated DNA synthesizers has revolutionized the fields of molecular biology and biochemistry. As a result, linear DNA oligonucleotides of specific sequences are available commercially from several companies. Commonly, oligonucleotides are labeled after synthesis to facilitate detection and quantification of oligonucleotide-target complexes. Oligonucleotides (labeled or unlabeled) can be used for a variety of applications. For example, DNA oligonucleotides can be used as primers for cDNA synthesis, as primers for the polymerase chain reaction (PCR), as templates for RNA transcription, as linkers for plasmid construction, and as hybridization probes for research and diagnostics.

Synthesis of oligonucleotides using standard solid-phase synthetic methods is, however, expensive. Reasons for this include the high costs of the synthetically modified monomers, e.g., phosphoramidite monomers, and the fact that up to a tenfold excess of monomer is used at each step of the synthesis, with the excess being discarded. Costs of DNA oligonucleotides have been estimated at $2–5 per base for one micromole (about 3 mg of a 10 mer) on the wholesale level. On this basis, 1 gram of a 20-base oligomer would cost on the order of $20,000.

Enzymatic methods for oligonucleotide synthesis use DNA or RNA nucleotide triphosphates (dNTPs or NTPs) derived from natural sources as the building blocks and have the potential for lowering the cost of oligonucleotide synthesis. These monomers are readily available, and are less expensive to produce than phosphoramidite monomers because the synthesis of nucleotide triphosphates from base monophosphates requires as little as one step. See, for example, E. S. Simon et al., *J. Org. Chem.*, 55, 1834 (1990). Nucleotide triphosphates (NTPs) can also be prepared enzymatically. The polymerase enzymes used in these methods are efficient catalysts, and are readily available.

The two primary methods currently used for enzymatic synthesis of DNA are cloning (e.g., J. Sambrook et al., *Molecular Cloning;* 2nd ed.; Cold Spring Harbor Press, 1989) and the polymerase chain reaction (e.g., R. K. Saiki et al., *Science,* 239, 487 (1988)). Cloning requires the insertion of a double-stranded version of the desired sequence into a plasmid, followed by transformation of a bacterium, growth, plasmid re-isolation, and excision of the desired DNA by restriction endonucleases. This method is not feasible for large-scale preparation of oligonucleotides because most of the material produced (the vector) is in the form of unusable DNA sequences.

Polymerase chain reaction (PCR) is a newer technique that uses a thermostable polymerase to copy duplex sequences using primers complementary to the DNA. Subsequent heating and cooling cycles accomplish the efficient amplification of the original sequence. However, for short oligomers, such as those used in anti-sense applications (e.g., less than about 50 nucleotides), PCR is inefficient and not cost-effective because it requires stoichiometric amounts of primer; i.e., a primer for every new strand being synthesized.

Recently, a method was developed for the enzymatic synthesis of DNA oligomers using a noncleavable linear hairpin-shaped template/primer in a PCR-like enzymatic synthesis. See G. T. Walker et al., *PNAS,* 89, 392 (1992). Although this method may be more cost-effective than PCR, the polymerase must still dissociate from the template to enable amplification. Furthermore, the end groups of the DNA produced are ragged and not well-defined.

Other methods of DNA replication are discussed in Harshey et al., *Proc. Nat'l. Acad. Sci., USA,* 78, 1090 (1985); and Watson, *Molecular Biology of the Gene* (3rd Edition). Harshey et al. discuss the theoretical method of "roll-in" replication of double-stranded, large, circular DNA. The "roll-in" process involves small, double-stranded circle cleavage and incorporation into a genome. It is primarily a process for inserting double-stranded plasmids into a double-stranded genome. Although one could conceivably use an entire genome to replicate an oligonucleotide, the resulting product would be thousands of nucleotides longer than desired. Thus, the "roll-in" process would be a very inefficient means to produce target oligonucleotide sequences. Watson briefly mentions the replication of single-stranded circles, but the author focuses on the replication of double-stranded circles.

Known methods for processive rolling-circle synthesis of DNA involve the extension of an oligonucleotide primer hybridized to a double-stranded circular polynucleotide template. Prior to the present invention, it was believed by those skilled in the art that processive rolling-circle synthesis would not proceed without additional proteins which unwind the duplex ahead of the polymerase. See, e.g. Eisenberg et al., *PNAS USA,* 73:3151 (1976); *The Single-Stranded DNA Phages,* D. T. Denhardt et al., eds., Cold Spring Harbor Press; Cold Spring Harbor (1978); and DNA Replication, W. H. Freeman, San Francisco, 1980. In Eisenberg et al., the in vitro replication of φX174 DNA using purified proteins is disclosed. Among the listed necessary proteins are DNA unwinding protein (also known as SSB, single-strand binding protein), cisA protein, and rep protein. These DNA unwinding proteins (which also require ATP) are necessary for this replicative synthesis; otherwise the polymerase stalls.

*The Single-Stranded DNA Phages* (D. T. Denhardt et al., eds., Cold Spring Harbor Press; Cold Spring Harbor (1978)) includes a discussion of the mechanism of replication of a single-stranded phage. An early stage of replication involves the elongation of a single-stranded (−) template annealed to a full-length linear (+) strand. Further elongation reportedly requires unwinding of the helix ahead of the polymerase. DBP (double-strand binding protein) was believed to be necessary to coat the displaced strand in order for there to be successful DNA synthesis during elongation.

Enzymatic synthesis of DNA requires the use of an effective polymerase. For example, the polymerase from phage φ29 is known to amplify DNA strands as large as 70 kb in length and exhibits a high degree of processivity.

However, the use of phage φ29 polymerase to amplify a selected oligonucleotide present as part of a typical plasmid vector still results in the wasteful (in both time and monetary resources) production of unwanted DNA sequences. Additionally, after amplification is complete, the investigator must separate the strands, cleave the product, and purify the oligonucleotide of interest from thousands of other unwanted base pairs.

RNA oligomers are currently synthesized by two principal methods: automated chemical synthesis and enzymatic runoff transcription. An automated synthesizer can be used to construct RNA oligomers using a modification of the phosphoramidite approach. See, for example, S. A. Scaringe et al., *Nucleic Acids Res.*, 18, 5433 (1990). Chemical synthesis of RNAs has the advantage of allowing the incorporation of nonnatural nucleosides, but the yield decreases significantly as the length of the RNA product increases. Stepwise yields of only 97.5% per round of synthesis are typical. Moreover, because of the need for additional protecting groups, RNA phosphoramidite monomers are considerably more expensive than DNA phosphoramidite monomers, rendering RNA synthesis by this method extremely costly.

An alternative, the enzymatic runoff transcription method, utilizes a single or double-stranded DNA template for RNA synthesis. Runoff transcription requires a phage polymerase promoter, thus a DNA strand approximately 20 nucleotides longer than the desired RNA oligomer must be synthesized. There are also strong sequence preferences for the RNA 5' end (J. F. Milligan et al., *Nucleic Acids Res.*, 15, 8783–8798 (1987)). In runoff transcription the RNA copy begins to form on the template after the phage polymerase promoter and runs until the end of the template is reached. This method has the disadvantages of producing RNA oligomers with ragged, ill-defined end groups and giving relatively slow amplification. Both chemical synthesis and runoff transcription produce a number of undesired products shorter or longer than the desired RNA, lowering effective yields and requiring careful purification.

Self-processing of nucleic acids can generate polynucleotides with well-defined ends. For example, double-stranded DNA plasmid vectors can be constructed to encode ribozymes as well as their associated self-cleavage sites, leading to self-processing after transcription (A. M Dzianott et al., *Proc. Natl. Acad. Sci. USA*, 86, 4823–4827 (1989); C. A. Grosshans et al., *Nucleic Acids Res.*, 19, 3875–3880 (1991); K. Taira et al., *Nucleic Acids Res.*, 19 5125–5130 (1991)). However, conventional plasmid vectors are highly inefficient templates for preparative, in vitro ribozyme synthesis because they generate significantly longer RNAs than desired. Their large size poses additional problems for delivery into cells in cases where transcription is to be performed intracellularly. Plasmid vectors also require promoters to initiate transcription.

Currently, multimeric oligonucleotides are typically synthesized by end-to-end ligation of members of a homogenous population of oligonucleotides produced by one of the above-described methods. This method results in the synthesis of complementary multimers as well, yielding double-stranded, but not single-stranded, multimeric products.

There exists a continuing need for less expensive, faster, and more efficient methods for the large-scale production of DNA and RNA oligomers and multimers, particularly single-stranded oligomers and multimers. For example, potential therapeutic applications require large amounts (tens or hundreds of grams) of well-characterized oligomers for animal and clinical trials, and even more for eventual use as pharmaceuticals. See, for example, I. Kitajima et al., *Science,* 258, 1792 (1992), and M. Z. Ratajczak et al., *PNAS,* 89, 11823 (1992). For medical and diagnostic applications involving the use of labeled oligonucleotides, a particularly useful method would allow for concurrent incorporation of the label during oligonucleotide synthesis.

SUMMARY OF THE INVENTION

The present invention provides a detectably labeled DNA or RNA oligonucleotide multimer. The oligonucleotide multimers of the invention are useful, for example, as probes and diagnostic and/or therapeutic agents. The oligonucleotide multimer contains multiple contiguous copies of a repeated oligonucleotide. In a preferred embodiment, the detectable label is incorporated into the oligonucleotide multimer as part of the repeated oligonucleotide. Thus, at least one copy or unit of the repeated oligonucleotide of the oligonucleotide multimer contains at least one copy of the detectable label. More preferably, the detectably labeled oligonucleotide multimer contains multiple copies of the detectable label.

The detectable label may be either covalently or noncovalently attached to the detectably labeled oligonucleotide multimer. Noncovalent labeling can be achieved by hybridizing to the oligonucleotide multimer a separate labeling oligonucleotide that contains at least one copy of the detectable label. The labeling oligonucleotide has a nucleotide sequence complementary to at least a portion of the nucleotide sequence of the repeated oligonucleotide of the oligonucleotide multimer.

In a preferred embodiment, the detectably labeled oligonucleotide multimer contains a binding region that binds a target molecule, preferably a target DNA or RNA molecule. The binding region can be present in a nonrepeated 5' end of the detectably labeled oligonucleotide multimer, as when a detectably labeled oligonucleotide of the invention is subsequently conjugated with a binding moiety, or when synthesis of the detectably labeled oligonucleotide multimer is initiated with an oligonucleotide primer containing a binding region in its 5' end. Alternatively, the binding region can constitute a portion of the repeated oligonucleotide sequence. In the latter case, the detectably labeled oligonucleotide multimer will contain multiple copies of the binding region.

The present invention also provides a method for the synthesis of oligonucleotides, preferably detectably labeled oligonucleotide multimers, using a small, single-stranded circular oligonucleotide template. The synthetic method of the invention, referred to herein as the "rolling circle" method, allows for the synthesis of single-stranded multimers comprising multiple copies of an oligonucleotide complementary to a circular template. An effective amount of a single-stranded circular oligonucleotide template is combined with an effective amount of at least two types of nucleotide triphosphate and an effective amount of a polymerase enzyme, without the addition of auxiliary proteins, to form the oligonucleotide multimer.

DNA synthesis according to the method of the invention includes the addition of an oligonucleotide primer to the reaction mixture to initiate nucleic acid synthesis. The circular template used in DNA synthesis therefore contains a nucleotide sequence at least partially complementary to the oligonucleotide primer. The primer hybridizes to the circular template, after which primer extension can occur to produce the DNA oligonucleotide multimer.

In RNA synthesis, the use of an oligonucleotide primer to initiate synthesis of the oligonucleotide multimer product is not necessary, and the circular template preferably lacks a primer-binding site and a promoter sequence.

The single-stranded circular template is complementary to the nucleotide sequence of a selected oligonucleotide or oligonucleotide multimer. The circular template can contain one or more copies of the complementary sequence. It may be constructed of DNA or RNA or analogs thereof. Preferably, the circular template is constructed of DNA. The circular template can contain about 15–1500 nucleotides, preferably about 24–500 nucleotides and most preferably about 30–150 nucleotides. The nucleotide sequence of the selected oligonucleotide can be a sense, antisense, or any other nucleotide sequence, including a random sequence.

The polymerase enzyme can be selected from any enzyme that effects the synthesis of the multimer. For the synthesis of RNA oligomers, the polymerase enzyme is preferably selected from the group consisting of T7 RNA Polymerase, T4 RNA Polymerase, SP6 RNA Polymerase, RNA Polymerase II, RNA Polymerase III, T3 RNA Polymerase and E. coli RNA Polymerase. Closely homologous mutants of the enzymes above, i.e., mutants with greater than about 80% homology, can also be employed. It is not necessary to include an RNA Polymerase promoter sequence on the circular oligonucleotide template; rather, the method is preferably carried out using a circular template that lacks a canonical RNA polymerase promoter sequence.

For the synthesis of DNA oligomers the polymerase enzyme is preferably selected from the group consisting of DNA Polymerase I, Klenow fragment of DNA Polymerase I, T4 DNA Polymerase, T7 DNA Polymerase, Taq Polymerase, AMV Reverse Transcriptase. More preferably, the polymerase enzyme is the Klenow fragment of DNA Polymerase I.

In the present method for synthesizing a detectably labeled DNA oligonucleotide multimer, an effective amount of an oligonucleotide primer is annealed to a single-stranded circular template to yield a primed circular template, wherein the single-stranded circular template contains at least one copy of a nucleotide sequence complementary to the oligonucleotide sequence to be repeated in the oligonucleotide multimer. In a preferred method, a detectably labeled RNA oligonucleotide multimer is synthesized, and the use of an oligonucleotide primer during synthesis is not required. The circular template (primed circular template in the case of DNA synthesis) is combined with (i) an effective amount of at least two types of nucleotide triphosphates, wherein at least one type of nucleotide triphosphate comprises the detectable label, and (ii) an effective amount of a polymerase enzyme to yield the detectably labeled oligonucleotide multimer. The detectable label can be incorporated at one or more predetermined sites on the repeated oligonucleotide, in accordance with the nucleotide sequence of the circular oligonucleotide template.

The present method further provides a method for detecting a target molecule that involves contacting the detectably labeled oligonucleotide multimer with a sample suspected of containing the target molecule so as to yield a detectably labeled bound multimer-target complex, followed by detection of the bound multimer-target complex.

DETAILED DESCRIPTION OF THE INVENTION

Figure 1:
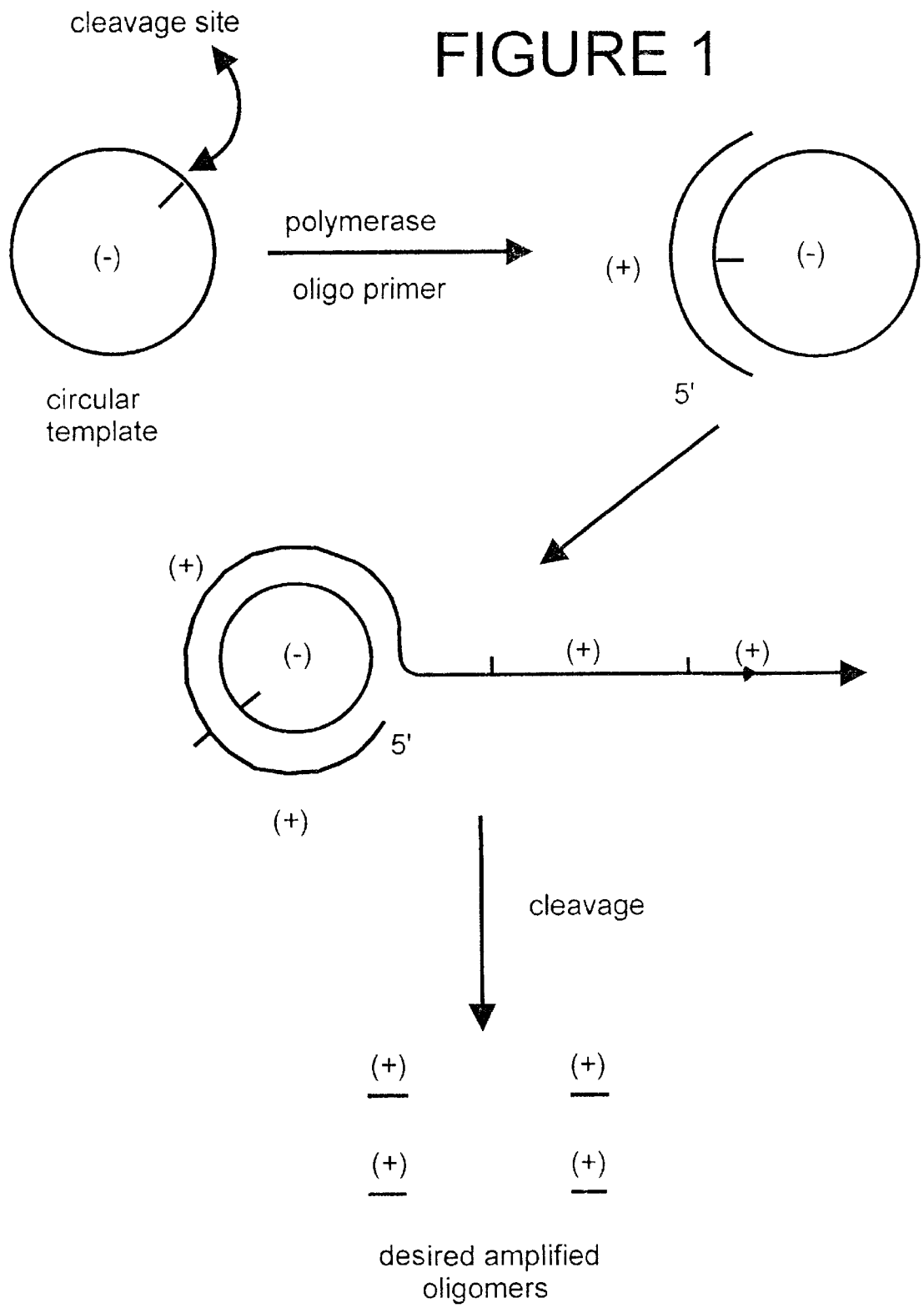
FIG. 1. Schematic of the rolling circle synthetic method of the present invention.
Figure 2:
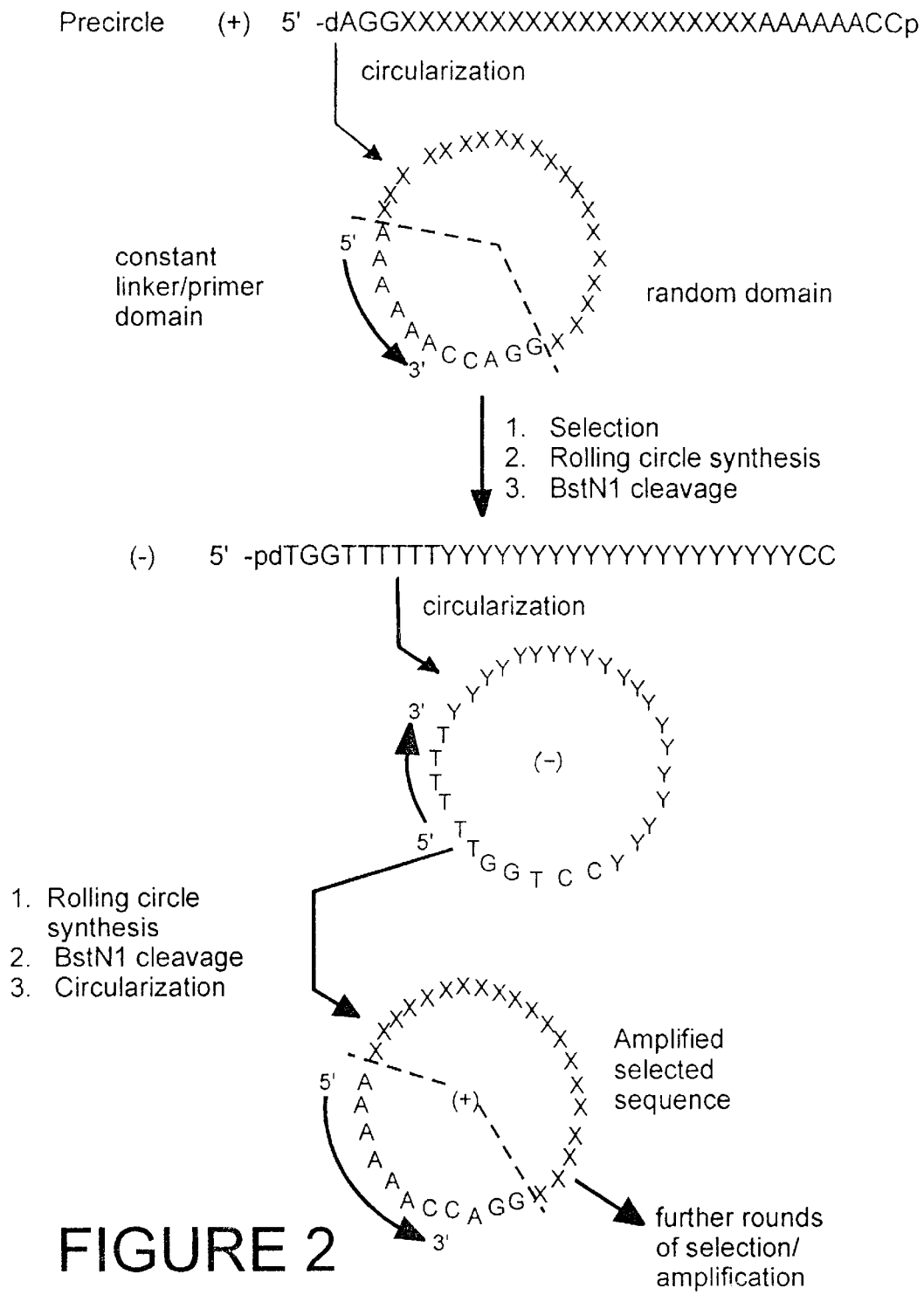
FIG. 2. Schematic of the selection and amplification of a circular oligomer (SEQ ID NO:23), (SEQ ID NO:24), (SEQ ID NO:25), AND (SEQ ID NO:26).
Figure 3:
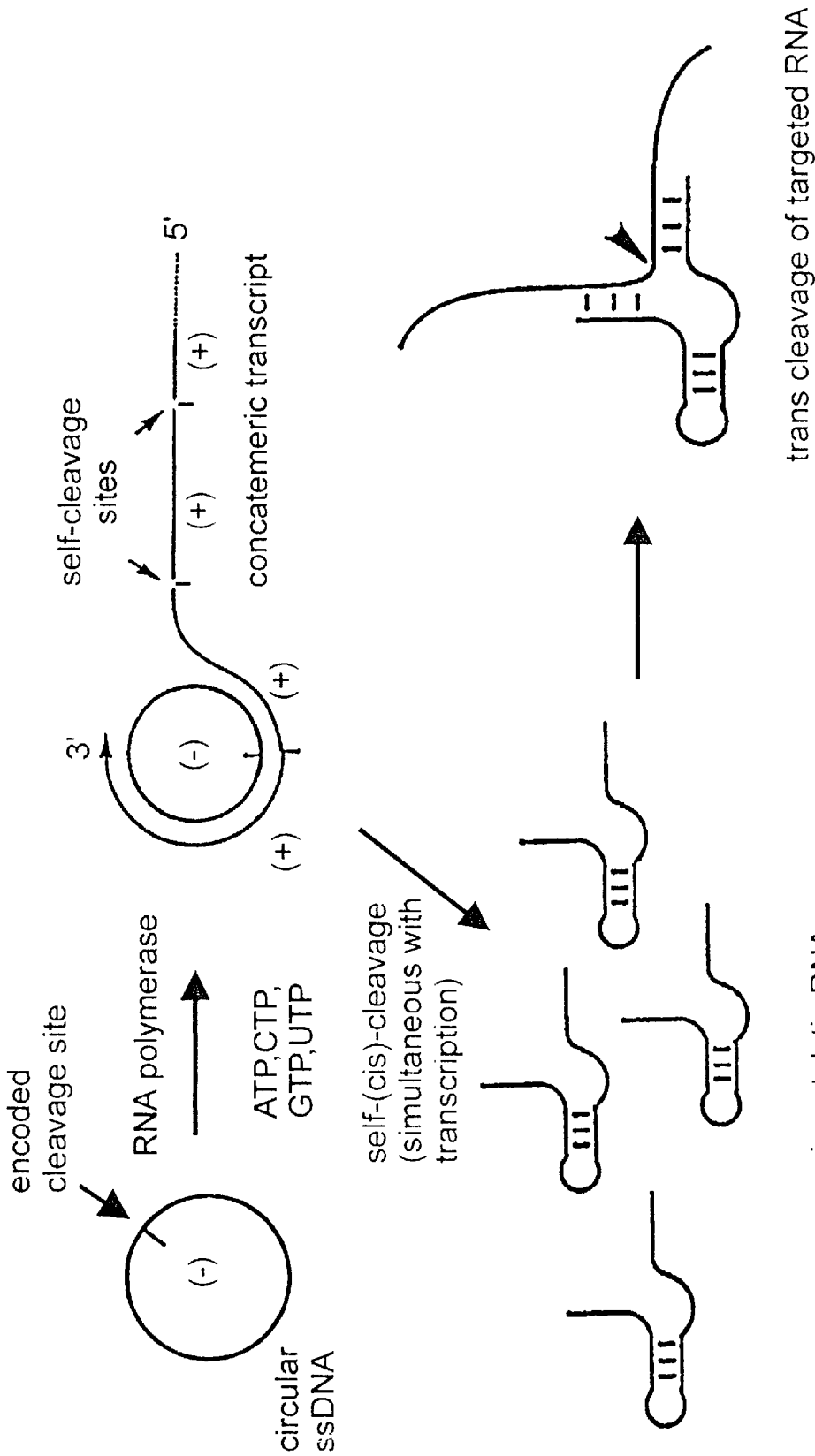
FIG. 3. Scheme for rolling transcription of a synthetic nanocircle vector encoding a catalytic RNA-cleaving domain and its own substrate; concatemers self-process to monomeric RNAs having the length of the circle.

As used herein, "oligonucleotide" or "oligomer" refers to a sequence-defined and length-defined nucleic acid or analog thereof, whereas a "multimer" is a repeated linear nucleic acid polymer containing a plurality or multiplicity of copies of an oligomer joined end to end. A multimer is also referred to herein as a "concatemer".

An "isolated circular template" refers to a circular nucleic acid sequence containing one or more copies of a sequence complementary to the sequence of a desired oligomer. It is formed by circularization of a linear oligonucleotide strand referred to as a "precircle".

An "isolated oligonucleotide primer" refers to a nucleic acid having a sequence that is sufficiently complementary to a nucleic acid sequence of the circular template to bind to the isolated circular template and act as a site for initiation of synthesis of a multimer.

A "sense" sequence refers to a DNA or RNA sequence that encodes the information for a protein product. An "antisense" sequence refers to a DNA or RNA sequence complementary to a sense sequence that can bind to a sense sequence and inhibit its replication or transcription.

An "effective" amount refers to an amount of a component effective in the present method to produce multimers longer than the circular template, preferably about 4–4000 times the linear length of the circular template. For example, in DNA synthesis an effective amount of the primer is about 0.1–100 moles per mole of circular template, and an effective amount of nucleotide triphosphates is about $50\text{-}10^7$, more preferably $200\text{-}2\times10^6$, moles per mole of circular template.

The terms DNA and RNA should be understood to include not only naturally occurring nucleic acids, but also sequences containing nucleotide analogs or modified nucleotides, such as those that have been chemically or enzymatically modified.

The present invention provides a novel, inexpensive, and simple method for the enzymatic construction of DNA and RNA oligonucleotides, oligonucleotide multimers, and analogs thereof, having a specified sequence and well-defined ends. This synthetic method has several advantages over presently used techniques. First, the cost of oligomers produced by this method is lower than that of machine-synthesized or PCR-generated oligomers. Previous methods of amplifying a target nucleic acid sequence by circular replication methods used plasmid-sized DNA several thousand nucleotides in length. These previous amplification methods necessarily produced sequences thousands of nucleotides in length, even when the sequence of interest may only have been a few dozen nucleotides long. Thus, these amplification reactions consume a large quantity of nucleotides while only a comparatively small number of these nucleotides actually were components in the desired product.

Second, the method of the present invention is very simple and produces relatively pure oligomers. Because the method of the present invention does not incorporate unwanted nucleotides into the product molecules, the resulting oligonucleotides are easier to purify than those oligomers resulting from the prior art methods of replication. Third, the method does not consume costly organic solvents or other reagents, nor does it generate costly organic waste.

The synthetic method of the present invention advantageously uses readily available enzymes and a chemically prepared template to generate large amounts of a complementary oligonucleotide sequence. The method is advantageous because it uses only a small excess of nucleotide triphosphates, with the unused portions being recycled. The direct product of the reaction is reasonably pure, and can be further purified very easily using standard techniques, if desired. The synthesis of RNA oligonucleotide requires no primer, and the synthesis of DNA oligonucleotide requires only substoichiometric amounts of primer. The oligomers produced by the method of the invention have, after cleavage, well-defined ends.

This synthetic method is ideal for the large-scale preparation of desirable oligomers or multimers of DNA or RNA, such as the commercially available hybridization primers, PCR primers, ribozymes, molecular probes, or any oligonucleotide that has been (or may be) shown to be of therapeutic value.

The present synthetic method is advantageous for many reasons including the following: (1) it allows optimum production of single-stranded oligonucleotides, unlike PCR and cloning; (2) it uses lower excesses of nucleotide units in the synthesis as compared to DNA synthesizers; (3) it requires only a catalytic amount of circular template and, optionally, primer (PCR to produce DNA oligomers requires stoichiometric amounts of primer); (4) it produces cleaved oligomers having clean, well-defined ends (unlike runoff transcription); (5) it is more efficient than single-stranded PCR amplification or runoff transcription because the polymerase enzyme is not required to associate and dissociate from the template in cycles; (6) expensive thermal cyclers and thermostable polymerases are not required; (7) it is possible to make DNA and RNA oligomers and analogs thereof by this method using the same templates; (8) it is better suited for synthesis of circular oligonucleotides; (9) it allows for production in very large batches (hundreds or thousands of grams); (10) it does not use organic solvents or potentially toxic reagents; (11) fewer errors in the sequences are made (machine-synthesized DNA contains structural errors about every 50–100 bases or so, whereas enzyme methods make errors at the rate of about 1 in $10^4$–$10^8$ bases); and (12) the product generally needs relatively little purification (gel filtration or dialysis is typically sufficient, if even needed at all) because only small amounts of template and polymerase are needed to produce large amounts of oligomer. Thus, the present invention reduces, and in certain situations completely eliminates, difficult and expensive large-scale chromatographic purification.

Particular advantages of the method of the invention over current methods for synthesizing repeating unit oligonucleotide multimers include (a) increased length of the multimeric product; (b) the ability to produce single-stranded multimers instead of only duplexes; and (c) the optional use of a primer to initiate synthesis, which can be constructed to carry a desired nonrepeating sequence.

The oligonucleotide products of the synthetic method may be either linear or circular. Circular oligomers have distinct advantages over linear oligomers. For example, circular DNA oligomers have a half-life of greater than about two days in human serum (as compared to a half-life of about twenty minutes for linear oligomers). See, for example, S. Rumney and E. Kool, *Angew. Chem., Intl. Ed. English,* 31, 1617 (1992).

Rolling Circle Synthesis of Oligonucleotides and Oligonucleotide Multimers

Overview. The method of the invention for the synthesis of DNA and RNA oligomers, and synthetically modified analogs thereof such as, for example, those containing DNA phosphorothioates, RNA phosphorothioates, 2'-O-methyl ribonucleotides, involves these general steps: (1) providing an effective amount of a single-stranded oligonucleotide circular template and, in the case of DNA synthesis, an effective amount of a single-stranded oligonucleotide primer; (2) in the case of DNA synthesis, annealing the oligonucleotide primer to the oligonucleotide circular template to form a primed circular template; (3) combining the circular template (the primed template in the case of DNA synthesis) with an effective amount of at least two types of nucleotide triphosphates and an effective amount of a polymerase enzyme so as to yield a single-stranded nucleotide multimer complementary to the circular oligonucleotide template; (4) optionally cleaving of the single-stranded nucleotide multimer into the desired single-stranded oligonucleotides, i.e., oligomers, and (5) optionally circularizing the oligonucleotide(s) to form circular oligonucleotide products.

The synthetic method can be performed in vitro, or inside a cultured prokaryotic or eukaryotic cell, preferably a bacterial cell.

The circular oligonucleotide template (sometimes referred to herein as a nanocircle, vector, or nanovector) used for DNA or RNA oligonucleotide synthesis is composed of a single nucleotide strand containing naturally occurring or modified nucleotides. Preferably, the circular template consists of DNA. The nucleotide sequence of the circular template is selected such that when the circular template is transcribed by a DNA or RNA polymerase, the desired DNA or RNA oligonucleotide will be produced.

It is notable that RNA synthesis requires no primer, and surprisingly there is no need for an RNA polymerase promoter sequence on the circular template. It is possible to use a primer for RNA synthesis according to the invention, but the synthetic reaction is preferably conducted in its absence. Similarly, an RNA promoter sequence may be present on the circular nanovector, but is preferably absent.

The present synthetic method requires only a very small amount of circular template, primer (for DNA synthesis), and polymerase enzyme, i.e., only an effective catalytic amount for each component. Surprisingly, no auxiliary proteins need to be added to assist the polymerase. A relatively larger amount, i.e., at least a stoichiometric amount, of the nucleotide triphosphates is required. After the reaction, the mixture consists of a large amount of the product oligomer and only small amounts of the template, primer, polymerase enzyme, and cleaving enzyme or reagent. Thus, the product is produced in relatively high purity, and may require only gel filtration or dialysis before use, depending on the application. Advantageously, the polymerase enzyme, the circular template, unreacted primer (in the case of DNA synthesis), and unreacted nucleotide triphosphates are recovered for further use.

Construction of circular template. A circular oligonucleotide template which is complementary in sequence to the desired oligonucleotide product can be prepared from a linear precursor, i.e., a linear precircle. The linear precircle preferably has a 3'- or 5'-phosphate group and can contain any desired DNA or RNA or analog thereof, some examples of which are set forth below in connection with the description of the rolling circle synthetic method. If the desired oligonucleotide product sequence is relatively short (i.e., less than about 20–30 bases), a double or higher multiple copy of the complementary sequence can advantageously be contained in the circular template. This is generally because enzymes cannot process circular sequences of too small a size. Typically, a circular template useful in the present method contains about 15–1500 nucleotides, preferably about 22–500, and more preferably about 24–150 nucleotides. It is to be understood that the nucleotide sequence of the desired oligonucleotide product can either be a sense, antisense, or any other preselected nucleotide sequence.

In the case of RNA synthesis, the circular oligonucleotide template is preferably constructed to contain a nucleotide sequence that encodes a biologically active RNA sequence, including but not limited to a catalytic RNA sequence, an antisense RNA sequence, or a "decoy" RNA sequence. The circular oligonucleotide template also preferably encodes a nucleotide or nucleotide sequence that renders the oligonucleotide multimer product cleavable. Where the oligonucleotide multimer product is RNA, cleavage of the multimer into a plurality of monomeric products is conveniently effected autolytically by designing the circular template to encode a ribozyme and its associated cleavage site. Where the oligonucleotide multimer product is DNA, cleavage can be effected, for example, by using a restriction enzyme; thus the oligonucleotide multimer can advantageously contain multiple copies of a restriction sequence encoded by the circular template. For example, the sequence 5'- . . . G A T C . . . -3' will be cleaved immediately before the G by the restriction enzyme Sau3AI. The product oligomers will thus contain the sequence on the 5' end. Alternately, a Type-II restriction site can be encoded within a hairpin forming sequence, so that the entire cleavable group will be removed by the cleaving enzyme, leaving only the desired sequence, as in Example 3. Another method, described by Szybalski et al., *Gene,* 40, 169 (1985), uses an added oligomer to direct a Type-II restriction enzyme to cleave at any desired sequence. A specific cleavable group might also be a natural DNA base, encoded by its complement in the circular template, which could be cleaved chemically, as in Examples 2 and 8, or it could be a modified base, as in Example 9 or 10.

Linear precircle oligonucleotides, from which the circular template oligonucleotides are prepared, can be made by any of a variety of procedures known for making DNA and RNA oligonucleotides. For example, the linear precircle can be synthesized by any of a variety of known techniques, such as enzymatic or chemical, including automated synthetic methods. Furthermore, the linear oligomers used as the template linear precircle can be synthesized by the rolling circle method of the present invention. Many linear oligonucleotides are available commercially, and can be phosphorylated on either end by any of a variety of techniques.

Linear precircle oligonucleotides can also be restriction endonuclease fragments derived from a naturally occurring DNA sequence. Briefly, DNA isolated from an organism can be digested with one or more restriction enzymes. The desired oligonucleotide sequence can be isolated and identified by standard methods as described in Sambrook et al., *A Laboratory Guide to Molecular Cloning,* Cold Spring Harbor, N.Y. (1989). The desired oligonucleotide sequence can contain a cleavable site, or a cleavable site can be added to the sequence by ligation to a synthetic linker sequence by standard methods.

Linear precircle oligonucleotides can be purified by polyacrylamide gel electrophoresis, or by any number of chromatographic methods, including gel filtration chromatography and high performance liquid chromatography. To confirm a nucleotide sequence, oligonucleotides can be subjected to RNA or DNA sequencing by any of the known procedures. This includes Maxam-Gilbert sequencing, Sanger sequencing, capillary electrophoresis sequencing, automated sequencing, wandering spot sequencing procedure, or by using selective chemical degradation of oligonucleotides bound to Hybond paper. Sequences of short oligonucleotides can also be analyzed, for example, by plasma desorption mass spectrometry, fast atom bombardment-mass spectrometry (FAB-MS) or electrospray ionization mass spectrometry (El-MS).

The present invention also provides several methods wherein the linear precircles are then ligated chemically or enzymatically end-to-end into circular form. This can be done using any standard techniques that result in the joining of two ends of the precircle. Such methods include, for example, chemical methods employing known coupling agents such as BrCN plus imidazole and a divalent metal, N-cyanoimidazole with $ZnCl_2$, 1-(3-dimethylaminopropyl)-3 ethylcarbodiimide HCl, and other carbodiimides and carbonyl diimidazoles. Furthermore, the ends of a precircle can be joined by condensing a 5'-phosphate and a 3'-hydroxyl, or a 5'-hydroxyl and a 3'-phosphate. Enzymatic circle closure is also possible using DNA ligase or RNA ligase under conditions appropriate for these enzymes.

One enzymatic approach utilizes T4 RNA ligase, which can couple single-stranded DNA or RNA. This method is described in D. C. Tessier et al., *Anal Biochem.,* 158, 171–178 (1986), which is incorporated herein by reference. Under high dilution, the enzyme ligates the two ends of an oligomer to form the desired circle. Alternatively, a DNA ligase can be used in conjunction with an adapter oligomer under high dilution conditions.

Preferably, the method of forming the circular oligonucleotide template involves adapter-directed coupling. Methods such as this are described in the Examples and in G. Prakash et al., *J. Am. Chem. Soc.*, 114, 3523–3527 (1992), E. T. Kool, PCT Publication WO 92/17484, and E. Kanaya et al., *Biochemistry*, 25, 7423–7430 (1986), which are incorporated herein by reference. This method includes the steps of: hybridizing a linear precursor having two ends to an adapter, i.e., a positioning oligonucleotide, to form an open oligonucleotide circle; joining the two ends of the open oligonucleotide circle to form the circular oligonucleotide template; and recovering the single-stranded circular oligonucleotide template. The positioning oligonucleotide is complementary to the two opposite ends of the linear precursor. The precursor and the adapter are mixed and annealed, thereby forming an open oligonucleotide circle in which the 5' and 3' ends of the precursor are adjacent. The adapter juxtaposes the two ends. This occurs preferentially under high dilution, i.e., no greater than about 100 micromolar, by using very low concentrations of adapter and precircle oligomers, or by slow addition of the adapter to the reaction mixture. Any suitable ligation chemistry can be used to join the ends of the linear precircle. For example, the ends can undergo a condensation reaction, wherein the 5'-phosphate is coupled to the 3'-hydroxyl group or the 3'-phosphate is coupled to the 5'-hydroxyl group, after about 6–48 hours of incubation at about 4–37° C. This occurs in a buffered aqueous solution containing divalent metal ions and BrCN at a pH of about 7.0. Preferably, the buffer is imidazole-HCl and the divalent metal is Ni, Zn, Mn, Co, Cu, Pb, Ca, or Mg. More preferably, the metals are Ni and Zn. Other coupling reagents that work include 1-(3-dimethylaminopropyl)-3 ethylcarbodiimide HCl, and other water-soluble carbodiimides, or any water-active peptide coupling reagent or esterification reagent.

The ends of the linear oligonucleotide precircle can alternatively be joined using a self-ligation reaction. In this method, the 5' end of the linear precircle is 5'-iodo- or 5'-tosyl- and the 3' end is 3'- phosphorothioate.

The circular oligonucleotide template can be purified by standard techniques, although this may be unnecessary. For example, if desired the circular oligonucleotide template can be separated from the end-joining group by denaturing gel electrophoresis or melting followed by gel electrophoresis, size selective chromatography, or other appropriate chromatographic or electrophoretic methods. The isolated circular oligonucleotide can be further purified by standard techniques as needed.

Oligonucleotide primer. An oligonucleotide primer is used to initiate rolling circle synthesis of DNA oligonucleotide multimers using the circular oligonucleotide template. The primer is generally short, preferably containing about 4–50 nucleotides, and more preferably about 6–12 nucleotides. Most preferably, the primer is 7–12 nucleotides and has a free 3'-OH group. This primer is substantially complementary to part of the circular template, preferably to the beginning of the desired oligomer sequence. A substantially complementary primer has no more than about 1–3 mismatches while still maintaining sufficient binding to the template. The 3' end of the primer must be at least about 80%, preferably 100%, complementary to the circular template. There is no requirement that the 5' end be complementary, as it would not be required to bind to the template. Although a portion of the primer does not have to bind to the circular template, at least about 4–12 nucleotides should be bound to provide for initiation of nucleic acid synthesis. The primer can be synthesized by any of the methods discussed above for the linear precircle oligomer, such as by standard solid-phase techniques. See, for example, S. L. Beaucage et al., *Tetrahedron Lett.*, 22 1859 (1981) (for DNA), and S. A. Scaringe et al., *Nucleic Acids Res.*, 18, 5433 (1990) (for RNA).

An effective amount of the primer is added to the buffered solution of an effective amount of the circular template under conditions to anneal the primer to the template. An effective amount of the primer is present at about 0.1–100 moles primer per mole of circular template, preferably 0.1–10 moles primer per mole of circular template. An effective amount of the circular template is that amount that provides for sufficient yield of the desired oligomer product. The effective amount of the circular template depends on the scale of the reaction, the size and sequence of circular template, and the efficiency of the specific rolling circle synthesis. Typically, the amount of the circular template is present at about a 1:5 to 1:20000 ratio to the amount of desired oligomer product, i.e., 1–5000 fold amplification, preferably a 1:50 to 1:5000 ratio.

Conditions that promote primer annealing are known to those of skill in the art for both DNA-DNA compositions and DNA-RNA compositions and are described in Sambrook et al., supra. Once formed, the primed circular template is used to initiate synthesis of the desired oligomer or multimer.

Rolling circle synthesis. Rolling circle synthesis is initiated when nucleotide triphosphates and polymerase are combined with a circular oligonucleotide template. In the case of DNA synthesis, a primed circular template is utilized. At least two types of nucleotide triphosphate, along with an effective catalytic amount of the desired polymerase enzyme are used in the synthetic reaction. In DNA synthesis, the polymerase starts at the primer, elongates it, and continues around the circle, making the nucleotide sequence of the desired oligonucleotide product. The polymerase continues past the starting point, proceeding many times around the circle.

The process is similar for RNA synthesis, except that the polymerase can initiate synthesis on the circular template in the absence of a canonical RNA promoter sequence and without the aid of a primer.

This amplified run-on synthesis produces a long single multimer strand which is made up of many end-to-end copies of the nucleotide sequence complementary to the circular template sequence. The multimer strand thus contains multiple copies of the desired oligonucleotide product.

The size of the multimer product can be about 60 to $5 \times 10^6$ nucleotides in length. The present method is capable of producing longer RNAs than other known synthetic methods, and results in higher yields. After cleavage, the RNA products produced by the present invention are more pure and have greater homogeneity at the 5' and 3' ends. Preferably, the RNA concatemers produced are more than 1000 nucleotides in length, more preferably in excess of 5000 nucleotides in length. For DNA synthesis, the multimer product is preferably about 500–100,000 nucleotides in length.

The length of the multimer can be controlled by time, temperature, the processivity of the polymerase enzyme, and the relative and absolute concentrations of the reaction components including enzyme, triphosphates, template, and primer. For example, longer periods of time, or lower concentrations of template, will tend to increase the average multimer length. The rolling circle method preferably uses only catalytic amounts of template, primer, and polymerase enzymes and stoichiometric amounts of the nucleotide triphosphates. Theoretically, the maximum size of multimer product is unlimited, however, often it is about $10^4$–$10^6$ nucleotides in length.

More preferably, the template concentration is about 0.1 μM to about 1 mM, the primer concentration is about 0.1 μM to about 1 mM, and the triphosphate concentration is about 1 μM to about 1000 mM. The preferred molar ratio of triphosphate(s) to template is about 50:1 to about $10^7$:1. The preferred molar ratio of primer to template is about 0.1:1 to about 100:1. These preferred amounts, i.e., concentrations and molar ratios, refer to amounts of the individual components initially provided to the reaction mixture.

The preferred reaction time for the rolling circle synthesis is about 1 hour to about 3 days. Preferably, the temperature of the reaction mixture during the rolling circle synthesis is about 20–90° C. For polymerase enzymes that are not thermally stable, such as DNA polymerase I and its Klenow fragment, and other nonengineered enzymes, the temperature of synthesis can be about 20–50° C. For thermostable polymerases, such as that from *Thermus aquaticus*, the temperature of synthesis can be about 50–100° C.

Oligomers may be detectably labeled if desired by adding at least one detectably labeled base triphosphate (dNTP or rNTP) to the reaction mixture along with the unlabeled triphosphates at the beginning of the reaction. This produces multimer and end-product oligomers that are labeled internally. For example, spiking the reaction mixture with an effective amount of α-$^{32}$P-dCTP produces labeled oligomers having $^{32}$P at one or more of the internal positions occupied by a C residue. Alternatively, a detectably labeled oligonucleotide primer can be used, which results in a 5' detectably labeled multimer.

Preferred polymerase enzymes that effectuate the synthesis of a multimer in rolling circle synthesis have high fidelity, high processivity, accept single-stranded templates, and have relatively low exonuclease activity. For DNA polymerization, i.e., formation of DNA multimers, suitable enzymes include, but are not limited to, DNA Polymerase I, Klenow fragment of DNA Polymerase I, T7 DNA Polymerase (exonuclease-free), T4 DNA Polymerase, Taq Polymerase, and AMV (or MuLV) Reverse Transcriptase or closely homologous mutants. This group of enzymes is also preferred. More preferably, the enzyme for DNA polymerization is the Klenow enzyme.

For RNA polymerization, i.e., formation of RNA multimers, suitable enzymes include, but are not limited to, the phage polymerases and RNA Polymerase II. Preferred enzymes for RNA polymerization are T7, T4, T3, *E. coli* and SP6 RNA Polymerases, as well as RNA Polymerase II and RNA Polymerase III or closely homologous mutants. Particularly preferred enzymes are T7 and *E. coli* RNA polymerase.

It is to be understood that the term "nucleotides" as used herein includes, but is not limited to, naturally occurring and/or synthetic nucleotides, nucleotide analogs, and nucleotide derivatives. For example, the term includes naturally occurring DNA or RNA monomers, nucleotides with backbone modifications such as peptide nucleic acid (PNA) (M. Egholm et al., *Nature*, 365, 566–568 (1993), incorporated by reference in its entirety), phosphorothioate DNA, phosphorodithioate DNA, phosphoramidate DNA, amide-linked DNA, MMI-linked DNA, 2'-O-methyl RNA, alpha-DNA and methylphosphonate DNA, nucleotides with sugar modifications such as 2'-O-methyl RNA, 2'-fluoro RNA, 2'-amino RNA, 2'-O-alkyl DNA, 2'-O-allyl DNA, 2'-O-alkynyl DNA, hexose DNA, pyranosyl RNA, and anhydrohexitol DNA, and nucleotides having base modifications such as C-5 substituted pyrimidines (substituents including fluoro-, bromo-, chloro-, iodo-, methyl-, ethyl-, vinyl-, formyl-, ethynyl-, propynyl-, alkynyl-, thiazolyl-, imidazolyl-, pyridyl-), 7-deazapurines with C-7 substituents (substituents including fluoro-, bromo-, chloro-, iodo-, methyl-, ethyl-, vinyl-, formyl-, alkynyl-, alkenyl-, thiazolyl-, imidazolyl-, pyridyl-), inosine and diaminopurine.

Nucleotide triphosphates suitable for use in the synthetic method of the invention or for use in constructing the circular oligonucleotide template used in the method of the invention include any that are useful in standard PCR or polymerase technology. That is, any nucleotide triphosphate can be used in the rolling circle method that is capable of being polymerized by a polymerase enzyme. Suitable NTPs include both naturally occurring and synthetic nucleotide triphosphates. They include, but are not limited to, ATP, dATP, CTP, dCTP, GTP, dGTP, UTP, TTP, dUTP, 5-methyl-CTP, 5-methyl-dCTP, ITP, dITP, 2-amino-adenosine-TP, 2-amino-deoxyadenosine-TP as well as the alpha-thiotriphosphates for all of the above, and 2'-O-methyl-ribonucleotide triphosphates for all the above bases. Other examples include 2'-fluoro-NTP and 2'-amino-NTP. Preferably, the nucleotide triphosphates used in the method of invention are selected from the group consisting of dATP, dCTP, dGTP, TTP, and mixtures thereof. Modified bases can also be used, including but not limited to, 5-Br-UTP, 5-Br-dUTP, 5-F-UTP, 5-F-dUTP, 5-propynyl dCTP, and 5-propynyl-dUTP. Most of these nucleotide triphosphates are available from commercial sources such as Sigma Chemical Co., St. Louis, Mo. Nucleotide triphosphates are advantageously used in the method of the present invention at least because they are generally cheaper than the nucleotide precursors used in automated synthesis.

Rolling circle synthesis of the oligonucleotide multimer of the invention can be carried out in solution, as described above, or on a solid support. In solid phase synthesis an oligonucleotide primer is covalently or noncovalently attached, typically at the 5' end or in the middle of the primer sequence, to a solid support. One of skill in the art would be familiar with a variety of attachment chemistries and protocols (e.g., S. Beaucage et al., *Tetrahedron*, 49, 1925 (1993)). The primer is extended in combination with a circular template, a polymerase, and the required dNTPs or rNTPs as described herein under suitable reaction conditions. If desired, a labeled NTP can be supplied to produce an oligonucleotide multimer that is detectably labeled. The oligonucleotide multimers are optionally separated from the solid support using well-known procedures that are selected based upon the coupling chemistry used to attach the primer to the solid support.

When isolating the multimeric products from the other components of the reaction mixture, it is preferable to utilize separation methods that allow for preferential isolation of longer multimers, more preferably multimers of at least about 1000 nucleotides in length. The longer multimers are generally more desirable because they are more intensely labeled on a per-strand basis than the shorter multimers. Numerous isolation and separation procedures known in the art can be used to obtain the multimer products of the desired length. Examples of such procedures include separation by gel electrophoresis followed by excision and isolation, separation by size exclusion chromatography, and separation by equilibrium dialysis.

The rolling circle method of the present invention can also be used to produce double-stranded DNA oligomers, if desired. This is accomplished by one of two methods. Rolling circle synthesis can be carried out separately on each of the complementary strands, and the resulting multimer products combined at the end and then cleaved to give the desired duplex oligomers. Alternatively, two complementary circular templates can be placed in the reaction mixture simultaneously along with one primer for each strand (the primers are not complementary to each other). In this way, two primed circular templates are formed. The rolling circle synthesis can be carried out for both the complementary strands at the same time. That is, amplified run-on synthesis occurs with each primed circular template. This is possible because the two circular templates, although complementary to each other in sequence, cannot hybridize completely with each other as they are topologically constrained. As the complementary multimeric strands are formed, they combine to form the desired double-stranded multimer. This double-stranded multimer can then be cleaved to produce the desired double-stranded oligomers having well-defined ends.

The multimeric products generated from the synthetic method of the invention include linear or circular, single or double stranded DNA or RNA or analog multimer. The multimer can contain from about 60 to about $5 \times 10^6$ nucleotides, preferably about 500–100,000, or about 5–100,000 copies of the desired nucleotide sequence.

Detectably labeled DNA and RNA oligonucleotide multimers. The detectably labeled oligonucleotide multimer of the invention comprises multiple contiguous copies of a repeated RNA or DNA oligonucleotide, wherein at least one copy of the repeated oligonucleotide contains at least one detectable label. Preferably, a multiplicity of the repeated oligonucleotides comprises at least one occurrence of the detectable label. The detectable labels are preferably covalently linked to the oligonucleotide multimer. Alternatively, the detectably labeled oligonucleotide multimer may be labeled noncovalently. For example, an unlabeled oligonucleotide multimer can be labeled, under suitable hybridizing conditions, by contact with a detectably labeled oligonucleotide that is complementary to all or a portion of a single repeat unit. Multiple copies of the detectably labeled complementary oligonucleotide bind along the length of the multimer, thereby labeling the multimer.

The detectably labeled oligonucleotide multimer of the invention may contain DNA, RNA, or any desired derivative or analog thereof, as described above. Preferably, the oligonucleotide multimer contains DNA.

A preferred detectably labeled oligonucleotide multimer of the invention has a 5' nonrepeated region located 5' to the 3' repeating unit region. The 5' nonrepeated region may contain one or more of a nucleotide, peptide, protein, carbohydrate, lipid, hormone, any other type of chemical moiety, or any combination thereof. In a preferred embodiment, the 5' nonrepeated region of the detectably labeled oligonucleotide multimer contains a nucleotide sequence, preferably at least about 6 nucleotides, more preferably at least about 7 nucleotides, and most preferably about 10–40 nucleotides.

The detectably labeled oligonucleotide multimer of the invention can comprise a nucleotide sequence conjugated to a nonnucleotide molecule, such as a biotin molecule, a peptide, or a protein. Preferably, the conjugated molecule is covalently linked to the 5' end of the nucleotide sequence of the oligonucleotide multimer. The 5' nonrepeated region of the detectably labeled oligonucleotide multimer can, for example, contain a moiety designed to decrease the susceptibility of the oligonucleotide multimer to enzymatic degradation by, for example, nucleases that may be present in biological samples (sometimes known in the art as a "5' cap"). Alternatively, the conjugated molecule can be involved in binding to a designated target molecule, as described hereinbelow.

In a particularly preferred embodiment of the invention, the 5' nonrepeated region contains a binding region that binds a target molecule. An oligonucleotide multimer containing a binding region in the 5' nonrepeated region is sometimes referred to herein as an "oligonucleotide multimer probe". The binding region of the 5' nonrepeated region can be selected or designed so as to bind to any desired target molecule, such as a nucleic acid, peptide, protein, carbohydrate, lipid, hormone, any derivative thereof, or any other molecule of interest. Preferably, the target molecule is a nucleic acid molecule.

The binding region of the 5' nonrepeated region can contain a nucleotide, peptide, protein, carbohydrate, lipid, hormone, any derivative thereof, any other type of chemical moiety, or any combination thereof. Preferably, the binding region contains a nucleotide sequence, more preferably a nucleotide sequence that is complementary to the nucleotide sequence of a target nucleic acid molecule, so as to enable the detectably labeled oligonucleotide multimer to hybridize to the target nucleic acid molecule under suitable hybridizing conditions. Where the binding region contains a nucleotide sequence, the nucleotide sequence preferably contains at least about 7 nucleotides, preferably about 12–30 nucleotides.

The binding region on the oligonucleotide multimer is typically relatively short in comparison to the 3' repeating unit region and can be selected or designed by those skilled in the art such that binding specificity is high. For example, the 5' nonrepeated region can include a nucleotide sequence containing a partially self-complementary hairpin sequence (a "stringency clamp"), such that binding to the target nucleic acid molecule must successfully compete with formation of the hairpin (R. W. Roberts et al., *Proc. Nat'l. Acad. Sci. USA*, 88, 9397–9401 (1991)). At least a portion of the self-complementary sequence must be present in the binding region in order to bring about the binding competition.

In an alternate embodiment, the binding region is a nucleotide sequence present on all or a portion of the sequence of the repeated oligonucleotide of the oligonucleotide multimer. The oligonucleotide multimer will thus contain multiple copies of the binding region in the 3' end of the molecule.

It is desirable to avoid nonspecific or background binding of the oligonucleotide multimer probe to non-target molecules present in a sample. Thus, when the binding region is part of the 5' nonrepeated region, the oligonucleotide sequence that is repeated in the 3' tail of the oligonucleotide multimer is preferably not complementary to and therefore does not bind nucleic acids present in the sample. Sequences having limited complexity are more likely than others to avoid nonspecific or background binding of extant nucleic acids in a sample and are therefore preferred. Sequences of limited complexity include, for example, sequences containing 3 or fewer nucleotide types (e.g., sequences containing adenine, guanine, cytosine but not thymidine or uracil), sequences wherein one base is overrepresented (preferably at a level of at least about 50%, more preferably at a level of at least about 80%), sequences possessing symmetry such as palindromic or mirror plane sequences, or repeating sequences. It should be noted that the end-to-end nucleotide sequence of the detectably labeled oligonucleotide multimer, viewed as a whole, is already of limited complexity because a substantial portion of the molecule is characterized by the repeating nucleotide sequence that forms the 3' tail. The limited sequence complexity of the detectably labeled oligonucleotide multimer also has the effect of inhibiting the formation of secondary structure in the oligonucleotide multimer. Sequences preferred for use as the repeating sequence in the detectably labeled oligonucleotide multimer are less likely than others to be homologous to genomic sequences (see A. H. Bledsoe et al., *J. Mol. Evol.*, 30, 425–433 (1990), incorporated by reference in its entirety, for a discussion of homology).

If the repeating sequence of the multimer tail is accidentally homologous to nucleic acid sequences present in a sample, nonspecific or background binding of the multimer tail to the nucleic acids present in the sample can be prevented by adding, prior to the hybridization reaction, a monomer or multimer oligonucleotide complementary to at least a portion of the repeating sequence in the tail, thus blocking nonspecific or background binding by making the tail double-stranded.

The detectable label of the detectably labeled oligonucleotide multimer can be any detectable label known and used in the arts of chemistry, biochemistry, molecular biology, or the like, including, for example, a fluorescent or phosphorescent label, an enzymatic label, such as alkaline phosphatase or horse radish peroxidase, a chemical label, or a radiolabel. Preferably, the label is a fluorescent label, a biotin label, a digoxigenin label, or a radiolabel, such as $^{32}P$, $^{33}P$, $^{35}S$, or $^{125}I$. More preferably, the label is a fluorescent moiety.

Preferably, multiple copies of the detectable label are covalently linked to the oligonucleotide multimer. Covalent incorporation of the label can be conveniently accomplished during rolling circle synthesis of the multimer (preferably in the absence of auxiliary enzymes, as described above) by providing as a reagent labeled dNTPs or rNTPs. An effective amount of at least two types of nucleotide triphosphates is supplied, at least one of which comprises the detectable label. The synthesis is performed using a circular template that contains one or more nucleotides complementary to the nucleotide triphosphate comprising the detectable label. Preferably, the size of the circular template is 15–1500 nucleotides.

Examples of suitable labeled NTPs include fluorescently labeled, biotin-labeled, digoxigenin-labeled or radiolabeled dATP, dTTP, dGTP, dCTP, d(isoC)TP, d(isoG)TP, rATP, rTTP, rGTP, rCTP, r(isoC)TP and r(isoG)TP. dUTP and rUTP conjugates, preferably those labeled with a fluorophore such as fluorescein, rhodamine, biotin, pyrene, sulforhodamine (Texas Red™), coumarin, Oregon green, cyanine dyes, lanthanide complexes and RuBipy complexes, are preferred. A particularly preferred labeled dNTP adduct is fluorescein-dUTP.

When supplied during the synthetic reaction, the labeled mononucleotides are available for uptake and covalent incorporation into the multimer each time the polymerase reaches a complementary nucleotide on the circular oligonucleotide template. Typically, during the synthetic reaction, the labeled NTP (dNTP or rNTP) is provided together with an amount of unlabeled carrier NTP (dNTP or rNTP). The probability of incorporation of the labeled NTP into the growing multimer product depends on the ratio of the labeled NTP to carrier NTP, and also on the relative efficiency with which the labeled NTP is taken up during the synthetic reaction. The intensity of labeling in the product multimer can be regulated by altering the ratio of labeled NTP to carrier NTP.

In the case of a fluorescent multimer, the potential incorporation sites for the labeled nucleotide triphosphate are preferably separated on the circular template by at least about 10 nucleotides, more preferably by at least about 20 nucleotides. The fluorescence quenching (which lessens with increasing distance) is thereby minimized while retaining a high number of labels per oligonucleotide multimer.

The present invention also provides a method for detecting a target molecule using the detectably labeled RNA or DNA oligonucleotide multimer of the invention which comprises a binding site for the target molecule. In the present detection method, the detectably labeled oligonucleotide multimer is brought into contact with a sample suspected of containing the target molecule. If the target molecule is present in the sample, the oligonucleotide multimer binds to the target molecule to form a detectably labeled multimer-target complex. Optionally, prior to bringing the detectably labeled oligonucleotide multimer into contact with the target molecule, the oligonucleotide multimer can be contacted with a blocking oligonucleotide having a nucleotide sequence complementary to at least a portion of the nucleotide sequence of the repeated oligonucleotide, so as to prevent unwanted nonspecific or background binding of the detectably labeled oligonucleotide multimer to nontarget molecules in the sample.

Detection of the multimer-target complex can be accomplished by any convenient method. For example, radiation emitted by a fluorescently labeled or radiolabeled oligonucleotide multimer can be directly detected by fluorescence microscopy, flow cytometry, phosphorimaging, or autoradiography. Detection of a biotin- or digoxigenin-labeled multimer requires the use of a secondary molecule and thus permits additional amplification of the signal. For example, biotin labels can be detected using avidin or streptavidin in various forms of sandwich assays well known in the art, and can also be detected using the appropriate antibodies. Digoxigenin labels can be detected, for example, using various forms of immunoassay. For example, sheep anti-digoxigenin can bind to a digoxigenin-labeled multimer probe, and the complex can be reacted with fluorescently-labeled rabbit anti-sheep IgG.

The present invention additionally provides a method of making RNA and DNA oligonucleotide multimers, preferably detectably labeled multimers, using the rolling circle synthetic method of the invention as described above. In the synthesis of detectably labeled DNA oligonucleotide multimers, and optionally in the synthesis of detectably labeled RNA oligonucleotide multimers, an oligonucleotide primer containing a sufficient number of consecutive nucleotides (the "priming" nucleotides) at the 3' end complementary to a portion of the sequence of the circular oligonucleotide template is used to initiate primer extension under suitable reaction conditions. Optionally, the oligonucleotide primer contains, 5' to the priming nucleotides, additional nucleotides or other adducts or moieties, preferably constituting all or a portion of a target-binding region. The additional nucleotides have a sequence that is not complementary to the nucleotide sequence of the circular oligonucleotide template and hence is not repeated on the oligonucleotide multimer product. Covalent labeling of the multimeric product is accomplished as described above by supplying selected detectably labeled rNTPs and dNTPs during the synthetic reaction.

If desired, oligonucleotide multimer probes can be synthesized that each contain a different fluorescent label in the repeating unit multimer tail, to generate probes of different colors. Thus, multiple color analysis can be used for fluorescence in situ hybridization (FISH) applications if desired.

Detectably labeled oligonucleotide multimers of the invention, incorporating multiple copies of the detectable label into the 3' tail, are especially useful in applications requiring high sensitivity detection. The present invention allows for quick and efficient synthesis of such multiply labeled probes. An example of a high sensitivity application is the detection of hybridization between a fluorescent probe and a chromosome preparation on a microscope slide, using standard in situ hybridization conditions well known to those of skill in the art (*Short Protocols in Molecular Biology*, chapter 14, 3rd Ed., Wiley (1995), incorporated by reference in its entirety).

Under sufficiently stringent conditions, a detectably labeled oligonucleotide multimer probe binds only to the target sequence on the gene of interest, and is visible as a fluorescent spot on a chromosome by fluorescence microscopy. Hybridization conditions are adjusted to give the desired level of specificity and stringency. The oligonucleotide multimer probe can also be hybridized to complementary DNAs or RNAs affixed to a membrane for use in Southern and Northern dot- or slot-blot methods. The oligonucleotide multimer probe can bind to any molecule for which it has sufficient binding affinity, and can accordingly be used for applications such as Western assays, wherein the probe binds to a target protein affixed to a membrane. Very small amounts of a target sequence are detectable and/or identifiable because, once bound to the target, as little as one molecule of the fluorescently labeled oligonucleotide multimer is detectable.

The signal intensity of the oligonucleotide multimer probe can be increased even further by using "sandwich assays". For example, biotin (commonly used in sandwich assays) is known to strongly bind avidin and streptavidin. Thus, an aspect of the present invention provides a detectably labeled oligonucleotide multimer conjugated to a biotin molecule; when the biotin moiety binds the target avidin or streptavidin. The bound complex can be detected by detecting the detectable label, preferably a fluorescent label, incorporated into the oligonucleotide tail.

For example, a 5'-biotinylated oligonucleotide primer can be used for rolling synthesis of an oligonucleotide multimer with uptake of a fluorescent nucleotide at defined positions in the repeating sequence as described above, yielding a biotin-conjugated, detectably labeled multimer characterized by a single biotin covalently attached to a fluorescent oligonucleotide multimer. The fluorescent biotin-conjugated multimer can be used to label a target avidin or streptavidin molecule.

In a preferred embodiment of the present method, the "target" avidin or streptavidin to which the biotin-conjugated multimer binds is present as a component of a probe-target molecule complex. This probe-target molecule complex is formed by contacting a biotinylated conventional probe, such as an oligonucleotide or ligand capable of binding the target molecule, with the target molecule to form a bound complex between the biotinylated probe and the target molecule. Avidin is then added and binds to the biotin of the biotinylated probe-target molecule complex, producing a bound complex containing the biotinylated probe, the target molecule, and avidin. It is this three-part complex that is detected and amplified by contact with the biotin-conjugated, detectably labeled oligonucleotide multimer of the invention. In this way the signal intensity of any conventional probe can be amplified. This labeling method is thus capable of highly sensitive detection of any target molecule in a sandwich assay.

The detectably labeled oligonucleotide multimer of the invention can also be used to affinity label proteins. Any known ligand for a protein capable of being conjugated to a short primer oligonucleotide can be labeled with, for example, a fluorescent multimer, using primer extension on a circular template. The ligand may be a protein, an oligonucleotide, a polysaccharide, a hormone, or any other molecule that binds a protein, covalently or noncovalently. Primer extension is carried out either in vitro prior to use or in situ after binding of the ligand-primer conjugate has taken place.

The detectably labeled oligonucleotide multimer of the invention can also be used for signal amplification in highly sensitive affinity capture and sequence identification applications. For example, the design, construction and use of branched DNAs have recently been reported as high-sensitivity affinity capture groups for detection and identification of target nucleic acids in separation methods based on affinity binding (T. Horn et al., *Nucleosides Nucleotides*, 8, 875 (1989), incorporated by reference in its entirety).

Branched DNA probes comprise a single target-binding sequence at the narrow end of the branch, and multiple copies of the target sequence itself at the branched end. Branched structures allow a single target-binding DNA probe to bind several additional DNA probes (on the "branches"), resulting in multiple probes bound to a single target, thus amplifying the signal. Branched DNAs are very difficult to synthesize. Use of the easily synthesized detectably labeled oligonucleotide multimer of the invention could either augment or replace branched DNAs in hybridization assays and other hybridization applications.

The present invention also provides a randomized detectably labeled multimer library useful for identifying protein and ligand binding motifs. An optimized set of single-stranded DNA sequences that bind a protein or other molecule of interest can be identified by in vitro selection methods involving one or more rounds of selection, enrichment, and isolation performed on a randomized multimer library. A suitable library has been prepared, for example, by A. Fire et al., *PNAS USA*, 92, 4641 (1995). A randomized library of multimer sequences supplies multiple copies of each randomized sequence, greatly facilitating detection of binding sequences and according greater sensitivity to the selection process.

Cleavage of multimer into desired oligomers. Once formed, a linear multimer containing multiple copies of the desired oligonucleotide can be cleaved, if desired, into single copy oligomers having the desired sequence. Cleavage can be carried out either while synthesis is occurring or after oligonucleotide synthesis is complete. The RNA or DNA oligonucleotide multimer can be cleaved into single-stranded oligomers by a variety of methods. Cleavage can be carried out during the rolling circle stage, i.e., as the multimer is formed, or after the polymerase reaction is complete. Purification of the resultant oligomer can then be carried out if desired. Also, if desired, at this stage the synthesized oligomers can be cyclized into new circles for use as DNA/RNA binding agents, therapeutic or diagnostic agents, or as templates for the rolling circle synthesis of the complementary strand.

There are several techniques that can be used for the cleavage reaction. For example, restriction endonucleases can be used to cleave specific sequences that occur in the multimer. They can be used alone, or in some cases, with addition of a short DNA strand that aids in the reaction. The cleavage reaction also can be carried out using chemicals other than enzymes to effect cleavage of the multimer. For example, Maxam-Gilbert cleavage reagents can be used to cleave the strand at a base that occurs once between each oligomer.

In the case of RNA synthesis, the method preferably produces multiple copies of a short, sequence-defined RNA oligonucleotide (oligoribonucleotide). These RNA oligonucleotides are formed by cleavage of the long concatemeric repeating unit RNA produced by rolling circle transcription. In a preferred embodiment, cleavage is autolytic, as where the monomeric units contain self-cleaving ribozymes. During the transcription reaction, the repeating RNAs self-cleave, reaching monomer length (i.e., they are cleaved to produce oligonucleotides containing only one copy of the desired RNA oligonucleotide sequence) after a sufficient period of time has elapsed.

Typically the monomers are linear, but they may be cyclic, as where the monomer contains a hairpin-type ribozyme, a hammerhead ribozyme, a hepatitis delta ribozyme, or other motif that can be ligated intramolecularly. The resulting monomeric RNAs preferably include catalytically active ribozymes which can sequence-specifically cleave RNA targets in trans. As an example, a self-cleaving multimer would result from inclusion of the hammerhead sequence and its cleavage substrate (A. C. Forster et al., *Cold Spring Harbor Symp. Quant. Biol.,* 52, 249 (1987)) in the RNA oligomer. Cleavage of the concatemeric RNA product can also be accomplished chemically or enzymatically, as by contact with a second molecule possessing site-specific endonuclease enzymatic activity. The second molecule can be, for example, a protein or a ribozyme acting in trans. For example, an RNA multimer could also be cleaved at any sequence by using a hammerhead sequence in trans. See J. Haseloff et al., *Nature,* 334, 585 (1988).

Another example of cleavage of an RNA multimer would be specific cleavage between G and A in the sequence 5'-GAAA, which can be achieved by the addition of the oligomer 5'-UUU and $Mn^{2+}$, following the method of Altman described in S. Kazakov et al., *Proc. Natl. Acad. Sci. USA,* 89, 7939–7943 (1992), which is incorporated herein by reference. RNA can also be cleaved using catalysts such as those described in J. Kim, *J. Am. Chem. Soc.,* 114, 9792 (1992), incorporated herein by reference, which have been attached to a DNA oligomer for sequence specificity. Alternatively, the enzyme RNase H can be used along with addition of a DNA oligomer, or base-specific RNases can be used.

To cleave DNA, any one of several methods can be used. Single-stranded or double-stranded multimers can be cleaved into single-stranded or double-stranded multimers, respectively. For example, the multimer can be cut at a restriction enzyme site that has been incorporated into the sequence, leaving the restriction sequence in the oligomer product. This is demonstrated by Examples 1 and 7. Optionally, the remaining restriction site sequences can be removed from the oligonucleotide with an exonuclease or another restriction or nuclease enzyme. A hairpin sequence can be cut out using a Type II restriction enzyme. This is demonstrated by Example 3. The strand can be cut at any desired site using a Type II restriction enzyme and the method of Szybalski as described in W. Szybalski, *Gene,* 40, 169 (1985), and A. Podhadjska et al., *Gene,* 40, 175 (1985), which are incorporated herein by reference.

The Szybalski and Podhadjska et al. references concern the use of FokI restriction enzyme and an adapter oligonucleotide to cleave DNA at predetermined sites, i.e., they disclose a method of providing enzyme specificity by synthetic design. That is, these references disclose methods for cleaving of DNA, but not methods for amplifying DNA. The result of the method disclosed by these references is a double-stranded DNA molecule that contains a recognition sequence for class IIS restriction endonucleases.

If the nucleotide sequence of the desired oligomer does not contain all four bases, the fourth base can be added once per repeat and cleaved in the multimeric product specifically by the Maxam-Gilbert methods, thereby producing oligomers with 3'- and 5'-phosphate end groups. This is done by including the complement of this fourth base, or any other cleavable nucleotide, either natural or modified, in the circular oligonucleotide template. Maxam-Gilbert methods are described in J. Sambrook et al., *Molecular Cloning,* 2nd ed.; Cold Spring Harbor Press, 1989, which is incorporated herein by reference.

Chemical cleavage of a nucleotide multimer at a natural nucleotide incorporated into the multimer is demonstrated by Examples 2, 8 and 11. Cleavage of a multimer at a modified nucleotide is demonstrated by Example 9. In this example, a base is modified with a photolabile group, such as an ortho-nitrobenzyl group. Alternatively, an incorporated modified base can be used to cleave a multimer by specific chemical or redox signals, leaving the desired oligomers. For example, a modified purine such as N-7-deaza-7-nitro purine can be incorporated into the oligonucleotide multimer, permitting base-catalyzed cleavage at that site, as by the use of piperidine. Similarly, a N-7-methyl purine can be incorporated to provide a site for base-catalyzed cleavage of the multimer.

Another possibility for cleavage of the nucleotide multimers formed by the rolling circle synthesis of the present invention is the development of sequence-specific endonucleases. For example, S1 nuclease can be attached covalently to a linear or circular oligomer to give cleavage at specific sequences. RNase H can also be attached to such oligomers for cleavage of RNA.

Once the multimer is cleaved into the oligomer, the oligomer can be isolated by standard methods. The oligomer can also be circularized using the same methods described for circularizing a linear precircle into the circular template as described herein.

The following examples are offered to further illustrate the various specific and preferred embodiments and techniques. It should be understood, however, that many variations and modifications may be made while remaining within the scope of the present invention.

EXAMPLES

Example 1

Synthesis of a 34-nt DNA Oligomer

A linear 34-nucleotide (34-nt) precircle DNA oligonucleotide having the sequence (SEQ ID NO: 1):
5'-pAAAGAAGAGG GAAGAAAGAA AAGGGGTGGA AAAG,
was machine synthesized on a Pharmacia LKB Gene Assembler Plus using standard β-cyano-ethyl phosphoramidite chemistry as disclosed in S. L. Beaucage et al., *Tetrahedron Lett.*, 22 1859 (1981), which is incorporated herein by reference. This precircle template is complementary to the desired oligomer. The sequence of the desired oligonucleotide product is (SEQ ID NO:2):

5'-pTTTTCCACCC CTTTTCTTTC TTCCCTCTTC TTTC, which has an MnlI enzyme cleavage site at its end. Using this enzyme, a polymeric version of this oligomer, i.e., a multimer, can be cut into oligomers having this sequence. A ligation adaptor, 5'-TTTTCTTTCTT (SEQ ID NO:27), was also machine synthesized, as described above. This was also used as the primer oligomer.

The precircle template (100 nmol) was cyclized into the template circle (SEQ ID NO:3):

(the arrow denotes 5' to 3' directionality)

using the following method with the ligation adaptor to align the ends. The precircle template and ligation adaptor oligomers were placed in a 1-mL syringe in a programmable syringe pump. The oligomers were at 50 μM concentration. The syringe was connected by a tube to a 5-mL reaction vial. A reaction buffer, composed of 20 mM EDC, 20 mM MgCl$_2$, and 50 mM 2-(N-Morpholino) ethane-sulfonic acid (MES) buffer (obtained from Sigma Chemical Co., St. Louis, Mo.) was placed in the vial. The syringe pump was then used to deliver the adaptor to the reaction vial slowly (over a period of 24 hours at 4° C.). This method kept the effective concentrations very low, maximizing cyclization relative to dimerization. At the same time, it allowed the reaction to be carried out in a relatively small volume, making recovery of the product easier. Alternatively, the circular template can be constructed using BrCN/imidazole and a divalent metal in a manner analogous to that disclosed in G. Prakash et al., *J. Am. Chem. Soc.*, 114 3523–3527 (1992), and E. Kanaya et al., *Biochemistry*, 25, 7423–7430 (1986). Gel electrophoresis was used to separate the circular product from starting material. This separation step was optional. Further experimental details of an analogous cyclization step are outlined in Example 5.

For the rolling circle synthesis of the desired oligonucleotide product, the template circle (10 μM), primer (10 μM), dATP (2 mM), dTTP (2 mM), and dGTP (2 mM) were dissolved in a buffer containing 34 mM tris(hydroxymethyl) aminomethane (Tris-HCl) (pH 7.4, obtained from Sigma Chemical Co., St. Louis, Mo.), 3.4 mM MgCl$_2$, 2.5 mM dithiothreitol, 25 μg/ml bovine serum albumin, and 20% polyethylene glycol 8000 (PEG 8000). The Klenow fragment of DNA Polymerase I (2 units, obtained from United States Biochemical, Cleveland, Ohio) was also added. The reaction was allowed to proceed for 1 hour at 0° C., and then for 6 hours at 37° C. Further experimental details of an analogous rolling circle synthesis step are outlined in Example 6. Gel electrophoresis of a small aliquot of this solution showed very light bands corresponding to the template and very dark slow bands corresponding to the nucleotide multimers produced. The sequence of these multimers is as follows (SEQ ID NO:4):

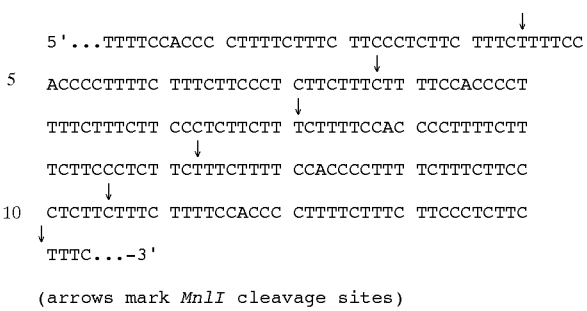

(arrows mark MnlI cleavage sites)

To cleave the product multimers into the desired oligonucleotide product, 10 units of MnlI restriction enzyme (available from New England Biolabs, Beverly, Mass.) can be added. Incubation at 37° C. results in cleavage of the multimers into a single product, which would be seen as a very dark band by gel electrophoresis. This dark band is the desired 34-base oligomer. Further experimental details for an analogous cleavage step are outlined in Example 7.

If desired, the oligomer could be further purified. Gel filtration should easily remove unreacted oligomers and the two proteins. If removal of the very small amount of circle template is desired, gel electrophoresis or affinity chromatography will accomplish this.

The oligonucleotide product can also be converted into circular form if desired, using the method described in G. Prakash et al., *J. Am. Chem. Soc.*, 114, 3523–3527 (1992), which is incorporated herein by reference. This method will work using the crude oligomer i.e., unpurified product, from the reaction. These 5'-phosphorylated circle precursors are hybridized with short complementary DNA templates, which bring the reactive 3'-hydroxyl and 5'-phosphate ends adjacent to one another. These ends are ligated using BrCN/imidazole/Ni$^{2+}$, in a manner analogous to the method described in G. Prakash et al. and E. Kanaya et al. It is worth noting that this second circle could be used as a template for rolling circle synthesis of the precircle template oligomer, eliminating the need for any machine synthesis in the long term.

Example 2

Synthesis of a Linear Oligomer of Sequence dT$_{12}$

The circular template used for the synthesis of the sequence 5'-pdTTTTTTTTTT TTp (SEQ ID NO:7) is (SEQ ID NO:5):

The precircle sequence used to synthesize this circular template is 5'-dCAAAAAAAAA AAACAAAAAA AAAAAAp (SEQ ID NO:5). The primer/adaptor sequence is 5'-dTTTTGTTT. The circular template is constructed from the linear precircle and the adaptor using BrCN/imidazole under high dilution. Alternatively, the circular template can be constructed using 1-(3-dimethylaminopropyl)-3 ethylcarbodiimide HCl under the conditions described in Example 1.

For the rolling circle synthesis of the desired oligonucleotide product, only two triphosphates, dTTP and dGTP, are used following the conditions described in Example 1. Workup can be done by polyethylene glycol (PEG) precipitation. The product formed is the multimer 5' . . . GTTTTTTTTT TTTGTTTTTT TTTTTTGTTT TTTTTTTTT . . . (SEQ ID NO:6). The pellet can be resuspended in a Maxam-Gilbert G buffer. This suspension is treated by the Maxam-Gilbert "G" reaction. The Maxam-Gilbert "G" reaction is described in J. Sambrook et al., *Molecular Cloning,* 2nd ed.; Cold Spring Harbor, 1989, Chapter 13, which is incorporated by reference. The resultant desired oligomer has the sequence 5 '-pdTTTTTTTTTT TTp (SEQ ID NO:7).

Example 3
Synthesis of dAAGAAAGAAA AG

A schematic of the synthesis of the linear sequence 5'-pdAAGAAAGAAA AG (SEQ ID NO:8), is shown below in Scheme II. In this example, a partially self-complementary sequence was included in the circular template. No adapter was needed for cyclization because the molecule is self-complementary. The method for cyclization used is described in G. W. Ashley et al., *Biochemistry,* 30, 2927 (1991), which is incorporated herein by reference. The multimer was synthesized as described in Examples 1 and 5. The multimer product can be cleaved with BsmAI restriction enzyme, which removes the hairpins, leaving the desired product oligomer as the 5'-phosphate. Note that the product oligomer contains no restriction enzyme sequences.

Scheme II precircle  5'-AGACGAAGAT CAAACGTCTC TAAGACTTTT CTTTCTTAGp
self-templated (no adapter needed) (SEQ ID NO: 22)

ligation using the
method disclosed in
G.W. Ashley et al.

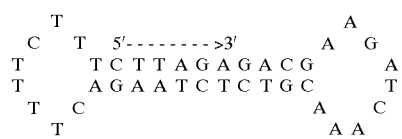

circular template (SEQ ID NO: 9)

dNTP's          rolling
Klenow enzyme   circle
primer (5'-TTTGATCT) synthesis

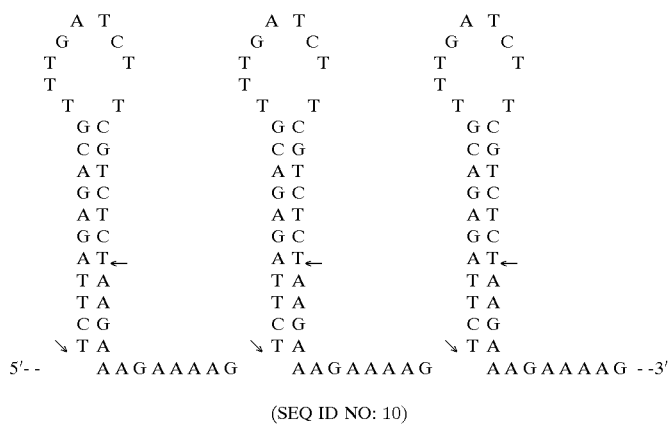

(SEQ ID NO: 10)

BsmAI restriction

5'-pdAAGAAAGAAA AG
5'-pdAAGAAAGAAA AG
         5'-pdAAGAAAGAAA AG

Desired Oligomer (SEQ ID NO: 11)

-continued

Scheme II

```
                    A T
                  G   C
                 T     T  A T
                T       G   C
         A T   T   T T      T
        G   C    G C   T
       T   T    C G      T   T
       T        A T      G C
        T   T   G C      C G
         G C    A T      A T
         C G    G C      G C
         A T    A T      A T
         G C     T       G C
         A T     T       A T
         G C     C        T
         A T  5'-pdT      T
         T                C
         T             5'-pdT
         C
       5'-pdT
```

(SEQ ID NO: 12)

Example 4

Synthesis of Additional Template

A circle very similar to that in Example 1 was constructed. In this example, the circular product is used as a template to produce more of the original template. A schematic illustration of this synthetic procedure is shown below in Scheme III.

Scheme III precircle: 5'-GATCAGAAAA GAAAGAAGGA GGAAGAAAGA AAAGp
(SEQ ID NO: 13)
+
adaptor/primer 5'-GATCCTTTT ↓ ligation circular                3' <------------5'
template              A A G A A A G A A A A G
(SEQ ID NO: 14)    G                          A
                  G                            C
                 A                              T
                  G                            A
                   G                          G
                    A A G A A A G A A A A G dNTP's           | rolling
        Klenow enzyme    | circle
        primer (5'-GATCCTTTT) | synthesis
                         ↓

5'--- GATCCTTTTCT TCTTCCTCC TTCTTTCTTT TCTGATCCTT TTC ---

(SEQ ID NO:15)

-continued

Scheme III

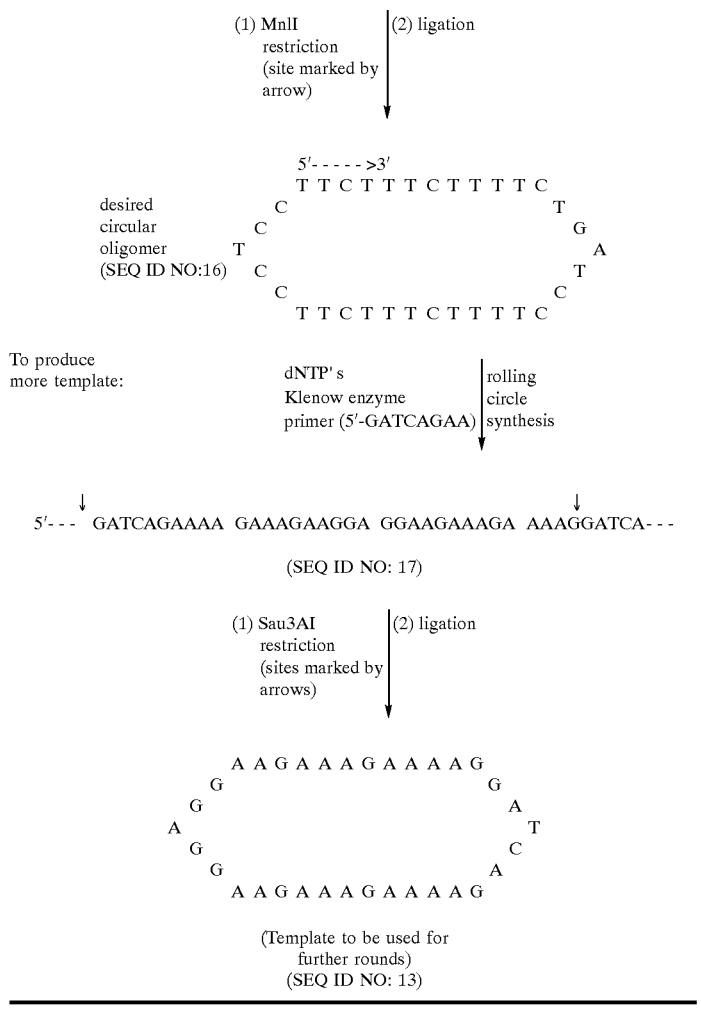

Example 5

Closure of Linear Oligomer Into Circular Form

DNA oligomers were synthesized on a Pharmacia LKB Gene Assembler Plus using standard β-cyanoethyl phosphoramidite chemistry as described in S. L. Beaucage et al., *Tetrahedron Lett.*, 22, 1859 (1981), which is incorporated herein by reference. The oligomer to be ligated (34-mer) had the sequence 5'-pAAAAGAAAGA AGGAGGAAGA AAGAAAGGAT CAG (SEQ ID NO: 18), and was 5' phosphorylated using Phosphate-On™ reagent (available from Cruachem, Sterling, Va.), whereas the shorter adaptor oligomer (8-mer) was left with hydroxyl termini. The template 34-mer was designed to include the single-stranded version of a double stranded restriction enzyme site such as that for Sau3AI (GATC). The adaptor 8-mer had the sequence 5'-TTTTCTCG, and was designed to be complementary to 4 bases at each terminus of the template 34-mer, thus bringing the ends into proximity upon binding.

The 5'-phosphorylated oligomers were chemically ligated to produce primarily DNA circles using EDC. A typical preparative reaction contained up to 100 μM target and 100 μM adaptor in a 10 mL reaction containing 200 mM EDC, 20 mM $MgCl_2$, and 50 mM 2-(N-Morpholino) ethanesulfonic acid (MES) buffer (pH 6.1, obtained from Sigma Chemical Co., St. Louis, Mo.). To keep the concentration of target oligomer low enough to favor intramolecular reaction (circularization) over intermolecular reaction (multimerization), up to 1 μmol of prescribe oligomer dissolved in 1 mL of water was added to the other reagents (9 mL at 10/9 final concentration) at 4° C. over a period of 50 hours with stirring, using a syringe pump to carry out the addition. Reaction was continued for an additional 16–24 hours after addition was complete to promote maximal reaction.

Products were recovered by precipitation with 30 mL of ethanol in the presence of 100 μg of rabbit muscle glycogen carrier (Sigma Chemical Co., St. Louis, Mo.) and purified by preparative gel electrophoresis. Yields were calculated from absorbence measurements at 260 nm using extinction coefficients calculated by the nearest neighbor method.

Example 6

Synthesis of Single-Stranded Multimers Complementary to a Circular Template DNA circles synthesized as described in Example 5 were used to direct the primed synthesis of complementary multimers by the rolling circle method. The primer oligonucleotide was annealed to the template circle in a reaction consisting of 1 μL of 100 μM template circle, 1 μL of 100 μM primer, and 2 μL of 5× Klenow reaction buffer (335 mM Tris(hydroxymethyl)aminoethane)-HCl (pH 7.4), 34 mM MgCl$_2$, 25 mM dithiothreitol, and 250 μg/ml bovine serum albumin). This mixture was cooled from 25° C. to 4° C. over several hours and then either kept on ice or frozen for future use. The reaction mixture contained the annealing reaction (4 μL), 4 μL of 50% polyethylene glycol 8000 (PEG 8000), 1 μL mixed deoxyribonucleotide triphosphates (specifically this was a mixture of dATP, dTTP, dGTP, dCTP (sodium salts) each at 2 mM), and 1 μL of 2 U/μL Klenow fragment of DNA Polymerase I (United States Biochemical) and was assembled on ice. Synthesis was allowed to proceed for 1 hour at 0° C. and then for 6 hours at 37° C. Product multimers were recovered as a pellet by centrifugation at 10,000 rpm for 10 minutes at room temperature in a microcentrifuge.

Example 7

Enzymatic Cutting of Linear Multimers into Oligomers

Single-stranded multimers containing a restriction enzyme site were cleaved using the appropriate restriction enzyme at a temperature that allowed transient hybridization between restriction enzyme sites in either an intermolecular or intramolecular fashion to create a double stranded site. In the case of multimers containing the recognition site for Sau3AI, digestion of the multimers produced from the standard synthesis reactions described in Examples 5–7 was done as follows.

The PEG 8000 precipitate was dissolved in 10 μL reaction buffer (as recommended by the manufacturer of Sau3AI) containing 1 unit of Sau3AI (New England Biolabs, Beverly, Mass.). Digestion was allowed to proceed overnight at 25° C. and products were analyzed by electrophoresis on a 20% polyacrylamide, 8 M urea denaturing gel. DNA was visualized by staining with methylene blue (Sigma Chemical Co.). The principal product had gel mobility identical to that of an authentic 34-mer, and had the sequence 5'-pdGATCCTTTTCT TTCTTCCTCC TTCTTTCTTT TCT (SEQ ID NO:19).

Example 8

Chemical Cleavage of Linear Multimers

This method can be used when the desired oligomer contains only one, two, or three different bases. An unused base is then incorporated into the multimer once at the end of every oligomer unit. For example, if the desired oligomer contains only C, A, and G bases, then the corresponding circular template will contain only the complementary G, T, and C bases; a single A base will be added at the site between the start and end of the desired sequence. The multimer transcript will consist of repeats of the desired sequence separated by a single T at each unit. Submitting this multimer to Maxam-Gilbert "T" reaction/cleavage conditions, as disclosed in J. Sambrook et al., *Molecular Cloning*, 2nd ed., Chapter 13; Cold Spring Harbor Press, 1989, incorporated herein by reference, results in cleavage of the chain at each T, with loss of the T base, and leaving the desired oligomers with phosphates on the ends.

Linear multimer can be isolated by pelleting from the transcription reaction as described above in Example 6. To confirm success of the rolling circle reaction, a small portion can be checked for length on an analytical scale by agarose gel electrophoresis, using markers of known length. Cleavage is then carried out on the isolated multimer, using standard Maxam-Gilbert-type conditions (scaling up as necessary for preparative amounts of DNA). The product oligomer can be isolated by ethanol precipitation.

For example, the sequence 5'-dCGAGAAAAGA AAGAAGGAGG AAGAAAGAAA AGA (SEQ ID NO:20) (a 33-mer) is the desired oligomer. The circular template then has the sequence (SEQ ID NO:21):

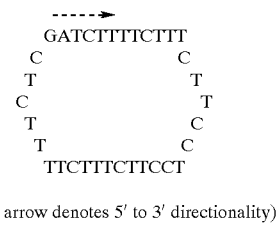

(the arrow denotes 5' to 3' directionality)

The rolling-circle reaction can be carried out as described above in Examples 1 and 6 (on larger scale), using the primer sequence 5'-dAAAGACG. This results in isolation of 50 mg of multimer after pelleting. Treatment of this product with hydrazine under Maxam-Gilbert conditions, followed by piperidine treatment, gives a reaction solution containing the desired monomer oligomers. Ethanol precipitation gives the isolated oligomer as desired. If necessary, this product can be further purified by reverse-phase, ion exchange, or gel filtration chromatography.

Example 9

Light-Induced Cleavage of Linear Multimers

In this method, light is used to induce multimer chain cleavage at a specially modified base, which occurs once at the end of every oligomer sequence in the multimer. This modified base contains a photolabile group, such as ortho-nitrobenzyl. When flashed with light, this group falls off and induces reaction to make the nucleoside anomeric bond itself labile to hydrolysis. Further piperidine treatment induces chain cleavage with loss of this base, as with Maxam-Gilbert methods.

This base may be a modified analog of one of the four natural bases, and in this case is coded for in the circular template by its natural complement. An example of a modified nucleotide base which can be made base-labile by irradiation with light is a pyrimidine (thymine or cytosine) which has been modified by an O-nitrobenzyloxycarbonyl-hydrazinoethyl group. UV irradiation induces loss of the O-nitrobenzyl group followed by decarboxylation, leaving the C5-hydrazinoethyl group. The hydrazine moiety reacts spontaneously with the pyrimidine base to which it is attached, making it labile to hydrolysis. Hydrolysis and multimer chain cleavage is carried out as described in Example 10.

Alternatively, this base is a nonnatural nucleotide which pairs with another nonnatural base. An example of such a nonnatural pair is the iso-C/iso-G pair described in J. Piccirilli et al., *Nature*, 343, 33 (1990), which is incorporated herein by reference. Use of such a nonnatural pair allows incorporation once per unit without placing requirements or restrictions on the use of the four natural bases in the desired sequence.

Example 10

Chemical Cleavage of Linear Multimers by Incorporation of a Nonnatural Activated Base The circular template is constructed to contain one nucleotide at the end of each coded oligonucleotide which is not contained within the desired oligomer sequence. This nucleotide codes for a nonnatural nucleotide which will be incorporated between each repeated oligomer sequence in the multimer.

This nonnatural nucleotide contains synthetic modifications which allow it to be cleaved selectively, leaving the desired DNA sequences untouched. Cleavage is carried out by addition of a chemical reagent to solution which reacts selectively with the nonnatural nucleotide base, phosphate, or ribose moiety.

In the case where the nonnatural activated nucleotide is a synthetic analog of a natural base, it will be coded for by the natural pair of that base. For example, if the nonnatural nucleotide is a synthetically modified deoxyadenosine, then it will be coded for by a thymidine in the circular template. In that case, the desired oligomer contains any combination of C, T, and G bases, but not A bases.

In the case where the nonnatural activated nucleotide does not pair with any of the natural bases, but instead pairs with a second nonnatural base, the activated nucleotide is coded for by the second nonnatural base in the template circle. For example, if the nonnatural activated base is a modified analog of deoxyisoguanosine, then it will be coded for by a deoxyisocytidine in the circular template. In that case, the desired oligomer may contain any of the four natural bases.

An example of a nonnatural activated nucleotide which is a synthetic analog of a natural base is described below. 8-allyldeoxyadenosine 5'-triphosphate (ADA) is incorporated into the linear multimer once at the end of each desired oligomer sequence. The ADA nucleotide is coded for by a thymidine in the template circle. The linear multimer is then cleaved in the following manner: an activating reagent is added to a solution of the multimer, which reacts with the three-carbon allyl moiety, producing an alkylating functional group at the end of the three-carbon chain. This functional group then spontaneously alkylates the N-7 position of the purine ADA base, leaving a positive charge on the base. It is now labile to hydrolysis, and the multimer is activated for chain cleavage. A second example of such a base is N-4-allyldeoxyadenosine, which will react in similar fashion.

Hydrolysis and multimer cleavage is carried out by the Maxam-Gilbert method: the activated multimer is dissolved in 10% aqueous piperidine and is heated to 90° C. for 30 min. The solution is frozen and lyophilized and is redissolved in water and dialyzed to remove the small products of cleavage from the desired oligomers. These product desired oligomers contain phosphates at both ends. If no phosphates are desired, they can be removed enzymatically.

An example of a nonnatural activated nucleotide which does not pair with any of the natural bases is 8-allyldeoxyisoguanosine (ADIG). It is cleaved by the same methods described in the preceding paragraph. Further examples include all purine structures which contain an N-S and an N-7 moiety.

An example of an activating reagent which reacts with the allyl group is N-bromosuccinimide. Other examples include is molecular bromine ($Br_2$), molecular iodine ($I_2$) and various epoxidizing reagents.

A second example of a nonnatural activated nucleotide is (N4)-mercaptoacetyl-deoxyadenosine, where the mercaptan is protected by a protecting group such as t-Butylthio. When this activated nucleotide is present in the multimer it can be made labile to hydrolysis by the following procedure: to a solution of the multimer is added sodium borohydride or dithiothreitol to deprotect the mercaptan. The multimer is dialyzed to remove the small reaction products. An activating reagent is then added which reacts with the mercapto group to make it a good leaving group. The N7 of the purine then is spontaneously alkylated, making it labile to hydrolysis. Hydrolysis and multimer cleavage is then carried out as described above.

An example of an activating reagent for the mercaptan is acetic anhydride. This forms the acetylmercapto group, which is a good leaving group. A second example of an activating group is disodium chlorophosphate. A third example is 1-(3-dimethylaminopropyl)-3 ethylcarbodiimide HCl.

Example 11

Chemical Cleavage of Linear Multimers by Catalytic Alkylation of N7 of an Extra Purine This procedure requires no synthetically modified bases to be incorporated into the multimer. The circular template is constructed to contain one additional pyrimidine nucleotide (Ⓒ is preferred) at the end of each coded oligonucleotide. After rolling circle synthesis, the multimer contains an extra purine nucleotide (G is preferred) in between each desired oligomer.

This extra purine can be made labile to hydrolysis in the following manner. An oligonucleotide modified with a thioether group is added to a solution of the multimer. This oligonucleotide is complementary to part of the desired oligomer sequence in the multimer. The thioether is thus brought into close proximity to the N7 group of the extra purine nucleotide. The proximity is controlled by careful choice of the sequence of the thioether-oligonucleotide and by the chemical structure of the chain carrying the thioether. After hybridization has occurred, an activating reagent is added to solution. This reagent alkylates the thioether to produce a reactive sulfenium group ($SR_3^+$). This group spontaneously alkylates the N7 group of the extra purine, and the product of the reaction is the alkylated purine in the multimer, and the thioether-oligonucleotide, which can then catalyze alkylation at another extra purine.

Hydrolysis and multimer chain cleavage is carried out as described in Example 10. Examples of activating reagents are dimethyl sulfate, S-adenosylmethionine, dimethylpyrocarbonate and trimethyl sulfur chloride. A further example of a thioether-oligonucleotide is a circular oligonucleotide modified with a thioether at the 5-position of a pyrimidine base. The preferred pyrimidine base is the same one that codes for the extra purine. The circular oligonucleotide contains the same sequence as the template circle.

Another example of this method is the case in which the thioether oligonucleotide is the same as the template circle. In this case, rolling circle synthesis is carried out and at the end of (or during) the reaction the chemical activating reagent is added to solution to make the multimer labile to hydrolysis.

Example 12

Use of a Randomized Circular Oligomer in Screening for Biological Binding, and Identification of a Circular Sequence as a Pharmaceutical Agent A pharmacological target molecule is selected for screening. This target will depend on the disease to be treated, and it is a target which, when strongly complexed at an active site, will result in a pharmacologically desirable effect. Examples of pharmacological target molecules and the expected result of binding include: binding of HIV reverse transcriptase or HIV tat protein for inhibition of the AIDS virus; binding of FK506 binding protein for activity as an immunosuppressant; binding of squalene synthase for a cholesterol lowering effect; binding of mutated p53 protein for an antitumor effect; binding of mutated ras protein for an antitumor effect; binding of the bcr-abl mutant protein for an antileukemic effect; binding of influenza coat proteins for an anti-influenza effect; binding opiate receptors for an analgesic effect; binding to a transcription repressor protein to enhance transcription of a specific gene; binding to the multidrug resistance protein to suppress resistance to anti-cancer drugs; binding to d-ala-d-ala to inhibit bacterial growth; binding to d-ala-d-lactate to inhibit growth of vancomycin-resistant enterococcus; binding of rhinovirus coat proteins for treatment of common cold; binding of resin to lower blood pressure; binding bcl-2 protein to induce apoptosis in cancer cells; binding of thrombin to inhibit clotting; and binding of NO-synthase to inhibit septic shock.

An affinity column is then prepared. The pharmacological target molecule is attached to a commercially available activated solid support using procedures suggested by the manufacturer. Usually this consists of simple mixing of the support with the molecule of choice.

A circular oligonucleotide pool is constructed, which is a series of same-size molecules that contain a randomized domain of 10–100 bases and a domain of known sequence of 8–40 bases in length. This pool is eluted down the affinity column under approximately physiological conditions of pH and ionic strength. Fractions are collected of this eluent. Nucleotide content can be measured by monitoring the eluent stream for absorbence at 260 nm, or individual fractions can be checked. The distribution of oligomers in the fractions will depend on each molecule's binding ability: early fractions will contain the majority of molecules, which have low affinity for the target molecule. Later fractions will contain fewer oligomer sequences which have better binding ability. The latest fractions which contain DNA can be collected; these will contain the best-binding subset of sequences. This last enriched pool will then be subjected to amplification using the rolling-circle procedure; alternatively, they can be linearized and a PCR procedure can be used. The amplified products are re-cyclized and subjected to further rounds of affinity selection and amplification. After 3–30 rounds the selected sequences will be enriched in only a few strong binding sequences. The successful molecules in this pool can be identified as to sequence and structure, and they can be tested for inhibition of the specific target's function in an in vitro or in vivo assay. The most inhibitory molecules may be used as pharmaceutical agents. Alternatively, the structure can be analyzed, and a synthetic molecule can be synthesized which mimics structurally the important parts of the selected oligonucleotide. This new synthetic molecule may be used as a pharmaceutical agent.

The successful subset of enriched circular molecules can be identified as to sequence in the following way: They are used as template circles in a rolling circle synthesis to produce a complementary set of multimers. A short linear primer is used (along with a DNA polymerase and the NTP's) to make a linear complement of the multimer set. A restriction enzyme is then used to cleave the set into short duplexes having sticky ends.

At the same time, a convenient plasmid vector is chosen which contains this same restriction site, and the short duplexes can be cloned using standard procedures. For example, the plasmid is also cleaved by this restriction enzyme to make a linear duplex with sticky ends. The set of short duplexes is mixed with this linear plasmid, and ligated with T4 DNA ligase. This will produce a set of new circular plasmids with the enriched circle sequences inserted. These can be transfected into E. coli according to standard procedures, plated and allowed to form colonies. Each colony can be identified by sequencing using standard procedures.

An alternative method for identifying sequence of the enriched circular oligomers is to linearize them with a restriction enzyme and sequence them directly using the Sanger dideoxy method. This will identify positions having strongly conserved bases and preferences in variable bases, and will show base positions that have no strong preference.

Example 13

Design and Construction of Partially Sequence-Randomized Circular Oligomers for Selection and Screening The total length of the circular oligomers will be 30–200 nucleotides. They will contain three domains: left domain of known sequence (5–30 nucleotides); a sequence-randomized domain of 5–190 nucleotides; and a right domain of known sequence (5–30 nucleotides). When in circular form, the left and right domains will be adjacent to one another, with the right domain being 5' to the left domain In enzyme-linearized form, the left domain is at the 5'-end, followed by the random domain, and then the right domain. The initial synthesis is done using an automated synthesizer to construct a linear version of the oligomer with a phosphate on one end. Cyclization is carried out using the procedure described in Example 5. Alternatively, cyclization is carried out enzymatically, using T4 DNA ligase and a short adaptor oligomer which is complementary to the ends being joined, or using T4 RNA ligase without an adaptor.

To create the random domain using the synthesizer, two approaches can be taken. At the randomized positions, a fifth reagent bottle can be used which contains a mixture of the four phosphoramidites of the natural bases. A second approach is to use a synthesizer which can simultaneously draw reagents from more than one bottle at a time.

A randomized coupling step during DNA synthesis can be carried out with a completely sequence-random 1:1:1:1 mixture of the four phosphoramidites, or it can be any ratio of a mixture of two or more bases.

The design of the left and right domains requires the following features: the joining of the right and left domains creates a restriction enzyme site, and conversely, the cleavage of the circular oligomer with this enzyme creates a linear oligomer with the left domain on the 5' end and the right domain on the 3' end. The choice of restriction enzyme prefers the following features: the ability to cleave single-stranded DNA, and a recognition sequence of 5 bases or longer. One example is the enzyme BstN I, which recognizes the sequence 5 '-CCAGG, cleaving it after the two C's, and with single strand cleaving activity. If a circular oligomer contains this sequence, the enzyme will cleave it, leaving the sequence 5'-AGG on the 5'-end, and the sequence 5'-GG on the 3'-end.

In linearized form, the right (3') domain must be able to serve as a primer binding site (for dideoxy sequencing), and so should be 8–15 bases in length to allow sufficient binding. The right and left domains should each be at least four bases in length to allow an adaptor oligomer to bind for the cyclization reaction. One skilled in the art can choose added bases which are required for these purposes in addition to the restriction sequence.

For rolling circle synthesis using a partially randomized circle, the sequence of the primer oligomer will be complementary to at least eight contiguous bases of the combined right and left domains.

Example 14

Effect of Circle Size on Rolling Circle DNA Synthesis

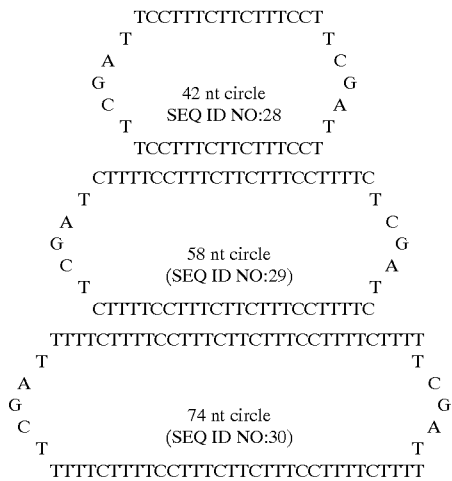

Successful rolling circle reactions using a 34 nucleotide circular template were described in Example 6. In order to investigate the effects of increasing size on the reaction, three larger circles 42-, 58-, and 74 nucleotides in length were tested. The primer sequence used was 5'-AGGAAAGAAGAAAGGA (SEQ ID NO:31) Conditions for the reaction were as follows: 1.0 μM circle, 1–5 μM cold primer, 1.0 mM dNTP's, 2.5 units Klenow enzyme (USB), in a buffer containing 50 mM Tris.HCl (pH 7.5), 10 mM MgCl$_2$, 1 mM DTT, and 50 μg/mL BSA. The total reaction volume was 20 μL. The reaction was incubated for 3 hours at 37° C. and then quenched by addition of denaturing formamide loading buffer (80% formamide, 10 mM EDTA). The results were analyzed by polyacrylamide denaturing gel electrophoresis.

All three circles successfully extended the primer. Further, repetitive banding patterns appeared in the lanes corresponding to the RNA synthesized using each of the three circles. These banding patterns strongly indicate that the circles were indeed used as the RNA transcription template. The banding patterns did vary by circle size as predicted. Moreover, the lengths of the transcripts in all cases were about the same, in the general range of 1000–4000 nucleotides.

Thus, the rolling reaction was not sensitive to circle size over the range of about 28 to 74 nucleotides in size. It is remarkable that a circle as small as 28 nucleotides, which is considerably smaller than the polymerase itself, behaved as a good template.

Example 15

Comparison of Rolling Circle Reactions on Small Synthetic Circles and on Single-stranded Phage φX174

Standard rolling circle conditions as given in Example 6 were used to elongate primers complementary to the above three circles (42–74 bases in length) and to a single-stranded, 5386 nucleotide-long phage. The primer for the synthetic circles was 5'-AGGAAAGAAGAAAGGA (SEQ ID NO:31), and that for the phage was 5'TGTTAACTTCT-GCGTCAT (SEQ ID NO:32). Both primers were radiolabeled, and the reactions were run as before, using a 1 μM concentration of circle. The results were analyzed by 1% agarose gel electrophoresis, and a 1-kB marker ladder was used to evaluate sizes. Results of the experiment showed that the primers were successfully elongated in all four cases, and the products have fairly wide size distributions.

The reactions using the three synthetic circles as templates gave products with banding indicating a multimeric sequence. The lengths ranged generally from 500 to 2000 nucleotides, indicating the presence of multimers that are ~25–50 monomer units in length. The experiment using φX174 gave different results. The lengths of the products fell in the ~2000–8000 nucleotide range. Therefore, the products contained only ~0.5 to 1.5 monomers, since the template circle was ~5 kB in size.

The results establish that many more useful monomers can be produced from small synthetic circles than can be produced from a much larger naturally occurring circle. Further, the larger circle did not "roll" successively, that is, it did not progress substantially more than once around the circle. Possibly the duplex being synthesized inhibits the further progression of the polymerase after the first time around, as has been reported in the literature. The small circles are short enough that any duplex being formed is strained by the curvature, and tends to unwind spontaneously as synthesis progresses.

Example 16

Construction of a DNA Circle Containing a Randomized Domain

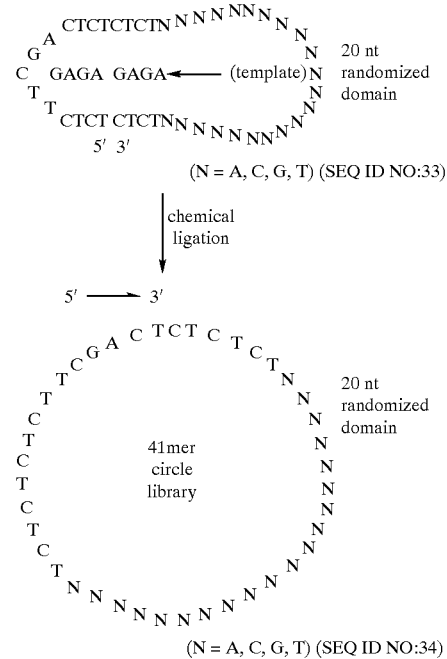

A 41-nucleotide DNA circle was constructed to have a 20-nt randomized domain as shown. The circle precursor contained a 5' phosphate and was designed to form a triple helical complex with a short purine-rich template as shown. The randomized part of the precursor was made using one bottle of mixed A, T, C, G phosphoramidites on the DNA synthesizer. Precursor (50 μM) and template oligomers (55 μM) were incubated for 7.5 hours at room temperature in a buffer containing 100 mM NiCl$_2$, 200 mM imidazole.HCL (pH 7.0), and 125 mM BrCN. The circular product depicted above was produced by the reaction and was isolated by preparative denaturing PAGE.

This product with its 20-nucleotide randomized domain represents a mixture of ~10$^{12}$ different circular DNA sequences. This mixture, or library, is suitable for subsequent selection/amplification experiments.

Example 17

Confirming the Multimer Sequence in Rolling Circle DNA Synthesis

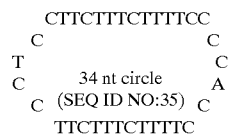

The above circle was used as template in a standard rolling circle reaction under conditions described in Example 6 above. The primer used was 5'-AAGAAAGAAAAG (SEQ ID NO:36). After the reaction, the products were analyzed by electrophoresis on a 1% agarose gel and visualized by staining. One of the dark bands, having a length of approximately 1000 nucleotides, was excised and the DNA recovered from the gel by simple elution. This DNA was then sequenced using Sanger dideoxy methods, using a primer of sequence 5'-pTTTCTTCCTCCTTCTTTCTTTTCCCCACCTTTTC (SEQ ID NO:37) (which corresponds to the precursor of the circle used as template). The sequencing results indicate that this approximately 1000-nucleotide length DNA was a multimer of the expected repeating monomer sequence. There was a minor background of other sequences, but it was clear that the major product was a multimer of the expected repeating monomer.

Example 18

Small Synthetic DNA Circles Act As Efficient Templates for RNA Synthesis

Small synthetic DNA circles can act as templates for RNA synthesis in addition to DNA synthesis. The following DNA circle was used as an efficient template for RNA synthesis:

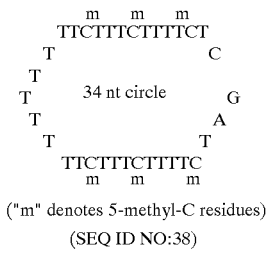

("m" denotes 5-methyl-C residues)

(SEQ ID NO:38)

Standard runoff transcription reactions using linear DNA template with a T7 RNA Polymerase promoter at the 5'-end of the sequence were carried out as described in Milligan et al., *Nucleic Acids Res.*, 15:8783 (1987). In some reactions the circular template depicted above was added, and extra long bands were found in some of the reaction tubes containing the circular template in addition to the linear template.

A control experiment was then carried out in which the linear runoff template was not included in the reaction tubes. Long RNA molecules were produced in the presence of circular template alone. This was especially surprising since the circular template did not contain any known promoter sequences.

Transcription reactions were performed using α-$^{32}$P-dUTP as a limiting nucleotide to allow efficient labeling of the RNA being synthesized. In the reactions containing circular template, an apparent repeating banding pattern was found, and most of the products found were longer than what a 15% gel could resolve. Further, the intensity of the bands resulting from the use of the circular template alone were approximately as strong as those produced by the linear promoter template alone. These results indicated that the two transcription reactions were roughly equivalent in efficiency.

Example 19

Rolling circle RNA Synthesis Does Not Require a Promoter 41-mer DNA circles containing a 20-nucleotide variable sequence domain were synthesized as described in Example 1. The 20-nucleotide variable sequence domain contained runs of $T_{20}$, $C_{20}$, $A_{20}$, and $G_{20}$. Some of the circles contained an optimized T7 RNA polymerase promoter: $N_{20}$=5'-CCCTATAGTG AGTCGTATTA (SEQ ID NO:39). These 41-mer circles were used to synthesize single-stranded multimers using the following conditions: 25 mM Tris-HCl, pH 8.1; 20 mM NaCl; 15 mM MgCl$_2$; 0.4 mM spermine4HCl; 100 μg/mL Acetylated BSA; 10 mM dithiothreitol; 12.5 U/mL RNase inhibitor (Promega); 0.5 mM each rATP, rGTP, rCTP; 0.27 μCi α-$^{32}$P rUTP; 1 μM template circle (AG2C1); 50 U T7 RNA Polymerase (New England Biolabs). Results of these rolling-circle reactions showed that circles containing $T_{20}$ and $C_{20}$ domains gave long RNAs; however, those with $A_{20}$ and G20 domains did not. It is likely that long A runs inhibit transcriptional elongation. This finding, in fact, has been reported previously in the literature. J. Tomizawa and H. Masukata, *Cell* 51:623 (1987). The poor elongation with the G20 run is likely due to the circle forming aggregates because of the G-rich sequence.

Finally, the data show that when a T7 promoter was present in the circle, only short RNAs were produced. This indicates that for some reason the rolling, or progression of the polymerase, was retarded by the promoter sequence. Thus, the rolling circle reaction of the present invention preferably works with circular templates that do not contain polymerase promoters. This ability to work better in the absence of polymerase promoters, along with the unusually small circle sizes, makes the process of the present invention different from natural transcription of circular templates. The circular templates of the present invention encode only the RNA of interest, not extraneous sequences that are normally found when sequences are transcribed from plasmids. Moreover, the products of the present method are single-stranded, not double-stranded as in natural transcription methods.

Example 20

Use of Different RNA Polymerase Enzymes for Rolling Circle RNA Synthesis

Four separate enzymes were tested for their ability to carry out transcription on 34-mer circular templates. The enzymes used were T7 (New England Biolabs), T3 (Promega), and SP6 (Gibco BRL) RNA polymerases derived from phages, and E. coli RNA Polymerase (Boehringer Mannheim). The working concentrations of the T7, T3 and SP6 polymerases were 2U/µl and the working concentration for E. coli RNA Polymerase was 0.3 U/µl. The synthesis reactions were performed under the conditions set forth in Example 19 above. No auxiliary proteins (such as DNA unwinding protein, cisA protein, or rep protein) were added to the reactions. Products were examined by both polyacrylamide and agarose gel electrophoresis, and were internally radiolabeled using limiting $\alpha$-$^{32}$P-dUTP.

All four enzymes worked well at rolling transcription. The only observable difference in efficiency among the different enzymes was that the E. coli RNA Polymerase gave somewhat longer RNA products than the other three enzymes.

Example 21

Rolling Circle RNA Synthesis in an Extract from Eukaryotic Cells

Eukaryotic RNA polymerases were also tested for their ability to carry out transcription on circular templates. A commercially available nuclear extract from Drosophila (Promega) was added to reactions both containing and lacking a 34-mer template under the following recommended transcription conditions 7.5 mM HEPES buffer, pH 7.6; 60 mM potassium glutamate; 3.75 mM MgCl$_2$; 0.03 mM EDTA; 1.5 mM DTT; 3% glycerol; 0.5 mM each rATP, rCTP, rGTP; and 0.06–0.02 mM rUTP. The concentration of circular template was 3 µM. When no circular DNA templates were added, the extract can by itself give a small amount of new radiolabeled RNA. However, when a 34-nucleotide circle was present, a much larger amount of RNA was observed. These RNA molecules were too long to be resolved by polyacrylamide gel electrophoresis. Two experiments were performed to confirm that the RNA transcription was due to rolling transcription. First, a control reaction was performed using the linear precursor to the circle, and the result was very little RNA. This suggested that the circular structure was essential for the RNA synthesis. Second, the concentration of UTP was successively lowered, producing observable, regular banding patterns indicative of repetitive sequences. This result also suggested that the circular template was being used in rolling transcription. Thus, RNA polymerases from higher organisms can use small circles as templates. It is therefore likely that if such circles are delivered into living cells, the circles will act as templates for the production of RNA.

Example 22

Initiation Sites and Sequences of RNA Multimers

The circle shown in Example 18 was used as a template in a series of rolling circle transcription reactions in which varying amounts of rUTP were added. The conditions for the reactions were as follows: 25 mM Tris-HCl, pH 8.1; 20 mM NaCl; 15 mM MgCl$_2$; 0.4 mM spermine4HCl; 100 µg/mL Acetylated BSA; 10 mM dithiothreitol; 12.5 U/mL RNase inhibitor (Promega); 0.5 mM each rATP, rGTP, rCTP; 0.27 µCi $\alpha$-$^{32}$P rUTP; 1 µM template circle (AG2C1); 50 U T7 RNA Polymerase (New England Biolabs). The concentration of rUTP was varied in the series of reactions from 0 to 60 mM. The reactions were carried out in a reaction volume of 15 µL for 1.5 hours at 37° C.

Polyacrylamide gel analysis for the products showed that as the limiting nucleotide (rUTP) decreased, regular repeating banding patterns became evident on the autoradiogram. The repeating unit corresponded to 34 nucleotides, the length of the template. Closer examination showed that the dark bands appeared largely at sites where a C residue was present in the circle. Thus, initiation of transcription is occurring primarily at C template residues, using rGTP as the first nucleotide in the transcribed RNA strand.

Subsequent experiments were performed with circles containing 28 T's and only one C nucleotide. These experiments showed that it was also possible to initiate transcription at a T (using rATP as the first nucleotide). In general, a circle is likely to require at least a short pyrimidine-rich domain so that transcription can initiate.

The above results also provide strong evidence that the circle is successfully serving as the template for a desired RNA multimer. All other circles have shown similar banding patterns (although with different sequences and lengths) when limiting UTP is present. A longer band about 150 nucleotides in length was isolated from an analogous transcription reaction and then treated with RNase T1. Results showed bands as predicted from the expected nucleotide selectivity of this enzyme.

Example 23

Circles Encoding Repeating Stem-loop Antisense RNAs

It has previously been shown (E. D'Souza and E. Kool, J. Biomolecular Structure and Dynamics, 10:141 (1992)) that stem-loop DNA structures can bind tightly to single-stranded DNA targets by triplex formation. Similar binding of single-stranded RNA targets is possible by use of stem-loop RNA structures. These stem-loops bind tightly to a disease-related mRNA or viral RNA and inhibits mRNA splicing, mRNA translation, or viral replication. A 53-mer circle containing a binding domain that encodes a binding sequence that can bind to HIV-1 gag gene near the start codon and a structural domain that encodes a stem-loop sequence is constructed as shown below. When transcribed by the rolling circle method it produces a repeating sequence which folds into multiple stem-loop structures. These stem-loop structures then bind tightly to a targeted RNA, inhibiting gag translation in vitro. When added to HIV-1 infected cells it enters the cell by endocytosis, is transported to the nucleus, and is transcribed by the rolling circle process. The resulting stem-loop multimer inhibits viral replication by binding multiple HIV RNAs at the gag gene site.

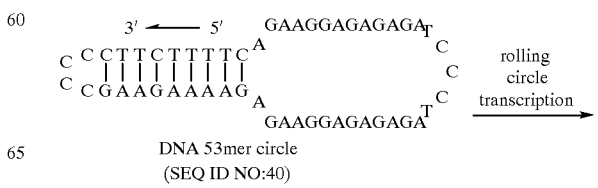

DNA 53mer circle
(SEQ ID NO:40)

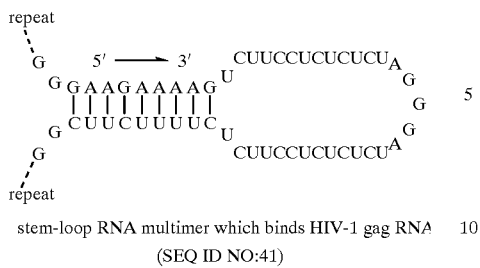

stem-loop RNA multimer which binds HIV-1 gag RNA
(SEQ ID NO:41)

Alternatively, the 53mer circle encodes a repeating RNA multimer, shown below, which folds into stem-loop structures which bind bcr-abl mRNA from the Philadelphia chromosome mutation leading to chronic myeloid leukemia. The stem-loops bind a sequence directly at the L6-type junction, thus causing inhibition of translation of this mRNA and inhibiting growth of the leukemic cells.

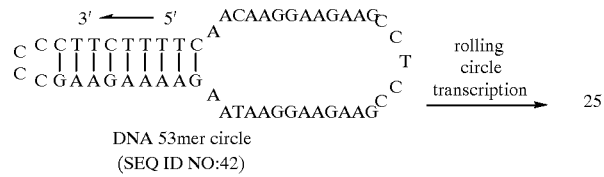

DNA 53mer circle
(SEQ ID NO:42)

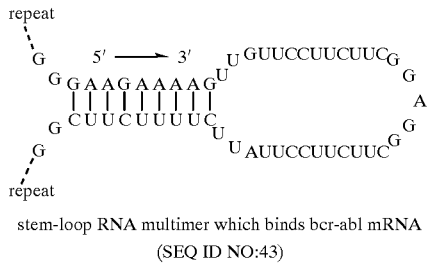

stem-loop RNA multimer which binds bcr-abl mRNA
(SEQ ID NO:43)

Example 24

Circles Encoding RNA Hairpin Decoy Sequences

A circle is constructed which encodes multimer RNAs that fold into repeating hairpin structures. Hairpin structures are double helical regions formed by base pairing between adjacent (inverted) complementary sequences in a single strand of RNA or DNA. These hairpins correspond to known binding sites for viral proteins that are important for viral replication. This binding to the multimer hairpins causes these proteins to be sequestered, rendering them unable to activate viral replication efficiently. Examples of known proteins in HIV-1 that could be bound by this method are the tat protein, which normally binds TAR RNA, and rev protein, which normally binds RRE RNA. U. Vaishnav and F. Wong-Staal, *Ann. Rev. Biochem.*, 60, 577 (1991).

A specific sequence is shown below. This 45mer circle encodes repeating multimers of RNA that fold into hairpins capable of binding the HIV-1 rev protein tightly. It contains a binding site capable of binding the HIV-1 rev protein and a structural domain that encodes a hairpin sequence. Addition of these DNA circles to HIV-1-infected cells leads to inhibition of viral replication.

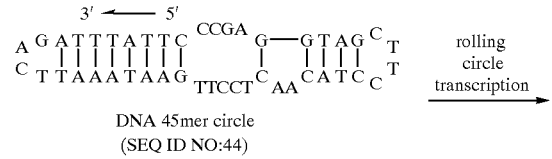

DNA 45mer circle
(SEQ ID NO:44)

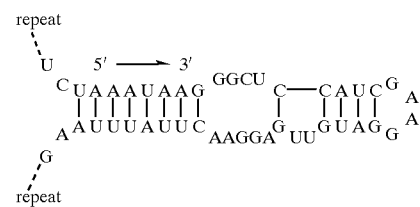

hairpin RNA multimer which bindsHIV-1 rev protein
(SEQ ID NO:45)

Example 25

Circles Encoding Ribozymes which Cleave RNA

Another way to inhibit translation of specific genes is to generate short RNA ribozymes which cleave specific RNA sequences in a given gene, thus leading to gene inactivation. Hammerhead-type and hairpin-type ribozymes can be constructed from short RNAs of about 14–75 nucleotides in length. Circular DNAs are constructed for encoding specific ribozyme sequences. These circles contain a binding sequence that can bind a target in RNA and a structural domain that encodes the ribozyme. A circle can encode a repeating ribozyme multimer which remains concatenated but still folds into active ribozymes. Alternatively, a circle can encode both a ribozyme and its cleavage site. In this second case the multimeric ribozyme first cleaves itself into monomer-length ribozymes; then it goes on to cleave the target mRNA or viral RNA in trans.

For example a 49mer DNA circle is made that encodes a hammerhead-type ribozyme and its cleavage site which corresponds to the abnormal junction of the Philadelphia chromosome bcr-abl mRNA. When the DNA circle is added to CML cells it is transcribed by the cellular machinery into a multimeric RNA. This multimer first cleaves itself successively into shorter units (as short as monomer), and these shorter units cleave the mutant RNA. Thus, the circular DNA assists in inhibiting leukemic cell growth.

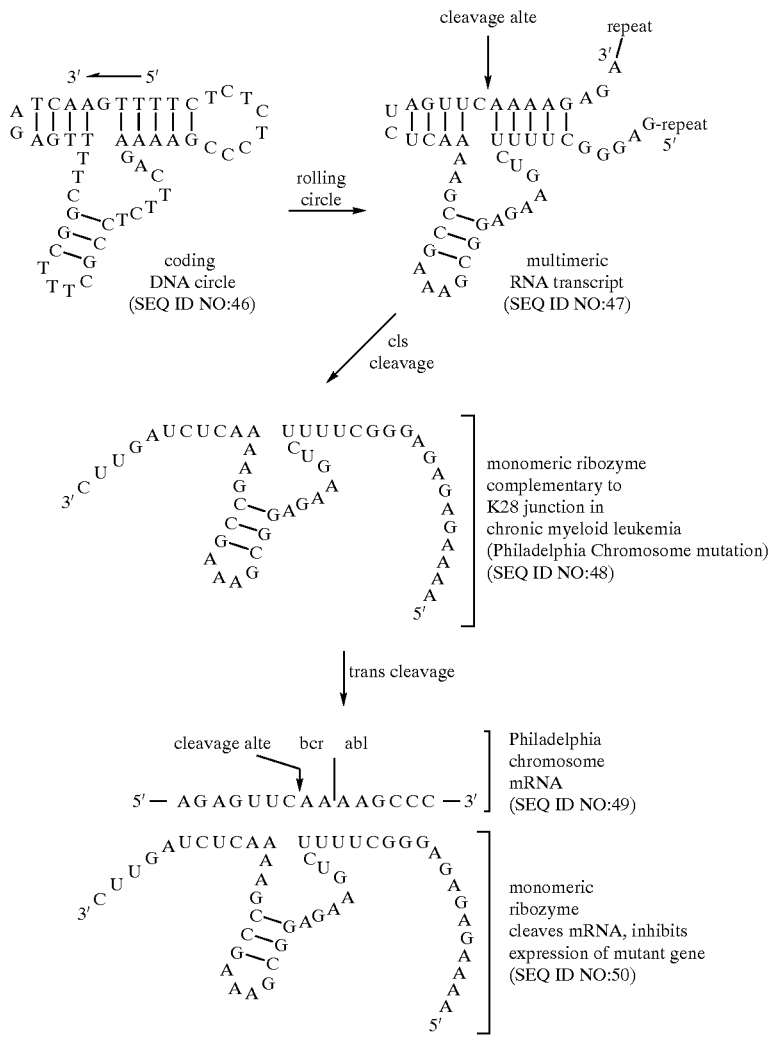

Example 26

Figure 4:
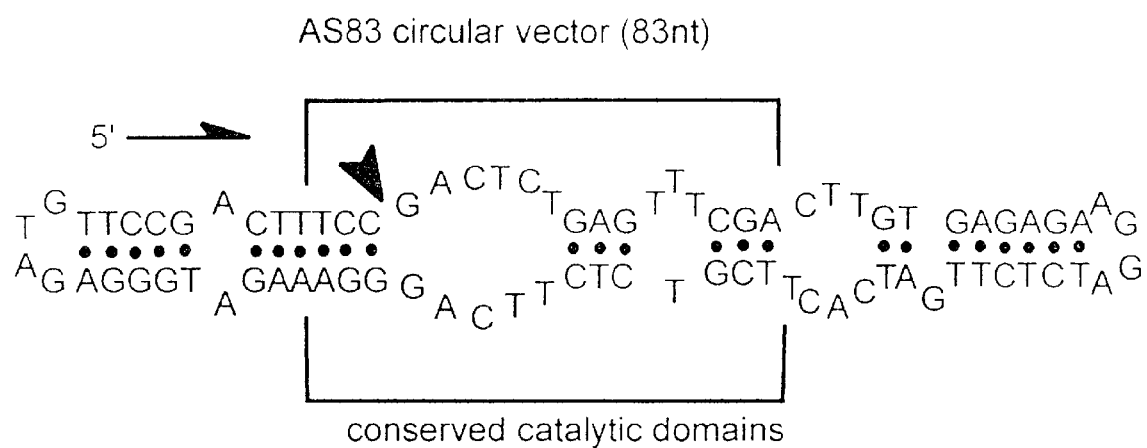
FIG. 4. Sequence of the synthetic AS83 DNA nanocircle (SEQ ID NO:51), which contains sequences mimicking catalytic segments of the Avocado Sunblotch Viroid. The arrowhead marks the encoded self-cleavage site of hammerhead-motif RNA after transcription; the horizontal arrow denotes 5' to 3' strand orientation; and the boxed portion indicates sequences encoding catalytically active RNA and substrate for cleavage.
Figure 5:
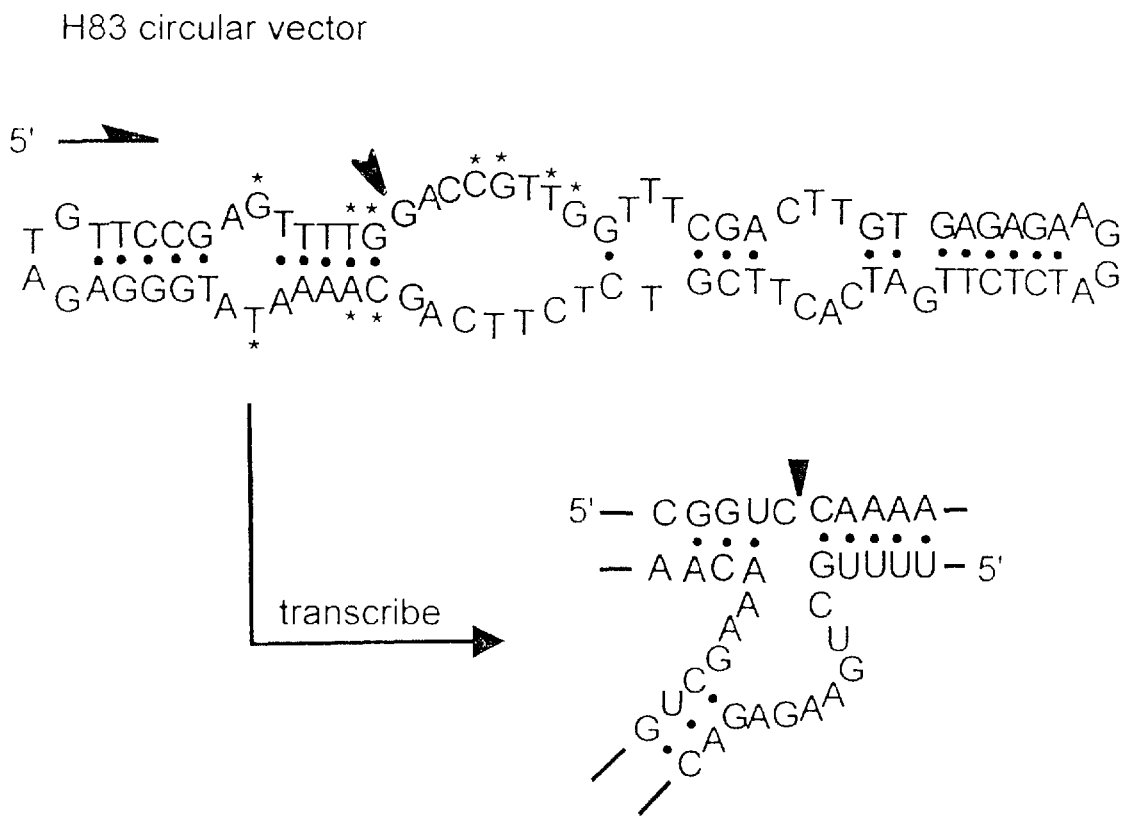
FIG. 5. Sequence of the synthetic H83 nanocircle (SEQ ID NO:52), which encodes a ribozyme targeted to nucleotides 1751–1764 of HIV-1 gag. The H83 sequence was designed by changing specific nucleotides (marked by an asterisk) in the encoded catalytic domains of AS83 nanocircle; the encoded cleavage site is denoted by an arrowhead. The sequence of the catalytic H83 transcription product (SEQ ID NOS:53 and 54) is also shown.
Figure 6:
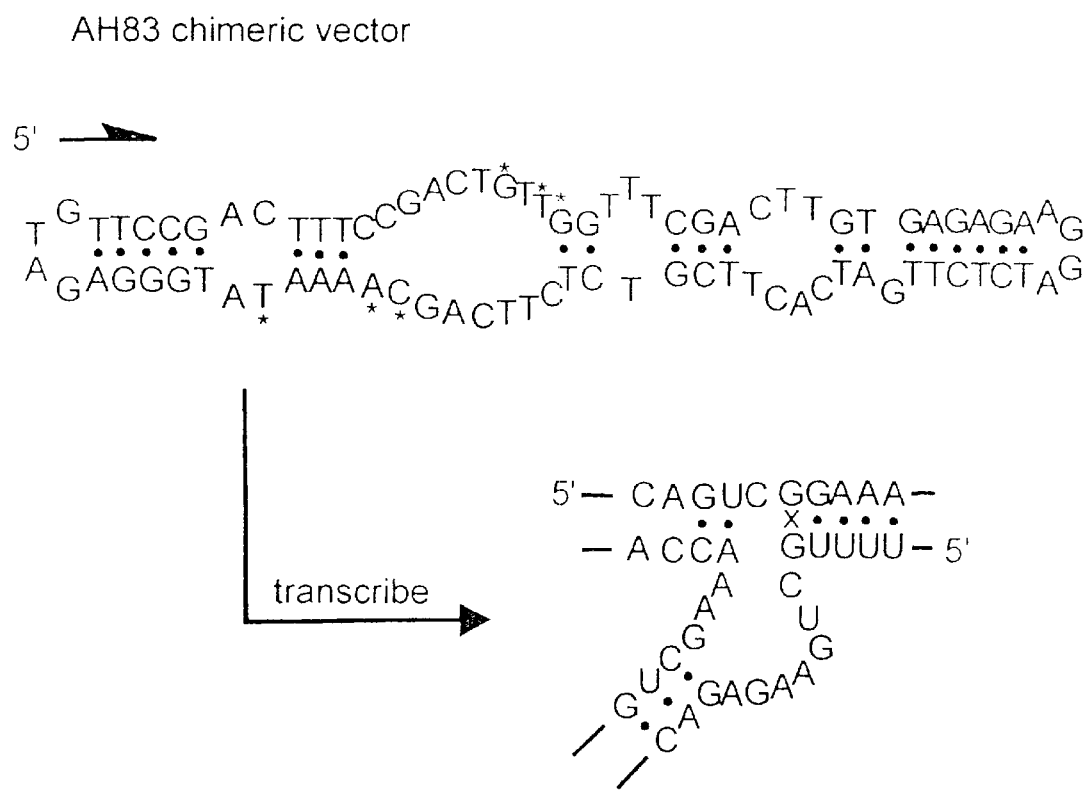
FIG. 6. Sequence of the synthetic non-autolytic AH83 chimera (SEQ ID NO:55), in which the catalytic domain is that of the H83 nanocircle but the cleavage site is that of AS83 nanocircle. The sequence of the catalytic AH83 transcription product (SEQ ID NOS: 56 and 57) is also shown.
Figure 7:
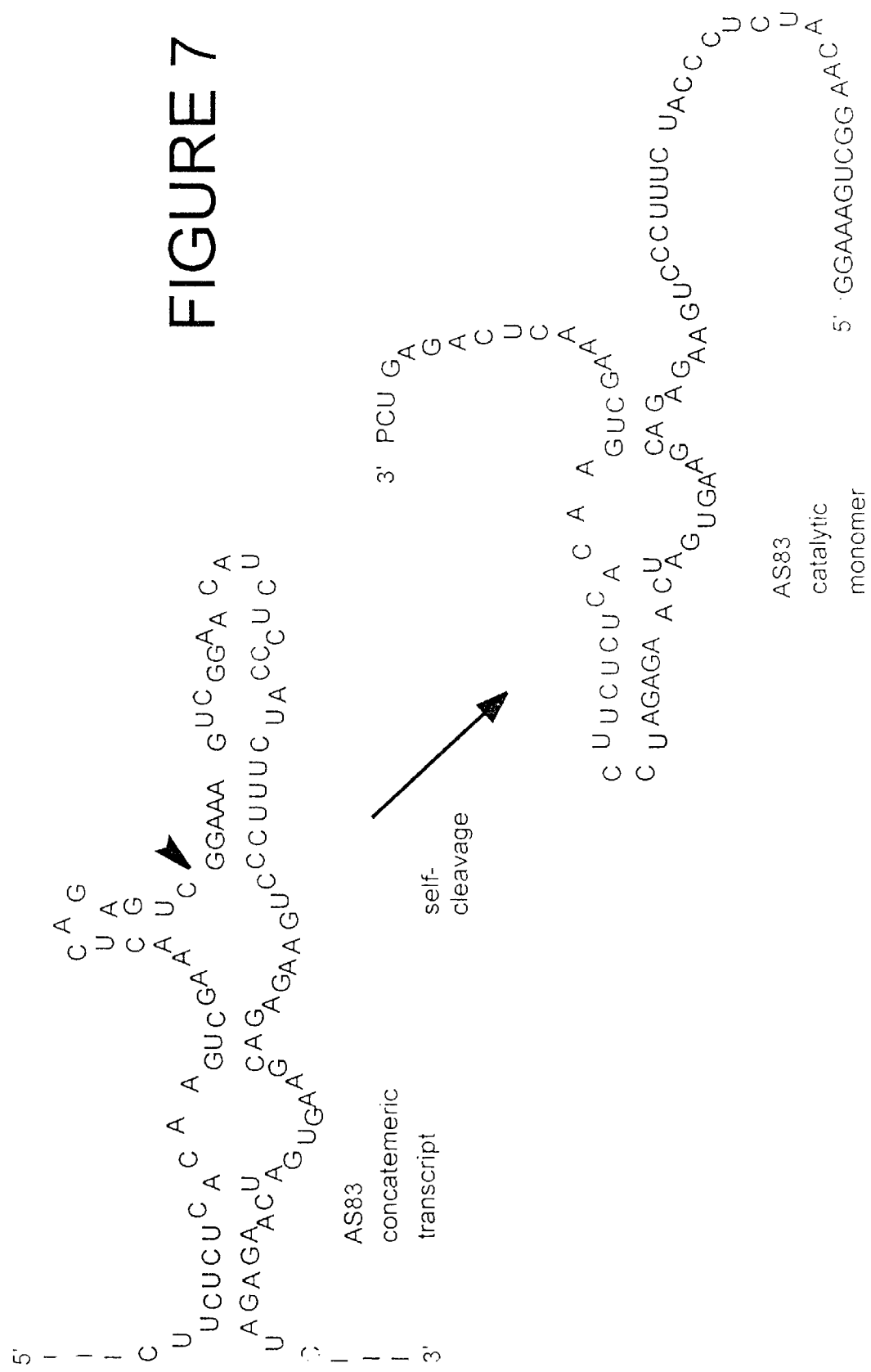
FIG. 7. Concatemeric RNA transcript produced from transcription of AS83 nanocircle (SEQ ID NO:51) folds to form a string of hammerhead-motif RNAs (SEQ ID NOS:58), which then self-cleave at the indicated site to ultimately yield oligoribonucleotide monomers 83 nucleotides in length (SEQ ID NO:59).

Construction of Circular DNA Templates for Use in Generating Catalytic RNAs Linear oligodeoxynucleotides were synthesized on an Applied Biosystems 392 DNA synthesizer using the standard DNA cycle. Construction of an 83-nucleotide circle (AS83) (FIG. 4) was accomplished by enzymatically ligating a 41mer (5'pGAGATGTTCC GACTTTCCGA CTCTGAGTTT CGACTTGTGA G) (SEQ ID NO:62) and a 42mer (5'pAGAAGGATCT CTTGATCACT TCGTCTCTTC AGGGAAAGAT GG) (SEQ ID NO:63). Ligations were performed sequentially using T4 DNA ligase and two 30 nucleotide splint oligonucleotides. The first ligation for the AS83 circle used the top splint in a reaction mixture containing 50 $\mu$M each of the 41mer and the 42mer, 60 $\mu$M splint oligonucleotide (5 'AAGTCGGAAC ATCTC-CCATC TTTCCCTGAA) (SEQ ID NO:64), 0.1 units/$\mu$L ligase (USB), 10 mM MgCl$_2$, 50 mM TrisHCl (pH 7.5), 10 mM DTT, and 100 $\mu$M ATP. The reaction was incubated at 4° C. for 14 hours. The cyclization-ligation was then carried out with a second splint (5'TCAAGAGATC CTTCTCTCAC AAGTCGAAAC) (SEQ ID NO:65) under the same conditions but with the concentration of the linear precursor lowered to 1 $\mu$M, splint to 3 $\mu$M, and enzyme to 0.33 units/$\mu$L. Products were isolated by preparative denaturing PAGE. The construction of circles H83 (FIG. 5) and AH83 (FIG. 6) was done in exactly analogous fashion, with ligations performed at the same sites (and splints of the same length but with sequence adjusted to be fully complementary). The characterization of the circles was carried out as described in E. Rubin et al., Nucleic Acids Res., 23, 3547–3553 (1995) (incorporated herein in its entirety).

The sequence of the DNA circle AS83 was designed to mimic internal segments (bases 56–98 and 147–184) of the (−) avocado sunblotch viroid (R. H. Symons, Nucleic Acids Res., 9, 6527–6537 (1981)), which contains hammerhead-motif catalytic RNAs in (+) and (−) forms (C. J. Hutchins, et al., Nucleic Acids Res., 14, 3627–3640 (1986)). The circular single-stranded DNA thus encodes a conserved hammerhead RNA sequence as well as its own substrate for cleavage; it does not, however, contain any known RNA polymerase promoter sequences. The 83 nucleotide DNA circle was constructed convergently, as described in E. Rubin et al., Nucleic Acids Res., 23, 3547–3553 (1995), in 10.5% preparative yield from 41 nucleotide and 42 nucleotide oligonucleotides by enzymatic ligation using a 30 nucleotide DNA splint followed by a second intramolecular ligation at lower concentrations using a second splint.

The circular DNA templates H83 and AH83 differed from AS83 by only a few nucleotides in the noncatalytic (substrate-binding) domains in order to alter the cleavage sequence specificity of the hammerhead RNA products. Circle H83 contained 11 nucleotides different from the initial AS83 vector; the mutations were predicted to change the ribozyme target from that of a segment of ASBV viroid RNA to that of nucleotides 1753–1767 in the gag gene of HIV-1 RNA (N. Sarver et al., *Science,* 247, 1222–1225 (1990)). The vector also encodes a short segment of its own cleavage substrate so that self-processing is possible. Circle AH83 is a chimeric mutant containing sequences encoding the putative HIV-cleaving hammerhead but with a cleavage site for the AS83 catalytic RNA; this circular vector was predicted to produce concatemeric RNAs by rolling transcription, but without subsequent self-cleavage, thus serving as a control for the self-processing mechanism of H83.

These circular DNA vectors were much smaller than standard vectors used for generation of specific RNAs; for example, plasmid DNAs are commonly two orders of magnitude larger. Molecular modeling of the AS83 circular DNA vector confirms its small size even relative to T7 RNA polymerase; the polymerase has dimensions of 65×75×75 Å, while the DNA circle has an internal diameter of about 90 Å when in the fully open (single-stranded) form. (In the absence of a polymerase, the DNA circle is likely to have significant intramolecular secondary structure.) The *E. coli* holoenzyme has an even larger diameter, at about 100×100×150 Å. The internal diameter of the circles are therefore small enough to hinder or preclude the passage of the polymerase through its center; moreover, normal turning of the enzyme around the helix axis during synthesis would require the nascent RNA strand to be pulled many times through the circle. Processive transcription on these circles must thus necessarily involve a rolling mechanism, in which the circular structure rotates about its phosphodiester bonds to avoid these potential steric problems.

Example 27

Generation of Catalytic RNAs by Rolling Transcription of Circular DNA Templates Conditions for the reactions were: 1 $\mu$M circular template (AS83, H83 or AH83), 50 units of T7 RNA polymerase (New England Biolabs), 0.5 mM ATP, GTP, CTP, 60 $\mu$M UTP, 0.27 $\mu$Ci of alpha-[$^{32}$P]UTP in a pH 8.1 (25 mM Tris.HCl) buffer containing 20 mM NaCl, 15 mM $MgCl_2$, 0.4 mM spermine-HCl, 100 $\mu$g/nl acetylated bovine serum albumin, 10 mM DTT, and 12.5 units/mL RNase inhibitor (Promega), in a total reaction volume of 15 $\mu$L. Reaction time is 1.5 hours at 37° C., and the reaction is stopped by the addition of one volume of 30 mM EDTA, 8 M urea, and frozen at −70°. When *E. coli* RNA polymerase holoenzyme (Boehringer Mannheim) was used, 2 units were added to each reaction. Reactions were heated to 90° C. for 2 minutes, and then chilled on ice before being loaded on a 10% polyacrylamide denaturing gel.

Dialysis was used to quantify RNA transcripts. The polymerase reactions for quantitation by dialysis were carried out as above, but with all four rNTP's at 0.5 mM. Aliquots (10 mL) were removed at desired time points and analyzed by removal of mononucleotides by equilibrium dialysis followed by UV quantitation of the remaining polymer, using an extinction coefficient of 11703 per nucleotide at 260 nm. The data are an average from four separate experiments.

Subjecting the circular DNA template AS83 to standard in vitro transcription conditions (J. F. Milligan et al., *Nucleic Acids Res.,* 15, 8783–8798 (1987), incorporated herein in its entirety) using either T7 or *E. coli* RNA polymerase produced, surprisingly, large amounts of RNAs ranging in length from 83 nucleotides to several kilobases. Quantitation of the RNAs produced showed that the transcription was efficient, with about 21% of the nucleotides taken up into RNA after 1.5 hours. Examination of the RNA products showed a marked, regular banding pattern which suggested sequence-specific self-processing of the RNA under the transcription conditions. The bands were visible even at quite short (15 minute) reaction times. The smallest band in the ladder was approximately 83 nucleotides in length, and bands consistent with higher multiples of 83 nucleotides were also visible. This is consistent with self-processing of the concatemeric RNA strands during the transcription reaction to yield products as short as the monomeric repeat unit (FIG. 7). Further incubation of the transcription products in the presence of 25 mM $Mg^{2+}$ showed increasing amounts of shorter bands, with the monomer band becoming predominant within about 2–3 hours.

Circles H83 and AH83 were transcribed with efficiencies similar to that of the original AS83 circular vector. Some polymerase selectivity was observed, in that T7 RNA polymerase successfully transcribed AS83 and, to a lesser extent, the chimera AH83, but transcribed the H83 circle very poorly. The *E. coli* polymerase, however, transcribed the H83 vector with high relative efficiency. Rolling transcription of the H83 circle yielded a PAGE banding pattern approximately the same as for the previous AS83 circle, while the AH83 circle yielded only very long RNAs not resolved by the gel. Agarose gel analysis showed that the RNAs from the chimeric circle ranged in length from about 500 to 7,500 nucleotides, corresponding to about 6 to 90 turns around the circular template. A lack of self-processing was observed, as expected, for the chimeric AH83, confirming the requirement for a complementary cleavage site in the RNA for self-processing during the reaction. The fact that all three circles can be transcribed with good efficiency indicated that the sequence and secondary structure variations necessary for altering ribozyme cleavage specificity can be tolerated in such a vector.

RNase T1 sequencing of the monomeric products was performed by isolating the monomer bands produced from transcription of AS83 and H83 circular vectors by excision from a PAGE gel in which transcripts were not radiolabeled. After isolation the RNAs were 5'-end-labeled with g-$^{32}$P-ATP and T4 polynucleotide kinase and treated either with base (20 mM $Na_3PO_4$, pH 12) or with RNase T1 (according to the protocol supplied by USB). Nucleotide sequencing of the monomer-length RNAs confirmed them to be the expected sequences complementary to the circular templates and resulting from the predicted autolytic processing. For the AS83 vector, the monomeric sequence was 5'-pGGAAAGUCGG AACAUCUCCC AUCUUUCCCU GAAGAGACGA AGUGAUCAAG AGAUCCUUCU CUCACAAGUC GAAACUCAGA GUCp (SEQ ID NO: 66; and for the H83 vector, the monomeric sequence was 5'-pCAAAACUCGG AACAUCUCCC AUAUUUGCU GAAGAGACGA AGUGAUCAAG AGAUCCUUCU CUCACAAGUC GAAACCAACG GUCp (SEQ ID NO:67); Control reactions confirmed the absolute requirement, for the production of RNA end product, of the polymerase, the closed circular DNA, and all four nucleotides in the transcription reaction mixture.

It is not known at present where transcription is initiated in these circular vectors, and the invention is not to be viewed as requiring initiation at any particular nucleotide on the circular DNA template. Initiation can theoretically take place at any nucleotide on the template.

Example 28

Ribozyme Cleavage of Target RNAs

To explore the possibility that the monomeric 83 nucleotide catalytic RNAs might be able to act not only in cis fashion but also in trans to cleave other target RNAs, the monomer 83 nucleotide RNA produced using the H83 vector was examined for its ability to cleave a separate short 16 nucleotide RNA strand containing nucleotides 1752–1767 from HIV-1 gag (sequence: 5'-PUUGUUGGUCCAAAAUG) (SEQ ID NO:68). A similar experiment was performed to test whether the AS83 monomer RNA, could cleave in trans a short RNA sequence from (+) ASBV (sequence: 5'-pUCUGAGUCGGAAAGG) (SEQ ID NO:69) which includes nucleotides 64–73 of avocado sunblotch viroid RNA). In addition, since multimeric ribozymes have been suggested as potentially useful biologically active agents (J. Ohkawa et al., *Proc. Natl. Acad. Sci. USA*, 90, 11302–11306 (1993)) the activity of the long-repeating RNA generated from the chimeric AH83 vector, which contained about 6 to 90 joined hammerhead motifs directed to the same HIV-1 gag RNA target, was also tested.

RNA target oligonucleotides were synthesized on an Applied Biosystems instrument using the standard RNA cycle. They were 5'-end-labeled with $^{32}$p for analysis of cleavage reactions by PAGE gels and autoradiography. The complementary target for the AS83 ribozyme is 5'-pUCUGAGUCGG AAAGG (SEQ ID NO:69) (which includes sequences 64–73 of avocado sunblotch viroid RNA), and that for the H83 and AH83 ribozymes is 5'-pUUGUUGGUCC AAAAUG (SEQ ID NO:68) (corresponding to sequences 1752–1767 of HIV-1 gag).

Monomeric RNA was produced by autolytic processing of the concatemer RNA transcript (see Examples 26 and 27). The resulting monomeric RNAs retained their hammerhead (catalytic) domains, and the loose ends resulting from self-cleavage at the substrate sequence on the concatemeric product remained attached to the catalytic domain of the monomers. Monomeric 83mer RNAs were excised from a 10% polyacrylamide denaturing gel of transcription products and eluted into 2.5 M NH$_4$OAc, and ethanol precipitated.

Multimeric RNA (from the AH83 circle) containing multiple copies of the hammerhead (catalytic) domain but a nonfunctional, modified self-cleavage sequence (see Examples 26 and 27) was isolated by ethanol precipitation following heat denaturation of the polymerase.

Cleavage reactions were carried out in a pH 8.3 buffer containing 50 mM Tris.HCl, 25 mM MgCl$_2$, and 10 mM NaCl, at 37° C. The reactions were stopped by the addition of one half-volume of 30 mM EDTA, 8 M urea, and frozen at −70° C. Reactions were heated to 90° for 2 minutes, then chilled on ice before being loaded on a 10% polyacrylamide denaturing gel.

The monomeric RNAs were found to cleave at the predicted sites in both target RNAs. The specificity of cleavage by these ribozymes was confirmed by testing the AS83 monomeric ribozyme against the HIV-RNA target and vice versa; no cleavage was seen in these cases. The multimeric RNA was also found to cleave the target sequence at the same position that the monomeric ribozyme did. Thus, both multimeric catalytic RNAs and monomeric 83 nucleotide RNAs generated by self-processing (autolytic cleavage) can serve as active ribozymes to cleave other RNAs at the expected target sequences in intermolecular fashion (trans) as well as intramolecular fashion (cis).

Example 29

Figure 8:
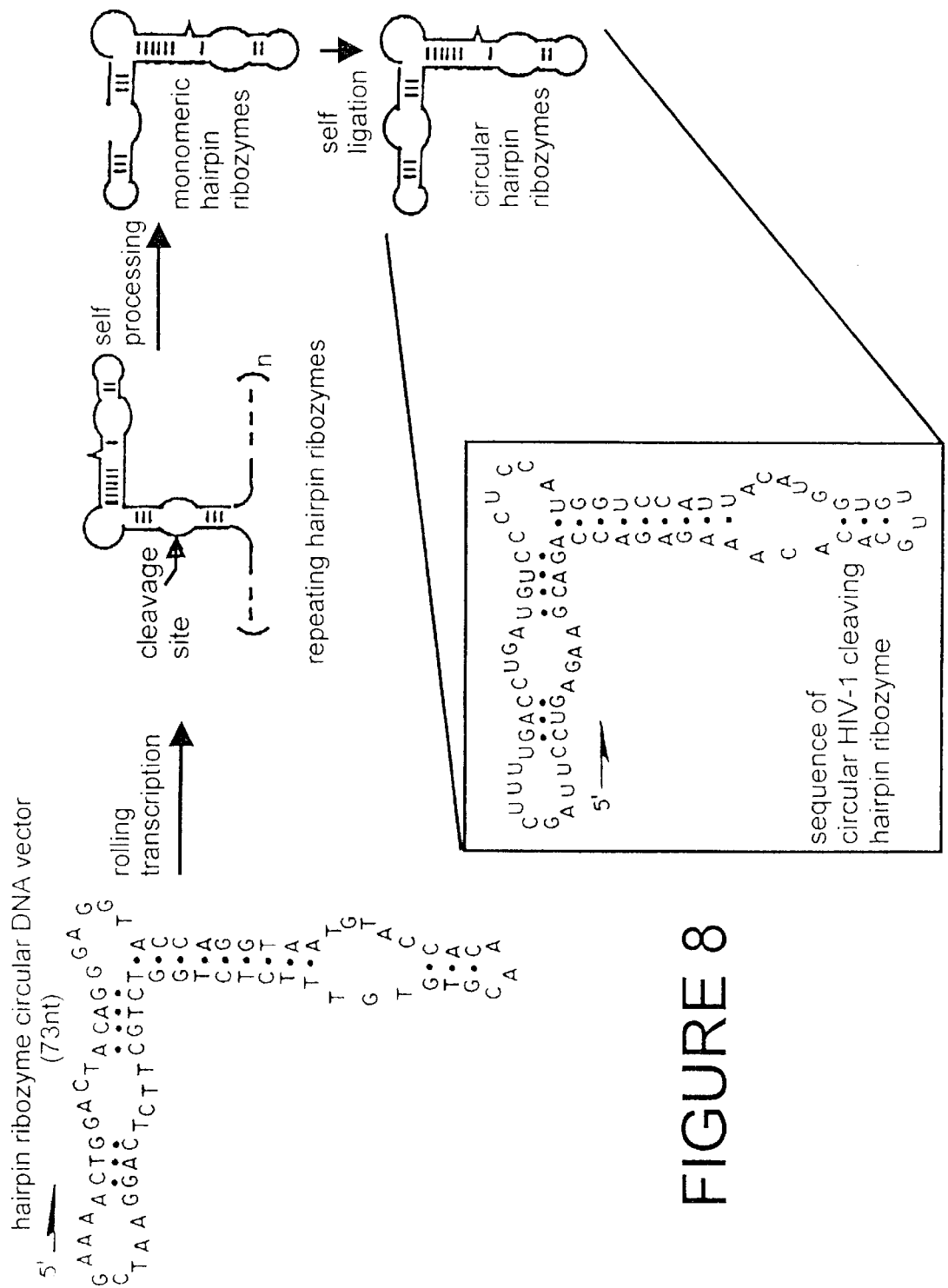
FIG. 8. Scheme for rolling transcription of synthetic nanocircle vector (SEQ ID NO:60) encoding a hairpin ribozyme and its own substrate; concatemers cleave autolytically and are ligated to form circular monomers (SEQ ID NO:16) capable of trans cleavage.

Circular DNA Vector Encoding Linear and Circular Hairpin Ribozymes that Cleave HIV-1 RNA Sequences A circular DNA 73 nucleotides in length was designed to encode a hairpin-motif ribozyme and its own substrate for cleavage (FIG. 8). Hairpin ribozymes are known to also effectively catalyze the reverse reaction, i.e., they can also induce ligation of selected RNAs.

The DNA circle was synthesized and characterized as described in Example 26 starting with two approximately half-length oligonucleotides, 5'-pCGAAAACTGG ACTACAGGGA GGTACCAGGT AATGTACC (SEQ ID NO:70), and 5'-pACAACGTGTG TTTCTCTGGT CTGCTTCTCA GGAAT (SEQ ID NO:71). It was then transcribed with *E. coli* RNA polymerase. Conditions for the transcription reactions were: 1 µM circle, 3 units of *E. coli* RNA polymerase holoenzyme (Boehringer Mannheim), 0.5 mM ATP, GTP, CTP, 60 µM UTP, 0.30 µCi of alpha-[$^{32}$P]UTP in a pH 8.1 (25 mM Tris.HCl) buffer containing 20 mM NaCl, 12 mM MgCl$_2$, 0.4 mM spermine.HCl, 100 µg/mL acetylated bovine serum albumin, 10 mM dithiothreitol (DTT), and 12.5 units/mL RNase inhibitor (Promega, Madison, Wis.), in a total reaction volume of 15 µL. Reactions were incubated at 37° C., and the reaction was stopped by the addition of one volume of 30 mM EDTA, 8 M urea, and frozen at −80°.

Transcription of this circle led to the synthesis of multimeric RNA strands containing active hairpin ribozyme sequences which were capable of being self-cleaved to yield monomer-length (73mer) RNAs which contain active hairpin ribozymes targeted to a sequence, 5'-CUGUA ↓ GUC-CAGGAA (SEQ ID NO:72), found in the HIV-1 pol gene (cleavage is predicted at the site marked "↓"). Results after 90 minutes showed that transcription gave robust amounts of RNA products consisting mainly of long products not resolved by the gel and a number of shorter discrete bands. Two dimensional (2-D) gel electrophoresis of these products revealed that these bands were chiefly linear monomer and circular monomer, with higher multimers (chiefly circular) also visible. Incubation of the RNAs in a buffer containing Mg$^{2+}$ showed that the final products were almost completely circular monomer and, to a lesser extent, linear monomer. Thus, the linear RNA transcription products were shown to be capable of being ligated intramolecularly into circles, a form which would be expected to substantially increase their resistance to intracellular degradation.

Cleavage experiments using isolated samples of circular monomer and linear monomer 73mer RNAs established that both forms could cleave HIV-1 RNAs in trans at the specific HIV-1 pol sequence predicted.

Example 30

Hybridizing Oligonucleotide Covalently Labeled with Fluorescent Multimer

A 40-mer "probe-primer" oligonucleotide (RH21) having the sequence 5'-TTGCCCACAC CGACGGCGCC CAC- CAGGAAA GAAGAAAGGA-3' (SEQ ID NO:73) was synthesized. The first 24 nucleotides (5'-TTGCCCACAC CGACGGCGCC CACC) (SEQ ID NO:74) represent the "probe" region of the "probe-primer" oligonucleotide, and are complementary to a region in the normal human Ha-ras gene centered on the twelfth codon. This "probe" region is not replicated during rolling circle synthesis of the fluorescent multimer, and is the region that hybridizes to a target sequence during various hybridization applications. The last 16 nucleotides (5'-AGGAAAGAAG AAAGGA-3') (SEQ ID NO:75) represent the "primer" region of the "probe-primer" oligonucleotide, and are complementary to a region (5'-TCCTTT CTTCTTTCCT-3') (SEQ ID NO:76) that appears twice on a 42-mer DNA circle (H21) having the sequence 5'-TTCTTTCCTT CGATTCCTTT CTTCTTTCCT TCGATTCCTT TC-3' (SEQ ID NO:77) which is used in the rolling circle synthesis described below. The palindromic nature of this sequence facilitates the use of the triplex method to close the circle.

The 40-mer probe-primer was annealed to the 42-mer DNA circle under the primer extension conditions described below prior to addition of the polymerase enzyme and mononucleotides. Annealing was done by heating to 75° C. for 2 minutes, cooling to 65° C. over 5 minutes, then cooling further to 37° C. at the rate of 1° C./minute.

The probe-primer oligomer was extended under the following conditions: 30 nM probe-primer, 30 nM DNA circle, 1.0 mM each of dATP, dGTP, dCTP, 0.75 mM dTTP, 250 μM of fluorescein-dUTP (Boehringer-Mannheim), 1 mM dithiothreitol, 10 mM $MgCl_2$, 50 mM Tris-HCl (pH 7.5), and 1.29 units/μL polymerase (KF enzyme, exo, GibcoBRL). The total reaction volume was 20 μL, and the reaction was incubated for 24 hr at 37° C. The mixture was then heat denatured (65° C.) and was analyzed by 2% agarose gel electrophoresis.

Use of the mononucleotide fluorescein-dUTP during rolling circle synthesis would allow incorporation of a fluorescent label each time an A was reached on the circle during the primer extension reaction. The 42-mer circle used in the Example contains two A's directly opposite each other, separated by 20 nucleotides. Thus, the possibility existed for incorporation of a fluorescent label twice per each lap around the circle (i.e., once per repeating 21 nucleotide oligonucleotide unit of the resulting multimer tail).

After electrophoresis the gel was examined under fluorescent light from a UV transilluminator. Bands corresponding to a few short DNAs (approximately 200–400 nucleotides) are visible; otherwise, the only visible fluorescent DNAs occur as a high-MW smear. Comparison to marker bands indicates that the longer visible multimers are greater than about 3000 nucleotides in length. The RH21 fluorescent multimer-labeled probe is isolated and hybridized to chromosome preparations on a microscope slide using standard in situ hybridization conditions taken from the literature (see, e.g., *Short Protocols in Molecular Biology*. chapter 14, 3rd Ed., Wiley (1995)). Under sufficiently stringent conditions the labeled probe binds only to the Ha-ras gene and is visible as a fluorescent spot on a chromosome by fluorescence microscopy. Hybridization conditions, probe length, and/or probe composition can be adjusted using methods well-known to one of skill in the art in order to attain the desired level of specificity and stringency.

Example 31

Detection of Streptavidin/Biotin Binding using Biotin Covalently Labeled with Fluorescent Multimer A 5'-biotinylated 40-mer oligonucleotide having the sequence 5'-biotin-UTGCCCACAC CGACGGCGCC CACCAGGAAA GAAGAAAGGA (SEQ ID NO:78) is synthesized using biotin-dU phosphoramidite (Glen Research, Sterling, Va.). The 40-mer is extended using the rolling circle method disclosed herein, during which a fluorescent label is incorporated as described in Example 30. The resulting 5'-biotinylated fluorescently labeled oligonucleotide multimer is isolated. A range of dilutions of commercial streptavidin are affixed to a nylon membrane using methods known in the art. The fluorescent multimer-labeled biotin is then contacted with the membrane, allowing it to bind the varied amounts of streptavidin on the membrane. Analysis by fluorescence imager reveals that very small amounts of streptavidin are detectable with the fluorescent multimer-labeled probe, whereas a control biotin-oligonucleotide carrying only one fluorescein label gives detectable complexes only at the highest amounts of streptavidin.

Example 32

Affinity Labeling of Specific Proteins using Fluorescent Multimer

A. RRE binding to rev protein. The RNA sequence 5'-GGUGGGGCGG GUGUUCGCAC CACGGUACAC C (SEQ ID NO:79) contains the Rev Response Element (RRE) sequence and thus binds the rev protein from HIV-1. A synthetic RNA/DNA probe-primer is generated using a DNA/RNA synthesizer. The 5' "probe" or "ligand" end of the probe-primer is RNA corresponding to the above sequence, and the 3' "primer" end contains a short (e.g., 12–16) DNA primer sequence complementary to a circular DNA template. An example of such a probe-primer is 5'-r(GGUGGGGCGG GUGUUCGCAC CACGGUACAC C)d(AGGAAAGAA GAAAGGA) (SEQ ID NO:80). Extension of this RNA/DNA chimeric probe-primer using the circle H2 1 (or other appropriately complementary circle) allows synthesis of a bright multimer label attached to this RNA ligand. This multimer-labeled ligand is then used for binding, identification, detection and quantitation of the HIV-1 rev protein in vitro, in vivo, in cells and in tissues.

B. DNA ligand that binds thrombin. The DNA sequence 5'-GGTTGGTGTGGTTGG-3' (SEQ ID NO:81) has been shown to bind human thrombin and inhibit platelet aggregation (L. Griffen et al., *Gene*, 137 25–31 (1993)). A probe-primer conjugate containing the probe region (5'-GGTTGGTGTGGTTGG-3') (SEQ ID NO:81) at the 5' end followed by the primer AGGAAAGAAG AAAGGA (SEQ ID NO:82) at the 3' end is synthesized. Extension of the resulting probe-primer (5'-GGTTGGTGTG GTTGGAG-GAAAGAAGAAAGG A-3') (SEQ ID NO:83) using the H2 1 circular template (or other appropriately complementary circle) yields a very intense affinity label for human thrombin which has utility in vitro, in vivo, in cells and in tissues.

Example 33

Detection of Bound Oligonucleotide using Hybridizing Fluorescent Multimer

A. Detection of a "padlock" probe. A circular DNA "padlock" probe is bound to a target DNA using in situ ligation according to the literature method, which is incorporated herein by reference (M. Nilsson et al., *Science*, 265, 2085–2088 (1994), incorporated in its entirety). A fluorescent multimer DNA is synthesized which contains a repeating sequence, part of which is complementary to the unhybridized portion of the padlock probe. The multimer label is then added to the bound padlock probe under conditions allowing hybridization. This results in a bright signal where the padlock probe is bound.

B. Detection of bound oligonucleotide via triplex formation. An oligonucleotide probe that hybridizes to a predetermined DNA or RNA target sequence is synthesized as a conjugate with a foldback sequence. The foldback sequence (which does not bind the target sequence) is selected such that it is capable of forming a strong "foldback" or "clamp" triplex when contacted with an oligonucleotide having a complementary sequence (R. W. Roberts et al., *Proc. Nat'l. Acad. Sci. USA,* 88, 9397–9401 (1991), incorporated in its entirety). The oligonucleotide probe conjugate is hybridized to its target in vitro, in cells or in tissues. A fluorescent oligonucleotide multimer capable of binding to the triplex-forming hairpin sequence of the oligonucleotide probe conjugate is synthesized and added to the sample. It binds to the triplex-forming sequence of the probe conjugate and thus gives an intense signal associated with the target.

Example 34

Amplified Detection using Oligonucleotide Multimer Probe Containing Multiple Copies of Target Sequence for Second, Fluorescent Multimer Probe A first oligonucleotide multimer containing a target-binding sequence at the 5' end and a repeating oligonucleotide at the 3' end is synthesized using the rolling circle method of the invention, as described for example in Example 30, except that no detectable label is incorporated therein.

A second detectably labeled oligonucleotide multimer is designed to bind the repeated oligonucleotide sequence present in the 3' tail of the first target-binding oligonucleotide multimer. This second oligonucleotide multimer is also synthesized using the rolling circle method of the invention. The oligonucleotide primer used to initiate synthesis of the second oligonucleotide multimer contains, at its 5' end, a nucleotide sequence complementary to the repeated sequence of the 3' end of the first target-binding multimer; at its 3' end, the primer contains a nucleotide sequence complementary to a circular template. The oligonucleotide primer is bound to the circular template and is extended using rolling circle synthesis with fluorescent and conventional dNTPs as described in Example 30 to yield the second linear single-stranded fluorescent oligonucleotide multimer.

The first oligonucleotide multimer containing the target-binding sequence is added to a sample suspected of containing the target sequence. The bound multimer-target complex is detected by contacting it with the second fluorescent oligonucleotide multimer, which binds to the multiple sites in the 3' tail of the first oligonucleotide multimer. The signal is thus greatly amplified by virtue of the branched binding that occurs as fluorescent multimers bind the repeated sequence of oligonucleotide multimers that are bound to the target molecule.

The sensitivity of any detection protocol based upon the use of a standard nonmultimeric oligonucleotide probe can be substantially increased by substituting therefor an oligonucleotide multimer probe of the invention that contains both a target-binding sequence and a repeating unit region. The bound complex is then detected by contacting it with a second detectably labeled oligonucleotide multimer that binds a sequence repeated in the 3' tail of the bound oligonucleotide multimer probe.

Example 35

Solid Phase Synthesis of Fluorescent Multimers

An oligonucleotide covalently or noncovalently attached to a solid support is extended with a fluorescent repeating multimer label as described in Example 31 above.

An oligonucleotide primer having a free 3' end is attached, covalently or noncovalently, to a solid support. The sequence of the 3' end is selected such that it hybridizes to a sequence present on a circular DNA template. Incubation of the circular template, the appropriate dNTPs, a fluorescent dNTP, and a suitable polymerase results in extension of the solid-bound primers to long repeating multimers which carry many fluorescent labels. Simple washing of the solid support under mildly denaturing conditions gives the pure multimer products attached to the solid support. If desired, the multimer products can be removed by reversing the attachment chemistry.

Example 36

Randomized Fluorescent Multimer Libraries Useful to Identify Optimum DNA Sequences for Binding HIV-1 rev A population of circular oligonucleotide templates each containing a constant predetermined primer binding site and a sequence-randomized domain (e.g., 30–40 nucleotides long) is synthesized. An oligonucleotide primer complementary to the primer binding site is extended in a primer extension reaction using dNTPs and fluorescein-dUTP as in Example 31. The primer extension reaction generates a library of fluorescent repeating unit DNA multimers, each strand carrying a different repeating sequence.

The resulting multimer library can be screened for binding of any chemical entity. In this example, HIV-rev is attached to a cellulose-based solid support. The multimer library is incubated with the HIV-rev/cellulose and then removed under hybridization conditions of a stringency such that only strongly binding DNAs are retained. More strongly denaturing washes are then used to remove the tight binding multimers, which are recovered and sequenced by standard bacterial cloning methods (see, for example, J. Sambrook et al., *Molecular Cloning: A Laboratory Manual,* 2nd. Ed., Cold Spring Harbor Press (1989)).

All patents, patent documents and publications cited above are incorporated by reference herein. The foregoing detailed description has been given for clarity of understanding only and no unnecessary limitations are to be understood therefrom. The invention is not limited to the exact details shown and described, for obvious modifications will occur to those skilled in the art.

What is claimed is:

1. A detectably labeled oligonucleotide multimer comprising a 5' nonrepeated region comprising a nucleotide sequence that binds a first target molecule in a sample, followed by multiple contiguous copies of a repeated oligonucleotide, wherein at least one copy of the repeated oligonucleotide comprises at least one copy of a detectable label.

2. The detectably labeled oligonucleotide multimer of claim 1 comprising multiple copies of the detectable label.

3. The detectably labeled oligonucleotide multimer of claim 1 wherein each of a multiplicity of the multiple copies of the repeated oligonucleotide comprises the detectable label.

4. The detectably labeled oligonucleotide multimer of claim 1 wherein the at least one detectable label is covalently attached to the oligonucleotide multimer.

5. The detectably labeled oligonucleotide multimer of claim 1 wherein the at least one detectable label is noncovalently attached to the oligonucleotide multimer.

6. The detectably labeled oligonucleotide multimer of claim 5 wherein the detectable label comprises a delectably labeled oligonucleotide having a nucleotide sequence complementary to at least a portion of the nucleotide sequence of the repeated oligonucleotide, wherein the detectably labeled oligonucleotide is hybridized to the oligonucleotide multimer.

7. The detectably labeled oligonucleotide multimer of claim 6 wherein the detectably labeled oligonucleotide comprises a fluorescent label, a phosphorescent label, an enzymatic label, a chemical label, or a radiolabel.

8. The detectably labeled oligonucleotide multimer of claim 7 wherein the detectably labeled oligonucleotide comprises a fluorescent label.

9. The detectably labeled oligonucleotide multimer of claim 1 comprising DNA, RNA or a derivative or analog thereof.

10. The detectably labeled oligonucleotide multimer of claim 1 wherein the 5' nonrepeated region further comprises a 5' moiety that reduces the susceptibility of the oligonucleotide multimer to enzymatic degradation.

11. The detectably labeled oligonucleotide multimer of claim 1 wherein the 5' nonrepeated region further comprises biotin.

12. The detectably labeled oligonucleotide multimer of claim 1 wherein the 5' nonrepeated region further comprises a peptide or protein.

13. The detectably labeled oligonucleotide multimer of claim 1 wherein the nucleotide sequence that binds the first target molecule comprises a RNA, DNA or a derivative or analog thereof.

14. The detectably labeled oligonucleotide multimer of claim 13 wherein the RNA, DNA or derivative or analog thereof comprises a modified backbone, a modified sugar moiety, or a modified base.

15. The detectably labeled oligonucleotide multimer of claim 13 wherein the RNA, DNA or derivative or analog thereof is selected from the group consisting of peptide nucleic acid (PNA), phosphorothioate DNA, phosphorodithioate DNA, phosphoramidate DNA, amide-linked DNA, MMI-linked DNA, 2'-O-methyl RNA, alpha-DNA, methylphosphonate DNA, 2'-O-methyl RNA, 2'-fluoro RNA, 2'-amino RNA, 2'-O-alkyl DNA, 2'-O-allyl DNA, 2'-O-alkynyl DNA, hexose DNA, pyranosyl RNA, anhydrohexitol DNA, C-5 substituted pyrimidine nucleoside, C-7 substituted 7-deazapurine nucleoside, inosine nucleoside and diaminopurine nucleoside.

16. The detectably labeled oligonucleotide multimer of claim 15 wherein the substituent of the C-5 substituted pyrimidine is selected from the group consisting of fluoro, bromo, chloro, iodo, methyl, ethyl, vinyl, formyl, alkynyl, alkenyl, thiazolyl, imidazolyl and pyridyl.

17. The detectably labeled oligonucleotide multimer of claim 15 wherein the substituent of the C-7 substituted 7-deazapurine is selected from the group consisting of fluoro, bromo, chloro, iodo, methyl, ethyl, vinyl, formyl, alkynyl, alkenyl, thiazolyl, imidazolyl and pyridyl.

18. The detectably labeled oligonucleotide multimer of claim 1 wherein the first target molecule is a nucleic acid molecule, a peptide, a protein, a carbohydrate, a lipid, a hormone, a derivative thereof or an analog thereof.

19. The detectably labeled oligonucleotide multimer of claim 18 wherein the first target molecule is a nucleic acid molecule.

20. The detectably labeled oligonucleotide multimer of claim 19 wherein the nucleotide sequence that binds the first target nucleic acid molecule is complementary to at least a portion of the nucleotide sequence of the first target nucleic acid molecule.

21. The detectably labeled oligonucleotide multimer of claim 1 wherein the 5' nonrepeated region further comprises a self-complementary hairpin nucleotide sequence such that the nucleotide sequence that binds the first target molecule comprises at least a portion of the self-complementary hairpin nucleotide sequence.

22. The detectably labeled oligonucleotide multimer of claim 1 wherein the repeated oligonucleotide comprises a nucleotide sequence that binds a second target molecule.

23. The detectably labeled oligonucleotide multimer of claim 22 wherein the second target molecule is a nucleic acid molecule, and wherein the nucleotide sequence that binds the second target nucleic acid molecule is complementary to at least a portion of the nucleotide sequence of the second target nucleic acid molecule.

24. The detectably labeled oligonucleotide multimer of claim 1 wherein the nucleotide sequence of the repeated oligonucleotide has limited complexity.

25. The detectably labeled oligonucleotide multimer of claim 24 wherein the nucleotide sequence of the repeated oligonucleotide consists of less than four nucleotide types selected from the group consisting of adenine, guanine, thymidine, cytosine and uracil.

26. The detectably labeled oligonucleotide multimer of claim 24 wherein the nucleotide sequence of the repeated oligonucleotide comprises a nucleotide type that is overrepresented in the nucleotide sequence of the repeated oligonucleotide.

27. The detectably labeled oligonucleotide multimer of claim 26 wherein the overrepresented nucleotide type is present at a level of at least about 50% in the nucleotide sequence of the repeated oligonucleotide.

28. The detectably labeled oligonucleotide multimer of claim 24 wherein the nucleotide sequence of the repeated oligonucleotide is palindromic.

29. The detectably labeled oligonucleotide multimer of claim 24 wherein the nucleotide sequence of the repeated oligonucleotide is a repeating sequence.

30. The detectably labeled oligonucleotide multimer of claim 1 wherein the detectable label is a fluorescent label, a phosphorescent label, an enzymatic label, a chemical label, or a radiolabel.

31. The detectably labeled oligonucleotide multimer of claim 1 wherein the detectable label is a digoxigenin label or a biotin label.

32. The detectably labeled oligonucleotide multimer of claim 1 wherein the detectable label comprises a radiolabel selected from the group consisting of $^{32}P$, $^{33}P$, $^{35}S$ and $^{125}I$.

33. The detectably labeled oligonucleotide multimer of claim 1 wherein the detectable label is a fluorescent label.

34. A method for synthesizing a detectable labeled oligonucleotide multimer comprising:
   (a) providing a single-stranded circular template comprising at least one copy of a nucleotide sequence complementary to the nucleotide sequence of a selected oligonucleotide;
   (b) annealing an effective amount of an oligonucleotide primer to the single-stranded circular template to yield a primed single-stranded circular template; and
   (c) combining the primed single-stranded circular template with an effective amount of at least two types of nucleotide triphosphate, at least one of the at least two types of nucleotide triphosphate comprising a detectable label and an effective amount of a polymerase enzyme, without the addition of auxiliary proteins, to yield a detectably labeled oligonucleotide multimer comprising a 5' nonrepeated region comprising a nucleotide sequence that binds a first target molecule followed by multiple contiguous copies of the selected oligonucleotide, wherein at least one copy of the selected oligonucleotide comprises at least one copy of a detectable label.

35. The method of claim 34 wherein the size of the single-stranded circular template is about 15–1500 nucleotides.

36. The method of claim 34 wherein the nucleotide triphosphate comprising the detectable label is a ribonucleotide triphosphate.

37. The method of claim 34 wherein the nucleotide triphosphate comprising the detectable label is selected from the group consisting of rATP, rTTP, rUTP, rGTP, rCTP, r(isoG)TP and r(isoC)TP.

38. The method of claim 37 wherein the nucleotide triphosphate comprising the detectable label is rUTP.

39. The method of claim 34 wherein the nucleotide triphosphate comprising the detectable label is a deoxyribonucleotide triphosphate.

40. The method of claim 34 wherein the nucleotide triphosphate comprising the detectable label is selected from the group consisting of dATP, dTTP, dUTP, dGTP, dCTP, d(isoG)TP and d(isoC)TP.

41. The method of claim 40 wherein the nucleotide triphosphate comprising the detectable label is dUTP.

42. The method of claim 34 wherein the detectable label is a fluorescent label, a phosphorescent label, an enzymatic label, a chemical label, or a radiolabel.

43. The method of claim 34 wherein the single-stranded circular template comprises only one nucleotide complementary to the nucleotide triphosphate comprising the detectable label.

44. The method of claim 34 wherein the single-stranded circular template comprises a plurality of nucleotides complementary to the nucleotide triphosphate comprising the detectable label, and wherein each of said complementary nucleotides is separated from every other said complementary nucleotide on the circular template by a separation distance of at least about 10 nucleotides.

45. The method of claim 44 wherein the separation distance is at least about 20 nucleotides.

46. The method of claim 34 further comprising (c) separating the oligonucleotide multimers from other components of the reaction mixture.

47. The method of claim 46 wherein step (c) further comprises separating oligonucleotide multimers of at least about 1000 nucleotides in length from other components of the reaction mixture.

48. The method of claim 34 wherein the oligonucleotide multimer comprises RNA.

49. The method of claim 34 wherein the oligonucleotide primer is at least 6 nucleotides in length.

50. The method of claim 34 wherein the oligonucleotide primer comprises the nucleotide sequence that binds the first target molecule.

51. The method of claim 34 wherein the oligonucleotide multimer comprises DNA.

52. A method for detecting a target molecule comprising:
   (a) contacting the detectably labeled oligonucleotide multimer of claim 1 with a sample suspected of containing the target molecule to yield a detectably labeled bound multimer-target complex; and
   (b) detecting the detectably labeled bound multimer-target complex.

53. The method of claim 52 wherein the 5' nonrepeated region of the detectably labeled oligonucleotide multimer further comprises biotin.

54. The method of claim 53 wherein the first target molecule comprises a nucleic acid molecule.

55. The method of claim 52 further comprising, prior to step (a), contacting the detectably labeled oligonucleotide multimer with a blocking oligonucleotide having a nucleotide sequence complementary to at least a portion of the nucleotide sequence of the repeated oligonucleotide.

56. The detectably labeled oligonucleotide multimer of claim 8 wherein each copy of the fluorescent label is separated from every other copy of the fluorescent label on the oligonucleotide multimer by a separation distance of at least about 10 nucleotides.

57. The detectably labeled oligonucleotide multimer of claim 56 wherein the separation distance is at least about 20 nucleotides.

58. The detectably labeled oligonucleotide multimer of claim 33 wherein each copy of the fluorescent label is separated from every other copy of the fluorescent label on the oligonucleotide multimer by a separation distance of at least about 10 nucleotides.

59. The detectably labeled oligonucleotide multimer of claim 58 wherein the separation distance is at least about 20 nucleotides.

60. A detectably labeled oligonucleotide multimer comprising multiple copies of a fluorescent label, the oligonucleotide multimer further comprising a 5' nonrepeated region comprising a nucleotide sequence that binds a target molecule in a sample, followed by multiple contiguous copies of a repeated oligonucleotide wherein at least one copy of the repeated oligonucleotide comprises at least one copy of a fluorescent label and wherein the multiple copies of the fluorescent label are positioned within the oligonucleotide multimer such that each copy of the fluorescent label is separated from every other copy of the fluorescent label on the oligonucleotide multimer by a separation distance of at least about 10 nucleotides.

61. The detectably labeled oligonucleotide multimer of claim 60 wherein the separation distance is at least about 20 nucleotides.

62. The detectably labeled oligonucleotide multimer of claim 60 comprising DNA, RNA or a derivative or analog thereof.

63. The detectably labeled oligonucleotide multimer of claim 60 wherein the target molecule is a nucleic acid molecule, a peptide, a protein, a carbohydrate, a lipid, a hormone, a derivative thereof or an analog thereof.

64. The detectably labeled oligonucleotide multimer of claim 63 wherein the target molecule is a nucleic acid molecule.

65. The detectably labeled oligonucleotide multimer of claim 64 wherein the binding region comprises a nucleotide sequence complementary to at least a portion of the nucleotide sequence of the target nucleic acid molecule.

66. The detectably labeled oligonucleotide multimer of claim 60 wherein the nucleotide sequence of the repeated oligonucleotide has limited complexity.

* * * * *

UNITED STATES PATENT AND TRADEMARK OFFICE
CERTIFICATE OF CORRECTION

PATENT NO.   : 6,077,668
DATED        : June 20, 2000
INVENTOR(S)  : Eric T. Kool It is certified that error appears in the above-identified patent and that said Letters Patent is hereby corrected as shown below:

Title page,
Item [56] References Cited, FOREIGN PATENT DOCUMENTS, change the date of publication for "WO 92/01813" from "2/1993" to -- 2/1992 --.
Item [56] References Cited, FOREIGN PATENT DOCUMENTS, between "WO 94/03630 2/1994 WIPO." and "96/33207 10/1996 WIPO." insert -- WO 96/00795 1/1996 WIPO. --.

Column 3,
Item [56] References Cited, OTHER PUBLICATIONS, between "Chin, J., et al.," and "Compton, J.," insert -- Chowrira, B.M., et al., "*In Vitro* and *In Vivo* Comparison of Hammerhead, Hairpin, and Hepatitis Delta Virus Self-Processing Ribozyme Cassettes," Journal of Biological Chemistry, 269, 25856-25864 (1994). --.

Column 4,
Item [56] References Cited, OTHER PUBLICATIONS, between "Haseloff, J., et al.," and "Horn, T. et al.," insert -- Hoffman, L.M., et al., "Emzymatic Synthesis of Milligram Quantities of Ribozymes in Small Volume," Bio Techniques, 17, 372-375 (1994). --.
Item [56] Reference Cited, OTHER PUBLICATIONS, between "Kitajima, I., et al.," and "Koo, Hyeon-Sook, et al.," insert -- Koizumi, M., et al., "Ribozymes Designed to Inhibit Transformation of NIH3T3 Cells by the Activated c-Ha-*ras* Gene," Gene, 117, 179-184 (1992). --.

Column 6,
Item [56] References Cited, OTHER PUBLICATIONS, in the "Taira, K. et al.," citation, cancel "RNA-transcript-t-rimming" and insert therefor -- RNA-transcript-trimming --.
Lines 29 and 30, after "hammerhead-motif RNAs" cancel "(SEQ ID NOS:58)" and insert therefor -- (SEQ ID NO:58) --.
Line 36, before "capable" cancel "(SEQ ID NO:16)" and insert therefor -- (SEQ ID NO:61) --.

Column 81,
Line 46, after "comprises a" cancel "delectably" and insert therefor -- detectably --.

UNITED STATES PATENT AND TRADEMARK OFFICE
CERTIFICATE OF CORRECTION

PATENT NO.   : 6,077,668
DATED         : June 20, 2000
INVENTOR(S)  : Eric T. Kool It is certified that error appears in the above-identified patent and that said Letters Patent is hereby corrected as shown below:

Column 83,
Line 54, before "labeled" cancel "detectable" and insert therefor -- detectably --.
Line 67, after "label" but before "and" insert -- , --.

Signed and Sealed this

Fourth Day of December, 2001

*Attest:*

NICHOLAS P. GODICI
*Attesting Officer* — Acting Director of the United States Patent and Trademark Office